(12) United States Patent
Srivastava et al.

(10) Patent No.: US 12,423,780 B2
(45) Date of Patent: Sep. 23, 2025

(54) WAVELET DENOISING USING SIGNAL LOCATION WINDOWING

(71) Applicant: CORNELL UNIVERSITY, Ithaca, NY (US)

(72) Inventors: Madhur Srivastava, Ithaca, NY (US); Jack H. Freed, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 447 days.

(21) Appl. No.: 18/012,426

(22) PCT Filed: Jun. 24, 2021

(86) PCT No.: PCT/US2021/038933
§ 371 (c)(1),
(2) Date: Dec. 22, 2022

(87) PCT Pub. No.: WO2021/263006
PCT Pub. Date: Dec. 30, 2021

(65) Prior Publication Data
US 2023/0260087 A1    Aug. 17, 2023

Related U.S. Application Data

(60) Provisional application No. 63/043,447, filed on Jun. 24, 2020.

(51) Int. Cl.
*G06T 5/70*    (2024.01)
*G06F 17/14*    (2006.01)

(52) U.S. Cl.
CPC .............. *G06T 5/70* (2024.01); *G06F 17/148* (2013.01); *G06T 2207/20016* (2013.01); *G06T 2207/20064* (2013.01)

(58) Field of Classification Search
CPC ... G06T 5/70; G06T 5/00; G06T 2207/20016; G06T 2207/20064; G06F 17/148
See application file for complete search history.

(56) References Cited

U.S. PATENT DOCUMENTS 6,801,672 B1 * 10/2004 Thomas .................... G06T 7/13
382/167
2008/0183466 A1 * 7/2008 Nongpiur ............ G10L 19/0216
704/226

(Continued)

FOREIGN PATENT DOCUMENTS

WO    2013043157 A2    3/2013

OTHER PUBLICATIONS

Extended European search report dated Sep. 24, 2024 received in European Patent Application No. 21828213.5.
(Continued)

*Primary Examiner* — Sean T Motsinger
(74) *Attorney, Agent, or Firm* — Scullt, Scott, Murphy & Presser, P.C.

(57) ABSTRACT

Methods, systems and programs for denoising a signal using an undecimated discrete wavelet transformation are provided. The methods use signal location windows. The signal location windows may be used before or after thresholding. When signal location windows are used after thresholding coefficients within the signal location windows may be restored to their original values. When signal location windows are used before thresholding, coefficients within the signal location windows may be unchanged by the thresholding. The signal location windows may be used only on a subset of decomposition levels that are thresholded. The signal location windows may be used on both the Detail components and the highest decomposition level for thresholding of the Approximation component.

32 Claims, 31 Drawing Sheets
(28 of 31 Drawing Sheet(s) Filed in Color)

(56) References Cited

U.S. PATENT DOCUMENTS

| | | | | |
|---|---|---|---|---|
| 2014/0233820 | A1* | 8/2014 | Wu | A61B 6/5211 |
| | | | | 382/131 |
| 2016/0022164 | A1* | 1/2016 | Brockway | A61B 5/7203 |
| | | | | 600/509 |
| 2017/0301095 | A1* | 10/2017 | Zhang | G06T 5/10 |
| 2017/0318240 | A1* | 11/2017 | Yu | H04N 23/10 |
| 2019/0287220 | A1* | 9/2019 | Srivastava | G06F 17/148 |
| 2023/0119747 | A1* | 4/2023 | Izadi | G06T 5/70 |
| | | | | 382/254 |
| 2023/0260087 | A1* | 8/2023 | Srivastava | G06F 17/148 |
| | | | | 382/131 |

OTHER PUBLICATIONS

Li, Y., "Image Denoising Based on Undecimated Discrete Wavelet Transform", Proceedings of the 2007 International Conference on Wavelet Analysis and Pattern Recognition, Nov. 2007, pp. 527-531.
Gopi, V. et al., "Image Denoising Based on Undecimated Double Density Dual Tree Wavelet Transform and Modified Firm Shrinkage", 2013 2nd International Conference on Advanced Computing, Networking and Security, Dec. 2013, pp. 68-73.
Goossens, B. et al., "Removal of Correlated Noise by Modeling the Signal of Interest in the Wavelet Domain", IEEE Transactions on Image Processing, Jun. 2009, pp. 1153-1165, vol. 18, No. 6.
Cai, T. et al., "Incorporating information on neighbouring coefficients into wavelet estimation", Sankhya: The Indian Journal of Statistics, Series B (1960-2002), 2001, pp. 127-148, vol. 63, No. 2.
Jiang, J. et al., "An improved adaptive wavelet denoising method based on neighboring coefficients", 2010 8th World Congress on Intelligent Control and Automation, Jul. 2010, pp. 2894-2898.
Zhao, Q et al., "A wavelet denoising method of new adjustable threshold", 2015 IEEE 16th International Conference on Communication Technology (ICCT), 2015, pp. 684-688.
Madadi, Z. et al., "Signal detection in generalized gaussian noise by nonlinear wavelet denoising", IEEE Transactions on Circuits and Systems I: Regular Papers, Nov. 2013, pp. 2973-2986, vol. 60, No. 11.
Deng, G. et al., "A wavelet image denoising based on the new threshold function", 2015 11th International Conference on Computational Intelligence and Security (CIS), 2015, pp. 158-161.
Bibina, V. et al., "Adaptive wavelet thresholding joint bilateral filtering for image denoising", 2012 Annual IEEE India Conference (INDICON), 2012, pp. 1100-1104.
Guo, S. et al., "A novel wavelet denoising method used for droplet volume detection in the microfluidic system", IEEE International Conference on Mechatronics and Automation, 2013, pp. 1732-1737.
Chen, G. et al., "Wavelet-based denoising: A brief review", 2013 Fourth International Conference on Intelligent Control and Information Processing (ICICIP), 2013, pp. 570-574.
Chen, G. et al., "Multiwavelets denoising using neighboring coefficients", IEEE Signal Processing Letters, Jul. 2003, pp. 211-214, vol. 10, No. 7.
Chen, G. et al., "Image denoising using neighbouring wavelet coefficients", Integrated Computer-Aided Engineering, 2004, pp. II-917 to II-920, vol. 12, No. 1.
Dengwen, Z. et al., "Image denoising with an optimal threshold and neighbouring window", Pattern Recognition Letters, 2008, pp. 1694-1697, vol. 29, No. 11.
Madhu, B. et al., "A novel algorithm for denoising of simulated partial discharge signals using adaptive wavelet thresholding methods", 2015 2nd International Conference on Electronics and Communication Systems (ICECS), 2015, pp. 1596-1602.
Hussein, R. et al., "Histogram-based thresholding in discrete wavelet transform for partial discharge signal denoising", 2015 International Conference on Communications, Signal Processing, and their Applications (ICCSPA'15), 2015, pp. 1-5.
Cetin, A. et al., "Projection-based wavelet denoising [lecture notes]", IEEE Signal Processing Magazine, Sep. 2015, pp. 120-124, vol. 32, No. 5.
Zhao, R. et al., "Improved threshold denoising method based on wavelet transform", 2015 7th International Conference on Modelling, Identification and Control (ICMIC), Dec. 2015, pp. 1-4.
Ding, Y. et al., "Artifact-free wavelet denoising: Non-convex sparse regularization, convex optimization", IEEE Signal Processing Letters, Sep. 2015, pp. 1364-1368, vol. 22, No. 9.
Dayong, N. et al., "Adaptive noise reduction method of synchronous hydraulic motor acoustic signal based on improved dislocation superposition method", IEEE Access, Mar. 2020, pp. 37161-37172, vol. 8.
Fodor, I. et al., "Denoising through wavelet shrinkage: an empirical study", Journal of Electronic Imaging, Jan. 2003, pp. 151-160, vol. 12, No. 1.
Wink, A. et al., "Denoising functional mr images: a comparison of wavelet denoising and gaussian smoothing", IEEE Transactions on Medical Imaging, Mar. 2004, pp. 374-387, vol. 23, No. 3.
Donoho, D., "De-noising by soft-thresholding", IEEE Transactions on Information Theory, 1995, pp. 1-37, vol. 41, No. 3.
Donoho, D. et al., "Ideal spatial adaptation by wavelet shrinkage", Biometrika, 1992, pp. 425-455, vol. 81, No. 3.
Srivastava, M. et al., "A new wavelet denoising method for selecting decomposition levels and noise thresholds", IEEE Access, 2016, pp. 1-15, vol. 4.
Srivastava, M. et al., "A new wavelet denoising method for experimental time-domain signals: Pulsed dipolar electron spin resonance", The Journal of Physical Chemistry A, 2017, pp. 2452-2465, vol. 121, No. 12.
Weil, J. et al., "Electron Paramagnetic Resonance: Elementary Theory and Practical Applications", Journal of Chemical Education, Jan. 2009, pp. 33-35, vol. 86, No. 1.
Freed, J., "New technologies in electron spin resonance", Annual Review of Physical Chemistry, 2000, pp. 655-689, vol. 51, No. 1.
Fichou, Y. et al., "Cofactors are essential constituents of stable and seeding-active tau fibrils", Proceedings of the National Academy of Sciences, 2018, pp. 1-6, vol. 115, No. 52.
Dikiy, I. et al., "Insights into histidine kinase activation mechanisms from the monomeric blue light sensor EL346", Proceedings of the National Academy of Sciences, Mar. 2019, pp. 4963-4972, vol. 116, No. 11.
Merz, G. et al., "Site-specific incorporation of a cu2+ spin label into proteins for measuring distances by pulsed dipolar electron spin resonance spectroscopy," The Journal of Physical Chemistry B, 2018, pp. 9443-9451, vol. 122, No. 41.
Selesnick, I., "The Double Density DWT", Wavelets in Signal and Image Analysis, 2001, ch. pp. 39-66.
Selesnick, I., "A higher density discrete wavelet transform", IEEE Transactions on Signal Processing, 2006, pp. 3039-3048, vol. 54, No. 8.
Qin, Y. et al., "Dense framelets with two generators and their application in mechanical fault diagnosis", Mechanical Systems and Signal Processing, 2013, pp. 483-498, vol. 40, No. 2.
Qin, Y. et al., "M-band flexible wavelet transform and its application to the fault diagnosis of planetary gear transmission systems", Mechanical Systems and Signal Processing, 2019, pp. 1-26, vol. 134.
Starck, J. et al., "The undecimated wavelet decomposition and its reconstruction", IEEE Transactions on Image Processing, Feb. 2007, pp. 297-309, vol. 16, No. 2.
Antoniadis, A., "Wavelets in Statistics: A Review", Statistical Methods and Applications, 1997, pp. 1-34.
Hofbauer, W. et al., "High-power 95 ghz pulsed electron spin resonance spectrometer", Review of Scientific Instruments, May 2004, pp. 1194-1208, vol. 75, No. 5.
Freed, J., "Biomedical EPR, Part B: Methodology, Instrumentation, and Dynamics", ESR and Molecular Dynamics, 2005, pp. 239-268.
Wang, Z. et al., "Image quality assessment: from error visibility to structural similarity", IEEE Transactions on Image Processing, Apr. 2004, pp. 1-14, vol. 13, No. 4.
Cohen, R., "Signal denoising using wavelets", Technion, Israel Institute of Technology, Tech. Rep., Feb. 2012, pp. 1-27.
Poornachandra, S. et al., "Waveshrink using modified hyper-shrinkage function", Engineering in Medicine and Biology Society, 27th Annual International Conference, 2005, pp. 30-32, vol. 4.

(56) References Cited

OTHER PUBLICATIONS

Zhang, L. et al., "Denoising by spatial correlation thresholding", IEEE Transactions on Circuits and Systems for Video Technology, Jun. 2003, pp. 535-538, vol. 13, No. 6.
Lin, Y et al., "A new threshold function for signal denoising based on wavelet transform", IEEE International Conference on Measuring Technology and Mechatronics Automation, 2010, pp. 200-203.
Coombes, K. et al., "Improved peak detection and quantification of mass spectrometry data acquired from surface-enhanced laser desorption and ionization by denoising spectra with the undecimated discrete wavelet transform", Proteomics, Nov. 2005, pp. 4107-4117, vol. 5, No. 16.
Brassarote, G.O.N. et al., "Non-decimated Wavelet Transform for a Shift-invariant Analysis", Tend. Mat. Apl. Comput., 2018, pp. 93-110, vol. 19, No. 1.
Srivastava, M. et al., "A New Wavelet Denoising Method for Selecting Decomposition Levels and Noise Thresholds", IEEE Access, 2016, pp. 3862-3877, vol. 4.
International Search Report and Written Opinion dated Sep. 30, 2021 received in International Application No. PCT/US2021/038933.

\* cited by examiner

Related
Art

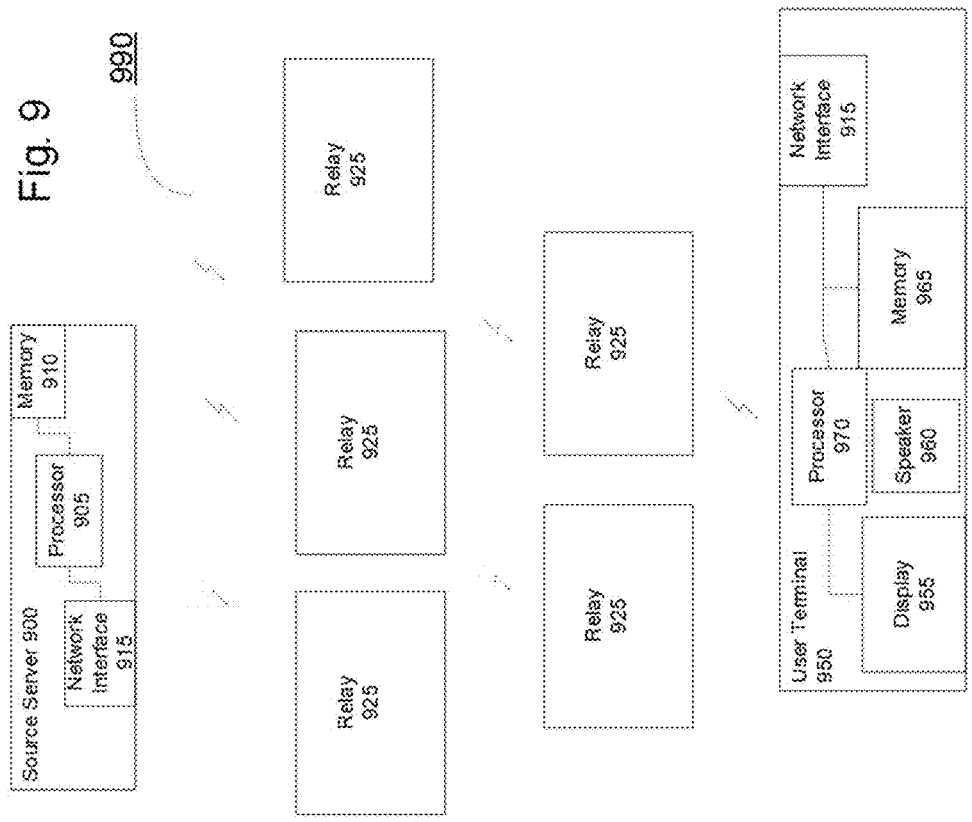

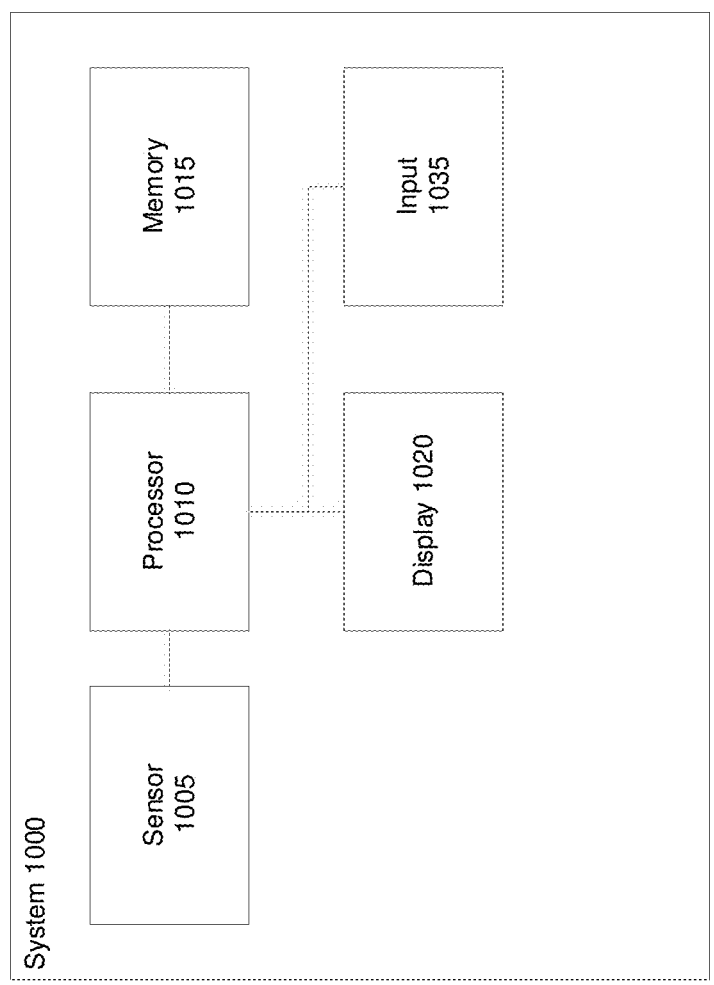

Fig. 16

TABLE 1

| Data Averaging | | Noisy SNR | Noisy SSIM | Denoised SSIM Wav-SAF | Denoised SSIM NERD |
|---|---|---|---|---|---|
| 16-scan | Signal | 57 | 0.9899 | 0.9936 | 0.9975 |
| | Peak 1 | 0.5 | 0.1885 | 0.4904 | 0.8244 |
| | Peak 2 | 15 | 0.9967 | 0.9972 | 0.9976 |
| | Peak 3 | 10 | 0.9925 | 0.9920 | 0.9942 |
| | Peak 4 | 0.7 | 0.1027 | 0.3132 | 0.8329 |
| | Peak 5 | 0.7 | 0.2018 | 0.6021 | 0.7274 |
| | Peak 6 | 14 | 0.9970 | 0.9975 | 0.9975 |
| | Peak 7 | 14 | 0.9962 | 0.9972 | 0.9974 |
| | Peak 8 | 0.9 | 0.1980 | 0.6246 | 0.6149 |
| | Peak 9 | 1.1 | 0.3249 | 0.6140 | 0.9267 |
| | Peak 10 | 19 | 0.9985 | 0.9983 | 0.9987 |
| | Peak 11 | 20 | 0.9985 | 0.9989 | 0.9988 |
| | Peak 12 | 0.8 | 0.0811 | 0.1245 | 0.5439 |
| 4-scan | Signal | 15 | 0.9724 | 0.9909 | 0.9992 |
| | Peak 1 | 0.3 | 0.0067 | 0.5053 | 0.1201 |
| | Peak 2 | 9 | 0.9931 | 0.9957 | 0.9974 |
| | Peak 3 | 8 | 0.9896 | 0.9923 | 0.9936 |
| | Peak 4 | 0.3 | -0.0264 | 0.0973 | 0.1949 |
| | Peak 5 | 0.3 | 0.0133 | 0.0753 | 0.6668 |
| | Peak 6 | 10 | 0.9939 | 0.9966 | 0.9985 |
| | Peak 7 | 7 | 0.9866 | 0.9917 | 0.9940 |
| | Peak 8 | 0.4 | 0.0393 | 0.1225 | 0.7683 |
| | Peak 9 | 0.4 | 0.1077 | 0.3955 | 0.8161 |
| | Peak 10 | 8 | 0.9923 | 0.9955 | 0.9968 |
| | Peak 11 | 7 | 0.9904 | 0.9931 | 0.9934 |
| | Peak 12 | 0.4 | 0.0565 | 0.1759 | 0.8455 |

Fig. 17
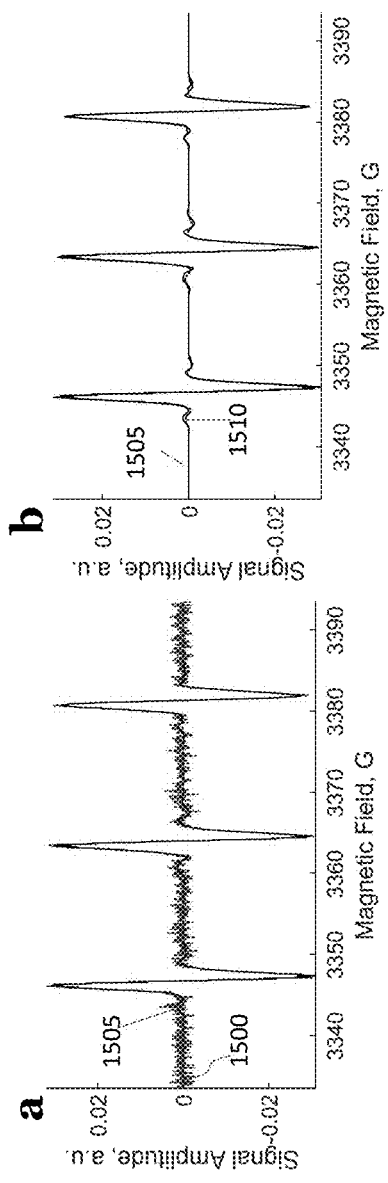
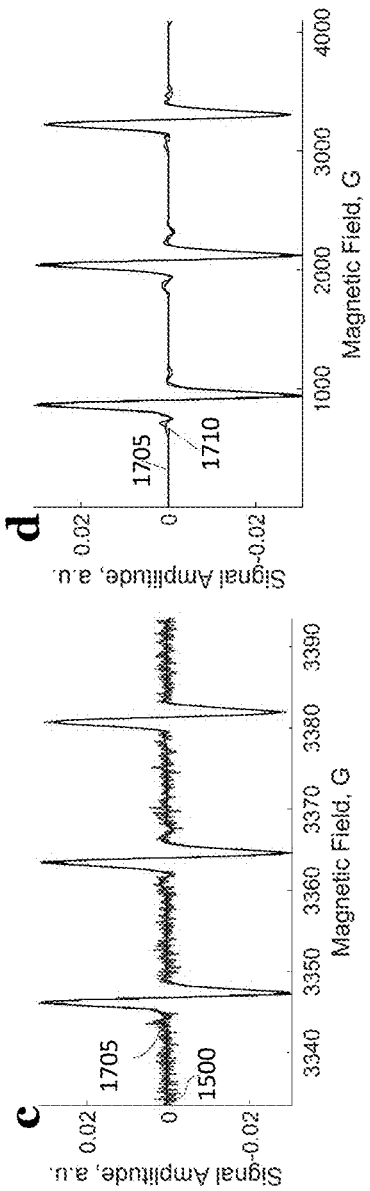

Fig. 18
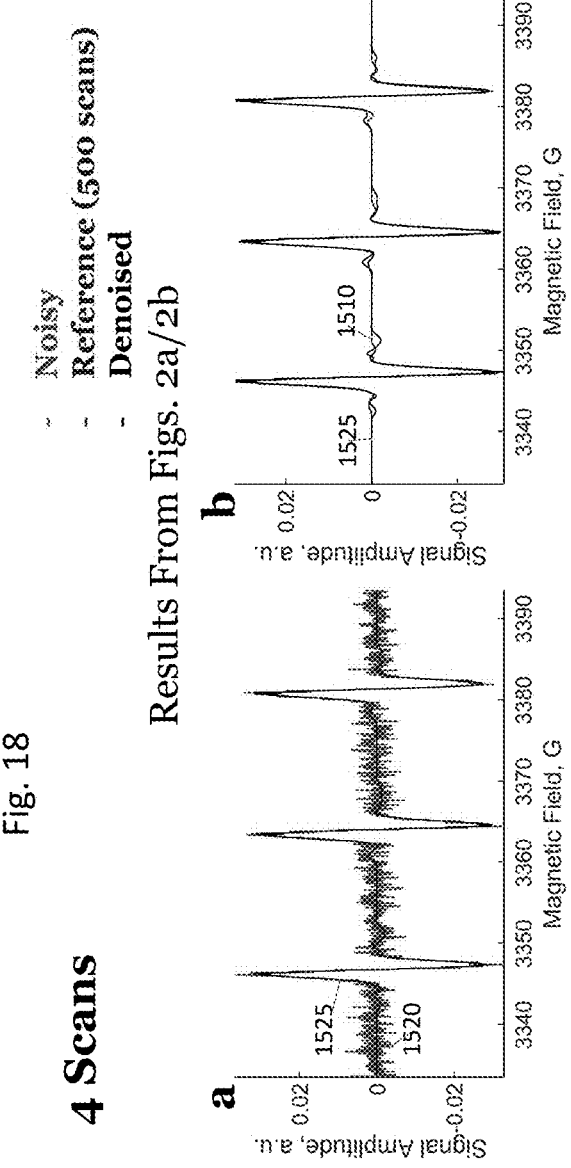
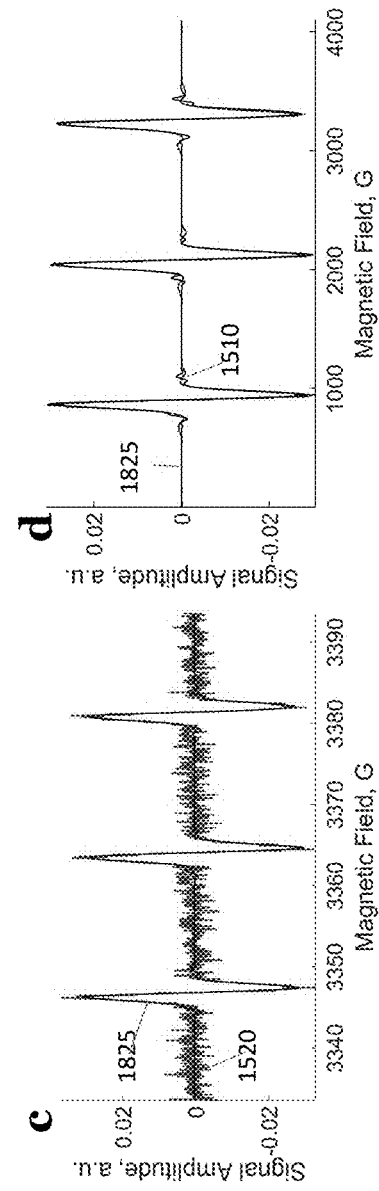

Fig. 20
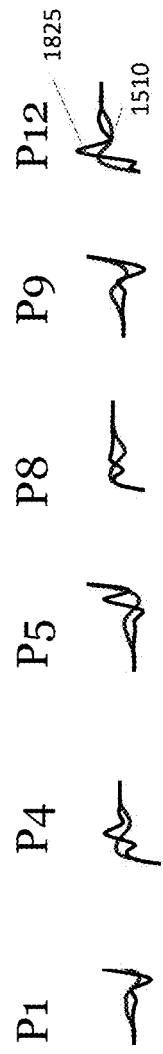

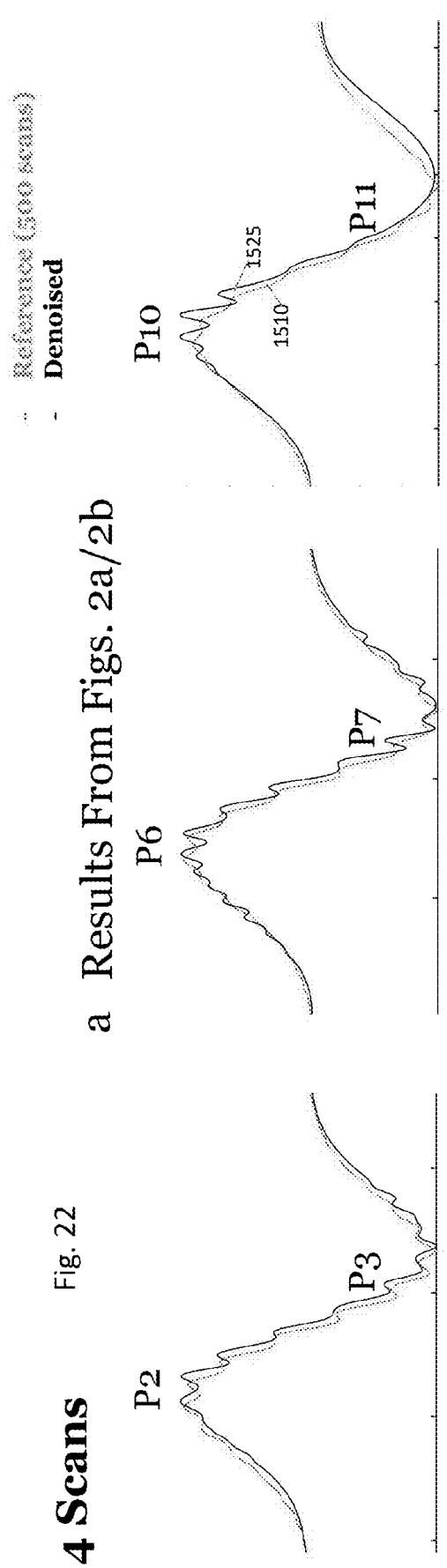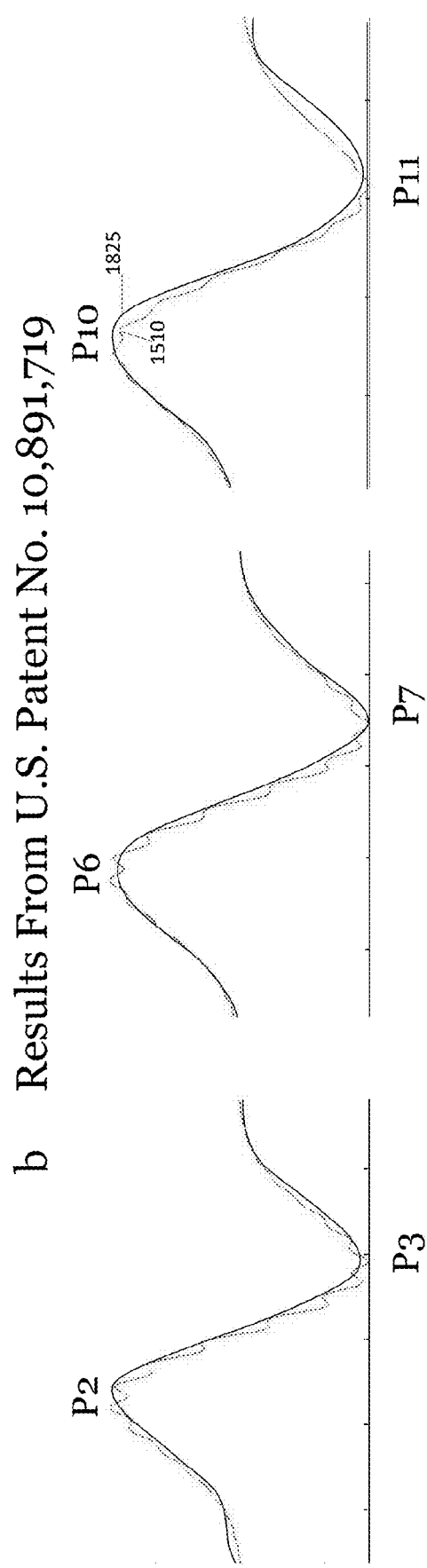
Fig. 22

Fig. 25

TABLE 2

| Data Averaging | | SNR | | | SSIM | | |
|---|---|---|---|---|---|---|---|
| | | Noisy | Wav-SAF | NERD | Noisy | Wav-SAF | NERD |
| 18-scan | Signal | 73 | 4.9 x 10⁵ | 1.1 x 10⁸ | NA | NA | NA |
| | Peak 1 | 38 | 2.6 x 10⁶ | 6.1 x 10⁷ | NA | NA | NA |
| | Peak 2 | 17 | 1.7 x 10⁶ | 2.5 x 10⁷ | NA | NA | NA |
| | Peak 3 | 2.7 | 2.2 x 10⁵ | 5.1 x 10⁶ | NA | NA | NA |
| | Peak 4 | 32 | 2.3 x 10⁶ | 5.3 x 10⁷ | NA | NA | NA |
| | Peak 5 | 13 | 1.1 x 10⁶ | 2.4 x 10⁷ | NA | NA | NA |
| | Peak 6 | 9 | 6.4 x 10⁵ | 1.4 x 10⁷ | NA | NA | NA |
| 4-scan | Signal | 33 | 2.1 x 10⁵ | 1.1 x 10⁵ | 0.8830 | NA | 0.9968 |
| | Peak 1 | 17 | 1.1 x 10⁴ | 6.04 x 10⁴ | 0.9073 | 0.9961 | 0.9934 |
| | Peak 2 | 8 | 4.9 x 10³ | 2.5 x 10⁴ | 0.9269 | 0.9823 | 0.9899 |
| | Peak 3 | 3 | 1.2 x 10³ | 5.8 x 10³ | 0.8741 | 0.9732 | 0.9753 |
| | Peak 4 | 14 | 9.9 x 10³ | 5.3 x 10⁴ | 0.9208 | 0.9938 | 0.9964 |
| | Peak 5 | 7 | 4.5 x 10³ | 2.4 x 10⁴ | 0.9182 | 0.9982 | 0.9982 |
| | Peak 6 | 6 | 2.6 x 10³ | 1.3 x 10⁴ | 0.8971 | 0.9939 | 0.9945 |
| 1-scan | Signal | 21 | 612 | 3.2 x 10⁴ | 0.6938 | 0.9845 | 0.9946 |
| | Peak 1 | 9 | 322 | 1.7 x 10⁴ | 0.7684 | 0.9889 | 0.9978 |
| | Peak 2 | 4 | 161 | 8.1 x 10³ | 0.7324 | 0.9658 | 0.9804 |
| | Peak 3 | 2 | 41 | 2.1 x 10³ | 0.6554 | 0.9294 | 0.9391 |
| | Peak 4 | 9 | 283 | 1.5 x 10⁴ | 0.8018 | 0.9872 | 0.9935 |
| | Peak 5 | 4 | 87 | 5.7 x 10³ | 0.7827 | 0.9596 | 0.9866 |
| | Peak 6 | 5 | 98 | 4.6 x 10³ | 0.6823 | 0.9558 | 0.9895 |

Fig. 27
Table 3

| | Noisy | Wav-SAF | NERD | Reference |
|---|---|---|---|---|
| SNR | 1.1 | NA | $8.5 \times 10^3$ | NA |
| SSIM | 0.08 | 0.5563 | 0.9608 | NA |
| Hyperfine Lines | NA | 26 | 66 | 66 |

WAVELET DENOISING USING SIGNAL LOCATION WINDOWING

CROSS-REFERENCE TO RELATED APPLICATIONS

This application claims the benefit of and priority to U.S. Provisional Application Ser. No. 63/043,447 filed on Jun. 24, 2020, the contents of which is incorporated herein by reference.

STATEMENT REGARDING FEDERALLY SPONSORED RESEARCH AND DEVELOPMENT

This invention was made with government support under contract no. GM103521 awarded by the National Institutes of Health. The government has certain rights in the invention.

FIELD OF THE DISCLOSURE

This disclosure relates to denoising signals using wavelet transformation.

BACKGROUND

Noise is generally unwanted components of a signal that can arise from acquisition, storing, transmission and processing. Noise is typically a natural result of electronic circuits and signal cables.

Noise in signals can cause many problems. For example, noise can cause an inaccurate representation or determination of the data in the signal or no determination at all. Where data is being transmitted from a remote location, noise can cause download gaps or interruptions. This results in either an increase in download time (which increases the bandwidth needed for transmission) and/or missing data. Noise also may have different impact on different types of signals. For example, when the signal contains audio and the audio is listened to, the noise in the audio may be audible in the form of buzzing, whereas when the signal contains video, the noise in the video may be visually seen on a display in the form of pixels, bars, or strips being incorrect or blank. Noise may also impede experimental studies by reducing signal resolution and/or suppressing weak signals.

Signal averaging and filtering may be used to reduce noise, but they have limited effectiveness.

U.S. Pat. No. 10,891,719 describes techniques to denoise signals with a wavelet transformation-based approach to effectively removes signals from noise. The approach in the U.S. Pat. No. 10,891,719 uses a decimated discrete wavelet transformation (DWT) which downsamples the detail and approximation components by 2 at each decomposition level. For example, alternative data points may be removed.

FIG. 1 shows a block diagram of an example of a DWT and an inverse discrete wavelet transformation (IDWT). $f[t_m]$ is the discrete input signal, and $D_j$ and $A_j$ are the Detail and Approximation components, respectively, at decomposition level j. The arrows represent downsampling and upsampling by a factor of 2, respectively.

The reduced number of wavelet coefficients also reduces the information available to distinguish noise coefficients from signal coefficients. With a downsampling of data by 2 at each stage of decomposition level, the signal resolution is reduced by a factor of 2. The selectivity and sensitivity of frequency information (called resolution) of a signal are blurred, especially at lower frequencies. However, removing noise in experimental signals requires high resolution at all frequencies.

In wavelet denoising methods, the wavelet family may be selected to achieve:

$$\max(|w_j^{Noise} \geq 0|) < \min(|w_j^{Signal} \geq 0|) \qquad (1)$$

$$\max(|w_j^{Noise} < 0|) < \min(|w_j^{Signal} < 0|) \qquad (2)$$

where $w_j$ are coefficients in the jth decomposition level and where $w^{Noise}$ and $w^{Signal}$ are noise and signal coefficients, respectively, of Detail or Approximation components. This assumes that each wavelet coefficient is either a signal coefficient or a noise coefficient. This is particularly true for higher SNRs where the noise contribution is relatively small and is separated out in the first few Detail components.

However there may be situations where both signal and noise exist in a wavelet coefficient, so it can be taken as a signal or a noise coefficient based on which one dominates, because the other's contribution to the coefficient is small.

For smaller SNRs (e.g. of the order of unity) equations 1 and 2 will no longer be generally applicable; in this situation, signal coefficients can have magnitudes smaller than the noise coefficients.

SUMMARY

Accordingly, disclosed are methods for denoising a signal. For example, a method of denoising a signal may comprise transforming a signal using an undecimated discrete wavelet transformation into at least a first wavelet component. The first wavelet component may have a plurality of decomposition levels, where each level has a plurality of coefficients. Each decomposition level may have the same number of coefficients.

For each decomposition level determined for thresholding, the method may comprise comparing each coefficient with a threshold, and selectively changing a value of the coefficient based on the comparison thereby generating a first modified first wavelet component having changed coefficients and unchanged coefficients for a decomposition level.

The method may further comprise positioning one or more windows on the first modified first wavelet component for a highest decomposition level determined for thresholding. The positions of the windows may be based on evaluating the changed coefficients and unchanged coefficients in the first modified first wavelet component for the highest decomposition level. Once positioned, the method may further comprise changing coefficients in the first modified first wavelet component for the highest decomposition level to its original value when the coefficients are within the one or more windows while keeping the coefficients outside the one or more windows the same as in the first modified first wavelet component to generate a second modified first wavelet component for the highest decomposition level.

The method may further comprise positioning the one or more windows on the first modified first wavelet component for a subset of other decomposition levels of the plurality of decomposition levels at the same positions and changing coefficients in the first modified first wavelet component for each of the subset of other decomposition levels to its original value when the coefficients are within the one or more windows while keeping the coefficients outside the one or more windows the same as the first modified first wavelet component to generate a third modified first wavelet component, respectively, for each decomposition level of the subset of other decomposition levels.

The method may further comprise transforming, using an inverse undecimated discrete wavelet transformation, the first modified first wavelet component for decomposition levels other than the subset of other decomposition levels and the highest composition level, respectively, the second modified first wavelet component for the highest decomposition level determined for thresholding and the third modified first wavelet component for the subset of other decomposition levels, respectively, into a denoised signal.

Also disclosed is a method of denoising a signal which may comprise transforming a signal using an undecimated discrete wavelet transformation into at least a first wavelet component. The first wavelet component may have a plurality of decomposition levels for thresholding, where each level has a plurality of coefficients. Each decomposition level may have the same number of coefficients.

The method may further comprise positioning one or more windows on the first wavelet component for a highest decomposition level determined for thresholding.

Once positioned, the method may further comprise for the highest decomposition level determined for thresholding, comparing each coefficient of the plurality of coefficients outside the one or more windows with a threshold, and selectively changing a value of the coefficient based on the comparison thereby generating a first modified first wavelet component having changed coefficients and unchanged coefficients for the highest decomposition level.

The method may further comprise positioning the one or more windows on the first wavelet component for a subset of other decomposition levels of the plurality of decomposition levels at the same positions; and for the subset of other decomposition levels of the plurality of decomposition levels, comparing each coefficient of the plurality of coefficients outside the one or more windows with a threshold, and selectively changing a value of the coefficient based on the comparison thereby generating a second modified first wavelet component having changed coefficients and unchanged coefficients, respectively for each decomposition level of the subset of other decomposition levels.

The method may further comprise for the remaining decomposition levels of the plurality of decomposition levels less than the highest decomposition level determined for thresholding, comparing each coefficient of the plurality of coefficients with a threshold and selectively changing a value of the coefficient based on the comparison thereby generating a third modified first wavelet component having changed coefficients and unchanged coefficients, respectively for each decomposition level of the remaining decomposition levels.

The method may further comprise transforming, using an inverse undecimated discrete wavelet transformation, the first modified first wavelet component for the highest decomposition level, the second modified first wavelet component for each decomposition level of the subset of other decomposition levels, respectively, and the third modified first wavelet component for the remaining decomposition levels, respectively, into a denoised signal.

In an aspect of the disclosure, the signal may be further transformed in a second wavelet component via the undecimated discrete wavelet transformation. The second wavelet component may have a plurality of decomposition levels. Each decomposition level also having the same number of coefficients.

For the highest decomposition level, the method may further comprise comparing each coefficient in the second wavelet component with a second threshold, and selectively changing a value of the coefficient based on the comparison, thereby generating a first modified second wavelet component having changed coefficients and unchanged coefficients, positioning one or more windows on the first modified second wavelet component for a highest decomposition level of the plurality of decomposition levels, by evaluating the changed coefficients and unchanged coefficients in the first modified second wavelet component for the highest decomposition level of the plurality of composition level and changing coefficients in the first modified second wavelet component to its original value when the coefficients are within the one or more windows while keeping the coefficients outside the one or more windows the same as the first modified second wavelet component to generate a second modified second wavelet component. The method may further comprise transforming, using an inverse undecimated discrete wavelet transformation, the first modified first wavelet component for decomposition levels other than the subset of other decomposition levels, respectively, the second modified first wavelet component for the highest decomposition level, the third modified first wavelet component for the subset of other decomposition levels, respectively, and the second modified second wavelet component, into the denoised signal.

In an aspect of the disclosure, the position of the windows on the second wavelet component may be the same or different than the position of the windows on the first wavelet component.

Also disclosed is a method which may comprise reversing in time, a signal and transforming the time reversed signal using an undecimated discrete wavelet transformation into at least a first wavelet component. The first wavelet component may have a plurality of decomposition level, each with a plurality of coefficients. Each decomposition level may have the same number of coefficients.

For each decomposition level, the method may further comprise dividing coefficients for the first wavelet component into a first-subset of coefficients and a second-subset of coefficients based on a determined signal to noise ratio of the signal.

For each decomposition level determined for thresholding for the first-subset of coefficient and the second-subset of coefficients, the method may further comprise comparing each coefficient in the first-subset of coefficients with a first threshold, and selectively changing a value of the coefficient in the first-subset of coefficients based on the comparison thereby generating a first modified first subset of coefficients having changed coefficients and unchanged coefficients; and comparing each coefficient in the second-subset of coefficients with a second threshold, and selectively changing a value of the coefficient in the second-subset of coefficients based on the comparison thereby generating a first modified second subset of coefficients having changed coefficients and unchanged coefficients.

The method may further comprise positioning one or more windows on the first modified first subset of coefficients and the first modified second subset of coefficients for a highest decomposition level determined for thresholding, by evaluating the changed coefficients and unchanged coefficients in the first modified first subset of coefficients and the first modified second subset of coefficients, respectively, for the highest decomposition level, respectively, and changing coefficients in the first modified first subset of coefficients and the first modified second subset of coefficients for the respective highest decomposition level to its original value when the coefficients are within the one or more windows while keeping the coefficients outside the one or more windows the same as in the first modified first subset of coefficients and the first modified second subset of coefficients, respectively, to generate a second modified first subset of coefficients and a second modified second subset of coefficients, respectively, for the respective highest decomposition level.

The method may further comprise changing coefficients in the first modified first subset of coefficients and the first modified second subset of coefficients for each of the subset of other decomposition levels to its original value when the coefficients are within the one or more windows while keeping the coefficients outside the one or more windows the same as the first modified first subset of coefficients and the first modified second subset of coefficients, respectively, to generate a third modified first subset of coefficients and a third modified second subset of coefficients, respectively, for a decomposition level of the subset of other decomposition levels.

The method may further comprise transforming, using an inverse undecimated discrete wavelet transformation, the first modified first subset of coefficients and the first modified second subset of coefficients for decomposition levels other than the subset of other decomposition levels and the highest decomposition level, respectively, the second modified first subset of coefficients and the second modified second subset of coefficients for the highest decomposition level, respectively, and the third modified first subset of coefficients and the third modified second subset of coefficients for the subset of other decomposition levels, respectively, into a reversed in time denoised signal; and reversing in time the reversed in time denoised signal to generate a denoised signal.

Also disclosed is a method of denoising a signal which may comprise reversing in time, a signal and transforming the time reversed signal using an undecimated discrete wavelet transformation into at least a first wavelet component. The first wavelet component may have a plurality of decomposition level, each having a plurality of coefficients. The number of coefficients in each level are the same. The method may further comprises, for each decomposition level, dividing coefficients for the first wavelet component into a first-subset of coefficients and a second-subset of coefficients based on a determined signal to noise ratio of the signal.

The method may further comprise positioning one or more windows on the first-subset of coefficients and the second-subset of coefficients for a highest decomposition level determined for thresholding for the first-subset of coefficients and the second-subset of coefficients and for the highest decomposition level determined for thresholding for the first-subset of coefficients and the second-subset of coefficients, comparing each coefficient outside the one or more windows in the first-subset of coefficients with a threshold, and selectively changing a value of the coefficient based on the comparison thereby generating a first modified first wavelet coefficients having changed coefficients and unchanged coefficients for the highest decomposition level and comparing each coefficient outside the one or more windows in the second-subset of coefficients with a second threshold and selectively changing a value of the coefficient based on the comparison thereby generating a first modified second wavelet component having changed coefficients and unchanged coefficients for the highest decomposition level determined for thresholding, respectively. The method may further comprise positioning the one or more windows on the first subset of coefficients for a subset of other decomposition levels of the plurality of decomposition levels at the same positions and changing coefficients in the first-subset of coefficients for each of the subset of other decomposition levels when the coefficients are outside the windows and based on a comparison with a threshold, respectively, to generate a second modified first subset of coefficients having changed coefficients and unchanged coefficients, respectively, for a decomposition level of the subset of other decomposition levels.

The method may further comprise, for the remaining decomposition levels of the plurality of decomposition levels lower than the highest decomposition level determined for thresholding, comparing each coefficient in the first-subset of coefficients with a threshold and selectively changing a value of the coefficient based on the comparison thereby generating a third modified first wavelet coefficients having changed coefficients and unchanged coefficients, respectively for each decomposition level of the remaining decomposition levels.

The method may further comprise transforming, using an inverse undecimated discrete wavelet transformation, a first modified first wavelet coefficients and first modified second wavelet coefficients for the highest decomposition level, a second modified first subset of coefficients, respectively, and the third modified first wavelet coefficients, respectively, into a reversed in time denoised signal; and reversing in time the reversed in time denoised signal to generate a denoised signal.

In an aspect of the disclosure, the above methods may further comprise determining a number of decomposition levels for thresholding. The determination may be based on coefficients in the first wavelet component or coefficients obtained by a transformation via a deiminated discrete wavelet transformation. The number of decomposition levels may be different for the first-subset of coefficients and the second-subset of coefficients.

In an aspect of the disclosure, the position of each window may be such that the ends are where a value of the coefficients change from non-zero to zero and vice versa.

In an aspect of the disclosure, the subset of other composition levels does not include decomposition levels having coefficients only containing noise.

In an aspect of the disclosure, the any of the methods may denoise a signal having an SNR as low as 0.5.

The signal may be an audio signal and/or a video signal. The signal may be streamed over a network. The network comprises at least one source server storing the signal, one or more relay nodes and a user terminal. A source server may comprise a processor configured to execute one or more of the methods of denoising a signal.

The signal may be acquired using a sensor. The sensor may be acceleration sensors, gyroscopes, seismometers, electrodes, light detectors and receivers. The result of the denoising, e.g., denoised signal, may be used as a control feedback for the acquisition of additional signals.

The signal may also be acquired from spectroscopy device(s) or systems.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 2b depicts a diagram of the denoising method depicted in FIG. 2a;

FIG. 6b depicts a diagram of the denoising method depicted in FIG. 6a;

FIG. 7b depicts a diagram of the denoising method depicted in FIG. 7a;

FIG. 8b depicts a diagram of the denoising method depicted in FIG. 8a;

FIG. 9 depicts a block diagram of an example system for denoising signals in accordance with aspects of the disclosure;

FIG. 10 depicts a block diagram of another example of a system for denoising signals in accordance with aspects of the disclosure;

FIGS. 11a1-11a6 depict the coefficients for the Detail components after UDWT and prior to noise thresholding for six decomposition levels, FIGS. 11b1-11b6 depict the coefficients for the Detail components after noise thresholding, FIGS. 11c1-11c6 depict the coefficients for the Detail components after signal location windowing, FIGS. 11d1-11d6 depict the coefficients generated from the reference signal using UDWT, FIG. 11e depicts the input signal generated from the average of 16 scans (noisy), FIG. 11f depicts the denoised signal and FIG. 11g depicts the reference signal;

FIG. 12a depicts the coefficients after windowing for the decomposition level 6 for the Detail component (same as FIG. 11c6), FIG. 12b depicts the coefficients for decomposition level 6 for the Approximation component before thresholding, FIG. 12c depicts the coefficients for the Approximation component after signal location windowing and FIG. 12d depicts the Approximation component of the reference signal at decomposition level 6;

FIG. 13a-FIG. 14c8 depict a comparison of coefficients for different translations, where FIG. 13a depicts the input signal in the wavelet domain and FIG. 14b1-c8 compares coefficients for the Detail components subject to DWT verses UDWT for eight decomposition levels and FIG. 14a depicts the input signal generated from averaging 16 scans in the wavelet domain;

FIG. 15a depicts a noisy signal averaged from 16 scans and the corresponding denoised signal, FIG. 15b depicts a comparison of the denoised signal (from the 16 scans) and the reference signal, FIG. 15c depicts a noisy signal averaged from 4 scans and the corresponding denoised signal, and FIG. 15d depicts a comparison of the denoised signal (from the 4 scans) and the reference signal;

FIG. 16 depicts a table (Table 1) of results showing SNR and SSIM for noisy signals generated from the average 16 scans and 4 scans, respectively and SNR and SSIM for peaks therein and SSIM for denoised signals from different methods;

FIGS. 17a-22b depict results for denoising noisy signals generated from an average of 16 scans and 4 scans using the method described in FIGS. 2a/2b in accordance with aspects of the disclosure and results from the method described in FIGS. 1a/1b of U.S. Pat. No. 10,891,719, where FIG. 17a depicts a noisy signal generated from the average of 16 scans superposed with a corresponding denoised signal in accordance with aspects of the disclosure, FIG. 17b depicts a comparison of the denoised signal with the reference signal;

FIG. 17c depicts the same noisy signal and a corresponding denoised signal denoised in accordance with FIGS. 1a/1b of U.S. Pat. No. 10,891,719, FIG. 17d depicts a comparison of the denoised signal with the same reference signal, FIG. 18a depicts a noisy signal averaged from 4 scans and the corresponding denoised signal in accordance with aspects of the disclosure, FIG. 18b depicts a comparison of the denoised signal (from the 4 scans) and the reference signal, FIG. 18c depicts same noisy signal (from an average of 4 scans) and a corresponding denoised signal denoised in accordance with FIGS. 1a/1b of U.S. Pat. No. 10,891,719, FIG. 17d depicts a comparison of the denoised signal with the same reference signal, FIG. 19a depicts a comparison of weak peaks in the signal averaged from 16 scans obtained from denoising in accordance with aspects of the disclosure and the reference signal, FIG. 19b depicts a comparison of the same peaks in the signal obtained from denoising in accordance with FIGS. 1a/1b of U.S. Pat. No. 10,891,719, FIG. 20a depicts a comparison of weak peaks in the signal averaged from 4 scans where the peaks are determined from denoising in accordance with aspects of the disclosure and the reference signal, FIG. 20b depicts a comparison of the same peaks in the signal determined from denoising in accordance with FIGS. 1a/1b of U.S. Pat. No. 10,891,719 and the reference signal, FIG. 21a depicts a comparison of strong peaks in the signal averaged from 16 scans obtained from denoising in accordance with aspects of the disclosure and the reference signal and FIG. 21b depicts a comparison of the same peaks in the signal obtained from denoising in accordance with FIGS. 1a/1b of U.S. Pat. No. 10,891,719 and the reference signal, FIG. 22a depicts a comparison of strong peaks in the signal averaged from 4 scans obtained from denoising in accordance with aspects of the disclosure and the reference signal and FIG. 22b depicts a comparison of the same peaks in the signal obtained from denoising in accordance with FIGS. 1a/1b of U.S. Pat. No. 10,891,719 and the reference signal;

FIG. 23a depicts a noisy signal generated by averaging 4 scans and the corresponding denoised signal which was denoised using UDWT and signal location windows (and windowing), FIG. 23b depicts a portion of the denoised signal of FIG. 23a superposed on a portion of the reference signal, FIG. 23c depicts a noisy signal generated by averaging 4 scans and the corresponding denoised signal which was denoised using UDWT without signal location windows (and windowing) and FIG. 23d depicts a portion of the denoised signal of FIG. 23c superposed on a portion of the reference signal;

FIG. 24a depicts a noisy signal generated by averaging 18 scans superposed on a corresponding denoised signal in accordance with aspects of the disclosure, FIG. 24b depicts the same noisy signal superposed on a corresponding denoised signal denoised in accordance with FIGS. 1a/1b of U.S. Pat. No. 10,891,719, FIG. 24c depicts a noisy signal generated by averaging 4 scans superposed on a corresponding denoised signal in accordance with aspects of the disclosure, FIG. 24d depicts the same noisy signal superposed on a corresponding denoised signal denoised in accordance with FIGS. 1a/1b of U.S. Pat. No. 10,891,719, FIG. 24e depicts a noisy signal generated from 1 scan superposed on a corresponding denoised signal in accordance with aspects of the disclosure, FIG. 24f depicts the same noisy signal superposed on a corresponding denoised signal denoised in accordance with FIGS. 1a/1b of U.S. Pat. No. 10,891,719 and FIG. 24g depicts portions of the respective noisy and denoised signals showing peaks 5 and 6;

FIG. 25 depicts a table (Table 2) having the results of Example 2 including SNR and SSIM for the three noisy/denoised signals;

FIG. 26a depicts a noisy signal superposed on its corresponding denoised signal in accordance with aspects of the disclosure, FIG. 26b depicts the same noisy signal superposed on its corresponding denoised signal in accordance with FIGS. 1a/1b of U.S. Pat. No. 10,891,719, FIG. 26c depicts the denoised signal in accordance with aspects of the disclosure, FIG. 26d depicts the denoised signal in accordance with FIGS. 1a/1b of U.S. Pat. No. 10,891,719 and FIGS. 26e and 26f depict the reference signal; and FIG. 27 depicts a table (Table 3) showing the results include the SNR, SSIM and hyperfine lines comparing the different denoising methods and the reference signal.

DETAILED DESCRIPTION

Figure 2A:
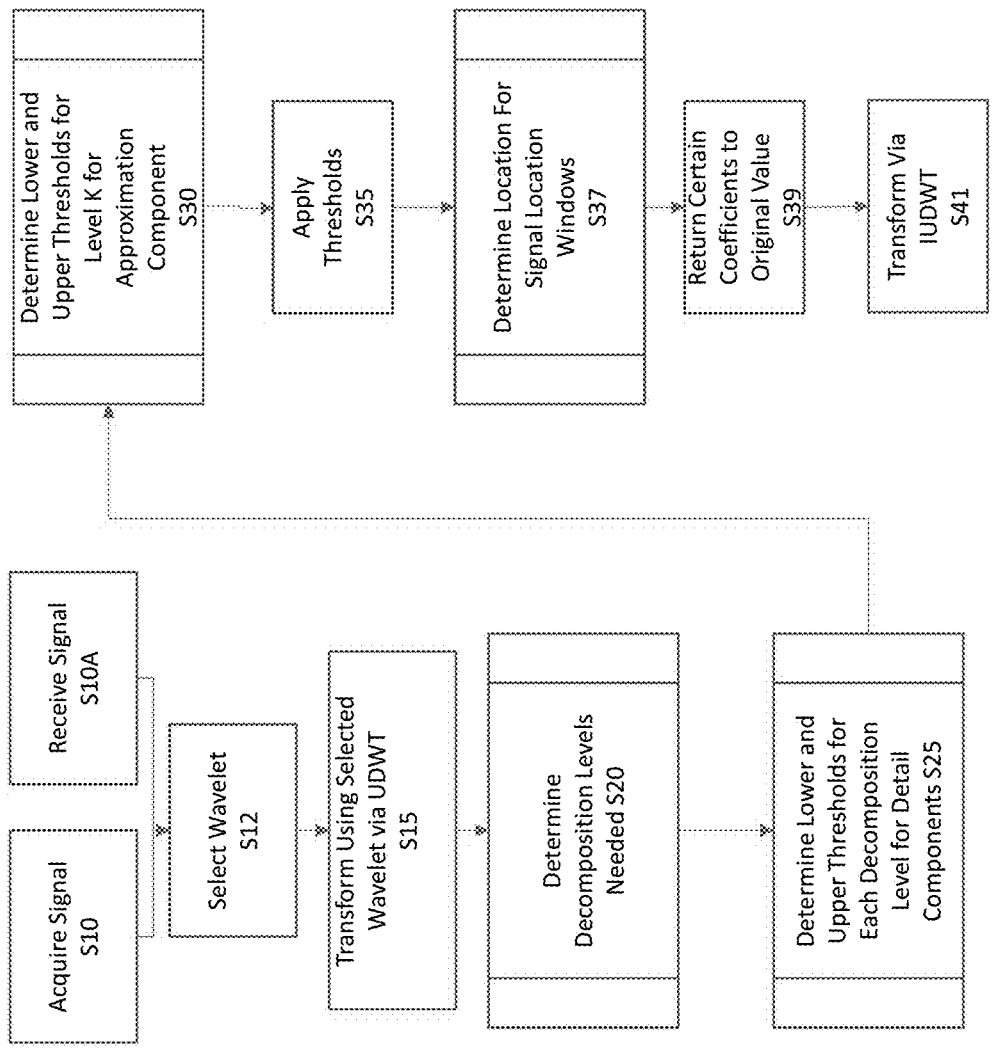
FIG. 2a depicts a flow chart for a method of denoising a signal in accordance with aspects of the disclosure.
Figure 2B:
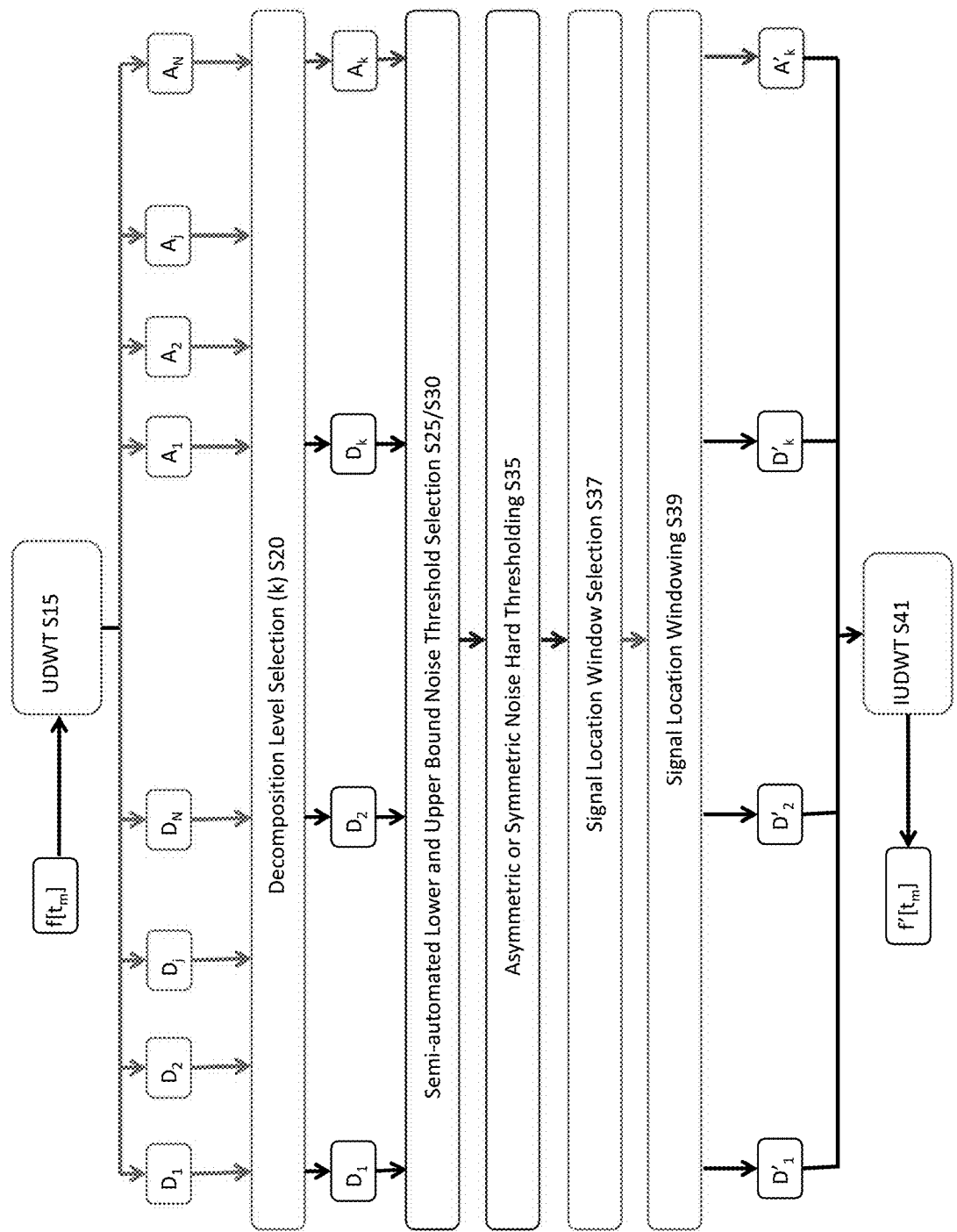

FIG. 2a depicts a flow chart for a method of denoising a signal in accordance with aspects of the disclosure. FIG. 2b depicts a diagram of the method including the Detail and Approximation components full scale, N and post selection decomposition level, k. The maximum number of decomposition levels, N, is defined as $N=\log_2(Signal_{Length})$. For instance, a signal with data length of 128 will have 7 Detail and Approximation components (from 7 decomposition levels). N refers to the lowest frequency sub-band. The dyadic scale (i.e., $s=2^{-j}$) is selected so that the detail components $D_j[n]$ represent non-overlapping frequency bands. In another aspect of the disclosure, the detail components may have small overlapping frequency subbands. However, at decomposition levels 1 to j, only frequency sub-bands represented by them are wavelet-transformed, requiring that the remaining frequency band to reconstruct the original signal also be obtained.

Any of the methods described herein can be used to denoise many different types of signals for many different applications. For example, the signals can be acquired or generated by spectroscopy devices, such as continuous or pulsed Electron Spin Resonance spectroscopy, raman spectroscopy, nuclear magnetic resonance spectroscopy, mass spectroscopy, optical spectroscopy, infrared spectroscopy, laser spectroscopy, single molecule fluorescence spectroscopy and magnetic resonance imaging (spectroscopy). Additionally, the signals can be acquired or generated by microscopy devices such as Electron Spin Resonance Imaging and Microscopy, electron microscopy, including, but not limited to, cryo-electron microscopy (cyro-EM), multiphoton microscopy, confocal microscopy, and Magnetic Resonance Force Microscopy. Further, the signals can be acquired or generated by tomography devices, such as optical coherence tomography, positron emission tomography, and computed tomography. Additionally, the signals can be acquired or generated by other medical devices such as x-ray machines and ultrasounds. Moreover, the signals can be acquired by radar and sonar systems.

Yet additionally, the signals can be acquired by environmental sensors such as wind, gas, temperature, humidity, pressure, radiation levels, and seismometers.

Yet additionally, the signals can be transmitted and received via wired or wireless communication networks and can include audio and/or video.

The denoising methods described herein can be performed by separate standalone devices executing the method or part of a system such as audio/video streaming via a network, image video compression/decompression, power management and distribution, oil and gas exploration, where one or more devices within a system may execute any of the denoising methods described herein.

The signal may be 1-dimensional or multi-dimensional. In a case where the signal is multi-dimensional, the signal may be converted into a series of 1-dimensional signals and each 1-dimensional signal is denoised in accordance with the methods described herein. Once each of the 1-dimensional signals is denoised, the denoised signals may be aggregated to generate a denoised multi-dimensional signal.

At S10, the signal may be acquired either via a sensor or retrieved from memory. In FIG. 2b, the acquired or retrieved signal is identified as $F(t_m)$. The sensor can be a component or components capable of have a response to a condition. For example, the sensor can be, but not limited to, acceleration sensors, gyroscopes, seismometers, electrodes, light detectors and receivers. The light detectors can be a photodiode, photoresistor, photovoltaic, thermopile and photoconductive detector. The sensor may also be an optical sensor. Other sensors may be used.

Alternatively, the signal can be received via a network interface over a communication network S10A. The network interface may be configured for a wired or wireless network. Further, the signal may be input into an application program for processing within the application program. The signal may be input to the application program by another application program in the same or different device.

At S12, the wavelet used for transformation may be selected. There are many different wavelet families that can be selected. For example, the Coiflet, Daubechises and Symlet families are known wavelets. Wavelets that resemble the signal or its properties yield better signal and noise separation as well as sparsity. In an aspect of the disclosure, the wavelet family is chosen such that components, which are coherent, have a large magnitude in a few wavelet coefficients and coefficients occurring at the same location at the different detail components (decomposition levels) are achieved. By contrast, random noise will have many wavelet coefficients with small magnitudes that vary in location at the different detail components.

For example, a continuous wave electron spin resonance may be represented as a blend of function of Gaussian and Lorentzian and thus, a wavelet family suitable for such as spectra may be selected.

Once the signal is either acquired either via a sensor or retrieved from memory (S10) or received via the network (S10A), the signal is transformed using the selected wavelet(s) into both Detail (first set of components or first wavelet component) and Approximation (second set of components or second wavelet component) (S15) by a processor. In some aspects, the processor may be executing the application program.

In accordance with aspects of the disclosure, the processor executes an undecimated discrete wavelet transformation (UDWT). Advantageously, UDWT achieves the maximum signal and noise resolution in the wavelet transform. This means that each Detail and Approximation component has the same length as that of the input signal. Furthermore, UDWT preserves the redundancy in the wavelet domain by keeping all the wavelet coefficients. This provides protection against the noise thresholding procedure. Even if a signal coefficient is removed by noise thresholding, the information can be easily recovered from other (redundant) coefficients, which is not possible in the DWT because each wavelet coefficient represents unique information.

Figure 3:
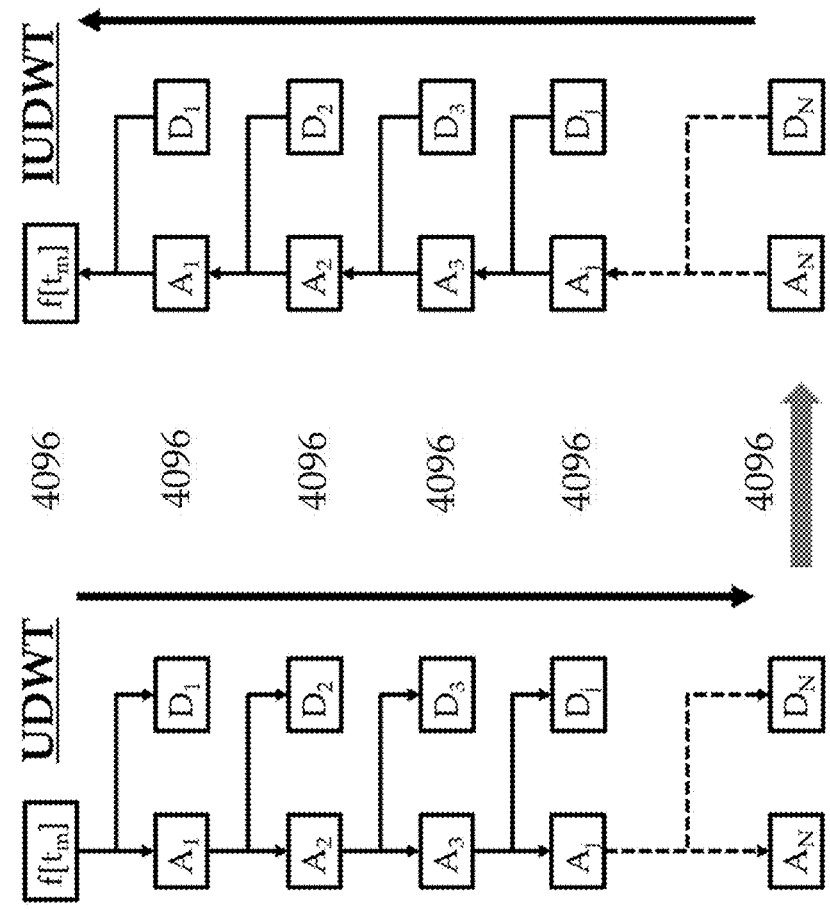
FIG. 3 shows a block diagram of an example of an undecimated discrete wavelet transformation (UDWT) and an inverse discrete wavelet transformation (IUDWT)

As shown in FIG. 3, the number of coefficients in each decomposition level are the same. For example, the number of coefficients may be 4096. $f[t_m]$ is the discrete input signal, and $D_j$ and $A_j$ are the Detail and Approximation components, respectively, at decomposition level j. Also as shown in FIG. 3, the same number of coefficients are in the input signal as the decomposition levels.

In an aspect of the disclosure, a fast UDWT is employed that uses low and high pass filters to replace scaling and wavelet functions, respectively, in order to obtain the Approximation and Detail components. The approximation and detail components may be obtained using the following:

$$A_{j+1}[n]=\Sigma_{i=0}^{L-1}l[i]A_j[i+n] \quad (3)$$

$$D[n]=\Sigma_{i=0}^{L-1}h[i]D_j[i+n] \quad (4)$$

where l[i] and h[i] are low and high pass signal decomposition filters, respectively, and L is the length of both the filters (and also the scaling and wavelet functions). The filter values are the coefficient values of the scaling and wavelet functions.

As can be seen from equations 3 and 4, the low and high pass filters are recursively applied on the Approximation component to obtain the Approximation and Detail components, respectively, at the subsequent level. For decomposition level 1, the input signal is the Approximation component at the $0^{th}$ level.

For successful noise thresholding in the wavelet domain, all the Detail components and the highest decomposition Approximation component that contain noise need to be identified. This is accomplished by selecting the maximum decomposition level k where noise is still present, keeping Detail components from 1 to k and the $k^{th}$ Approximation component. Inaccurate selections of k result in either incomplete noise removal or signal distortion.

At S20, the number of decomposition levels to denoise is determined by the processor. In some aspects of the disclosure, the number of decomposition levels to denoise may be objectively determined. For example, in some aspects of the disclosure, a peak-to-sum ratio S may be used to distinguish between noisy and noise-free detail components for a specific level. The peak-to-sum ratio S (sparsity) may be calculated using coefficients for each decomposition level for the Detail component determined by equations 3 and 4 (undecimated coefficients). The peak-to sum ratio S is calculated using the following:

$$S_j = \frac{\max(|D_j|)}{\sum_{n=1}^{qi}|D_j[n]|} \quad (5)$$

where $S_j$ reflects the sparsity of a detail component and allows the identification of noise presence in a detail component and $q_i$ is the length of the Detail component, $D_j$ refers to the coefficients values for a given decomposition level. $S_j$ will have smaller values for noisy Detail components compared to virtually noise-free Detail components. A large $S_j$ indicates signal presence with only a few large coefficient values, where a small $S_j$ reveals noise presence with a large number of small coefficient value.

The $S_j$ can be categorized.

$S_j \leq 0.01$ indicates Detail components that only contain noise coefficients;

$0.01 \leq S_j \leq 0.1$ indicates Detail components that mainly contain noise with very few high magnitude signal coefficients;

$0.1 \leq S_j \leq T_r$ indicates Detail components dominated by signal coefficients with noise coefficients having small magnitudes; and $S_j \geq T_r$ indicates Detail components that only contain signal coefficients, e.g., noise is no longer distinguishable.

$T_r$ will be referred to herein as the decomposition threshold. The Sj for a specific decomposition level increases as the number of decomposition levels increases. The number of decomposition levels is selected such that the detail components only contain signal coefficients and where the noise is no longer distinguishable.

$$S_j < T_r, S_{j+1} > T_r, \text{ when } k=j, \quad (6)$$

where k is the maximum number of decomposition levels needed.

$T_r$ is used to distinguish between Detail components dominated by signal coefficients with noise coefficients having small magnitudes and detail components only containing signal coefficients. In an aspect of the disclosure $T_r$ is selected to be approximately 0.2.

In other aspects of the disclosure, the Sj may be determined using coefficients from a decimated DWT. The coefficients for the Detail component using a decimated DWT may be calculated as follows:

$$D_j[n]=\Sigma_{m=0}^{P-1}f[t_m]2^{j/2}\psi[2^j t_m-n] \quad (7)$$

where with j and n integers, $t_m$ is the discretized time, $f[t_m]$ is the discretized input signal, p=length($f[t_m]$), and $D_j[n]$ is the detail component of $f[t_m]$ a.

Figure 4:
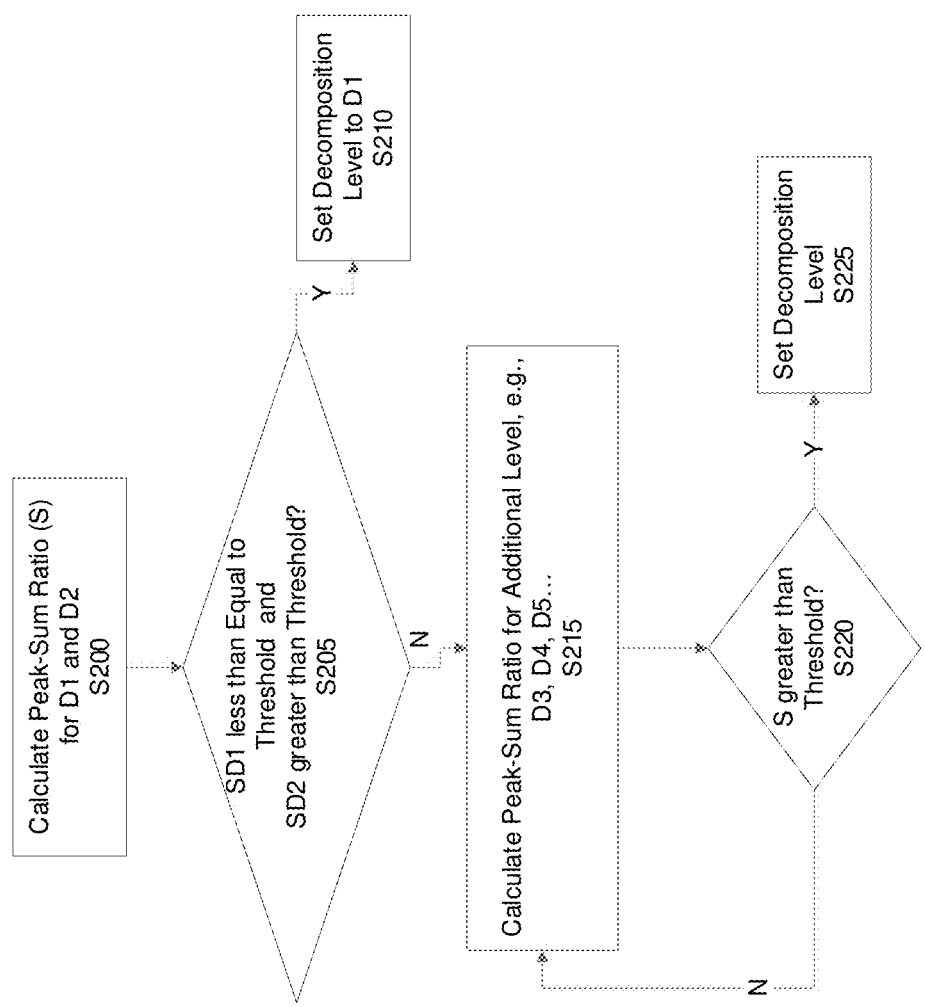
FIG. 4 depicts one example of how the number decomposition levels (k) is determined in accordance with aspects of the disclosure.

FIG. 4 depicts one example of how the number decomposition levels (k) is determined. As can be seen from equation 6, Sj must be calculated for at least two decomposition levels.

At S200, the peak-to-sum ratio may be calculated by a processor for the first two levels, e.g., D1 and D2 using equation 5 (D1 refers to decomposition level 1 for the Detail component and D2 refers to decomposition level 2 for the Detail component. At S205, the processor determines if equation 6 is satisfied for D1 and D2, where D1 is j and D2 is j+1. If at S205, the processor determines that equation 6 is satisfied ("Y"), the processor sets the decomposition level needed for denoising to 1, e.g., k=1, otherwise, the calculation is repeated for an additional level at S215. At S220, the processor compares the calculated peak-to-sum ratio for the additional level with $T_r$. If the peak-to-sum ratio for the additional level is still less ("N"), S215 and S220 are repeated by the processor until the peak-to-sum ratio is greater than the $T_r$ for a given decomposition level as shown in equation 6. If the peak-to-sum ratio for a given deposition level is greater than $T_r$ (this become the j+1 level) ("Y" at S220), the processor sets the decomposition level k as one level less than the decomposition level for which the last peak-to sum ratio was calculated at S225. The set decomposition level k is stored in memory. The Detail components in the set decomposition level k, i.e., $D_1$-$D_k$ are shown in FIG. 2b as being output of S20. $A_k$ is also output.

In other aspects of the disclosure, other relationships between the coefficients in the Detail components may be used to determine the number of decomposition levels.

In another aspect of the disclosure, instead of the automated process for determining the decomposition levels k, as depicted in FIG. 4, a user may visually inspect the Detail component(s) and the corresponding Approximation components. For example, $D_1$-$D_N$ and $A_1$-$A_N$ may be displayed side-by-side on a display. A user may select the Detail components ($D_{1-k}$) to be denoised by including the decomposition levels until a level is reached in which noise is almost visible indistinguishable from the signal. The location and magnitude of signal and noise in the wavelet component are also useful, especially in identifying systematic noise. In all of the Detail components, signals occur in the same locations with large magnitudes, whereas random noise appears inconsistently with small magnitudes and systematic noise usually occurs at a specific location with low magnitude. The amount of noise present in Detail components reduce from decomposition level 1 to decomposition level N because noise usually contains more high frequencies than low frequencies. For very low SNR, an initial decomposition level(s), e.g., 1 and 2 may contain just noise, whereas for high SNR, the last decomposition level may only contain signal.

At S25, the processor may determine the denoise thresholds for each decomposition level used when thresholding the detailed components. For each level, there may be two thresholds: a lower threshold and an upper threshold. In an aspect of the disclosure, the lower threshold may be used for negative coefficients and the upper threshold may be used for positive coefficients.

For some inputs, the presence of signal and noise coefficients in the Detail components may have a symmetric distribution. However, for other inputs, the distribution may be symmetric with a non-zero mean. For example, the coefficients of signal, systematic noise and other non-symmetric noise like Poisson noise, may create positive or negative bias in the Detail components and thus result in the non-zero mean. Moreover, even random noise such as Gaussian noise is likely to have coefficient distribution bias.

Therefore, in some aspects, the lower and upper thresholds may be symmetric about zero. In other aspects, the lower and upper thresholds may not be symmetric about zero. The two thresholds may be calculated using the following equations $$\lambda_{j,L}=\mu_j-\kappa_{j,L}\sigma_j \quad (8)$$

$$\lambda_{j,H}=\mu_j-\kappa_{j,H}\sigma_j \quad (9)$$

where $\lambda_{j,L}$ and $\lambda_{j,H}$ are the lower threshold and upper threshold, respectively, for the Detail component at the $j^{th}$ Decomposition level, $\mu_j$ and $\sigma_j$ are the mean and standard deviation, respectively of the Detail component at the $j^{th}$ Decomposition level, and $\kappa_{j,L}$ and $\kappa_{j,H}$ are adjustable parameters to obtain optimal thresholds, respectively for the positive and negative coefficients to remove noise. Selecting the upper and lower thresholds may impact the performance of the denoising.

Figure 5:
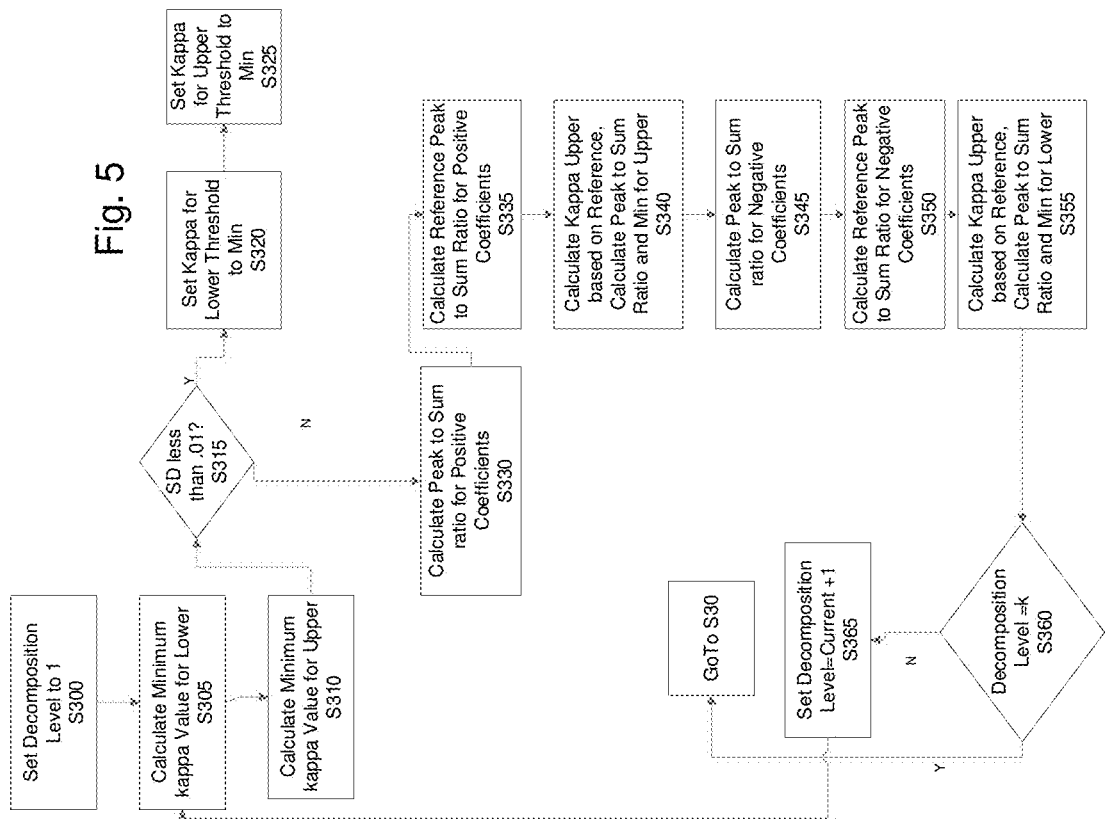
FIG. 5 depicts a flow chart for an example of a method of determining the lower threshold and the upper threshold in accordance with aspects of the disclosure.

FIG. 5 depicts a flow chart for an example of a method of determining the lower threshold and the upper threshold in accordance with aspects of the disclosure. As noted above, the thresholds are determined for each decomposition level, k determined to be used for thresholding, e.g., 1–k. In an aspect of the disclosure, the thresholds may be determined, one level at a time, starting with decomposition level 1. Thus, at S300, the processor may set the level for analysis, e.g., level 1. The processor may use a counter to count the decomposition levels. The thresholds are stored in memory for each decomposition level used for thresholding. The setting of the level may also include setting a memory location to store the associated thresholds Minimum $\kappa_{j,Lmin}$ and $\kappa_{j,Hmin}$ are respectively determined by the processor at S305 and S310. $\kappa_{j,Lmin}$ and $\kappa_{j,Hmin}$ are the minimum values that cover all of the coefficients in a given decomposition level.

$\kappa_{j,Lmin}$ may be determined by the following equations:

$$\kappa_{j,L_{min}} = \frac{\mu_j - \max(|D_j<0|)}{\sigma_j} \quad (10)$$

$\kappa_{j,Hmin}$ may be determined by the following equations:

$$\kappa_{j,H_{min}} = \frac{\max(|D_j>0|-\mu_j)}{\sigma_j} \quad (11)$$

As previously described, when a peak-to-sum value S for a given decomposition level is less than 0.01, the component only contains noise coefficients and thus all coefficient of the Detail component can be assigned to zero. Therefore, at S315, the processor compares the previously calculated peak-to-sum value with 0.01. If the peak-to-sum value S≤0.01, then the processor may set $\kappa_{j,L}=\kappa_{j,Lmin}$ at S320 and sets $\kappa_{j,H}=\kappa_{j,Hmin}$ S325. The $\lambda_{j,L}$ in turn would be calculated using equation 8 and $\lambda_{j,H}$ would be calculated using equation 9.

If the peak-to-sum value is greater than 0.01, both signal and noise coefficients are present. Accordingly, the minimum κ values for both the lower and the upper threshold must be scaled given that the magnitude of the noise coefficients are less than that of the signal coefficients, e.g., $\kappa_{j,L}<\kappa_{j,Lmin}$ and $\kappa_{j,H}<\kappa_{j,Hmin}$.

In an aspect of the disclosure, the processor separately calculates the peak-to-sum ratios for both the positive coefficients (S330) and the negative coefficients (S345).

The peak-to-sum for the negative coefficients $S_j$, L may be determined using the following equation $$S_{j,L} = \frac{\max(|D_j<0|)}{\sum_{n=1}^{qi}|D_j[n]|<0|} \quad (12)$$

The denominator in equation 12 adds the absolute value of all of the negative coefficients in a given decomposition level.

The peak-to-sum for the positive coefficients $S_{j,H}$ may be determined using the following equation $$S_{j,H} = \frac{\max(|D_j \geq 0|)}{\sum_{n=1}^{qi} |D_j[n] \geq 0|} \quad (13)$$

The denominator in equation 13 adds the absolute value of all of the positive coefficients in a given decomposition level.

The processor may also separately calculate reference peak-to-sum ratios for both the positive coefficients (S335) and the negative coefficients (S350). The reference peak-to-sum ratio uses peak-to-sum ratios from both a decomposition level one greater than the determined decomposition level, k, (i.e., k+1) as well as the determined decomposition level, k. For example, if k=5, the reference peak-to-sum ratio is determined from peak-to-sum values for the $5^{th}$ and $6^{th}$ decomposition levels.

The upper reference peak-to-sum ratio $S_{r,H}$ may be determined by the processor using the following equation at S335:

$$S_{r,H} = (S_{k,H} + S_{k+1,H})/2 \quad (14)$$

The lower reference peak-to-sum ratio $S_{r,L}$ may be determined by the processor using the following equation at S350:

$$S_{r,L} = (S_{k,L} + S_{k+1,L})/2 \quad (15)$$

At S340 and S355, the processor may separately calculate $\kappa_{j,L}$ and $\kappa_{j,H}$ using the following equations:

$$\kappa_{j,L} = \left(\frac{S_{r,L} - S_{j,L}}{S_{r,L}}\right) \kappa_{j,L_{min}} \quad (16)$$

$$\kappa_{j,H} = \left(\frac{S_{r,H} - S_{j,H}}{S_{r,H}}\right) \kappa_{j,H_{min}} \quad (17)$$

Once $\kappa_{j,L}$ and $\kappa_{j,H}$ are determined, the processor can use equations 8 and 9 to calculate $\lambda_{j,L}$ and $\lambda_{j,H}$ for a given decomposition level. $\lambda_{j,L}$ and $\lambda_{j,H}$ are then stored in memory.

In an aspect of the disclosure, $\kappa_{j,L}$ and $\kappa_{j,H}$ may also be adjusted to a value different than calculated under certain conditions, if needed. For example, even when $S_j \geq 0.01$, a Detail component(s) may have only noise coefficients due to one or more large random noise spikes, and $\kappa_{j,L_{min}}$ and $\kappa_{j,H_{min}}$ may be used instead of the calculated values from equations 16 and 17. Similarly, in a noise-dominated Detail component(s) either positive or negative coefficients are all noise and $\kappa_{j,L_{min}}$ and $\kappa_{j,H_{min}}$ may be used instead of the calculated values from equations 16 and 17.

Additionally, when small signal and large noise coefficient values are comparable, $\kappa_{j,L}$ and $\kappa_{j,H}$ may be slightly increased or decreased to separate the signal and noise coefficients.

S305-S355 are repeated for each decomposition level used for denoising, i.e., 1–k. Thus, at S300 the processor may determine if the thresholds have been determined for all of the k decomposition levels. In other words, the processor may determine if the decomposition level whose thresholds were calculated is k (the final decomposition level used). If "N", then the processor may increment the decomposition level for processing by 1 (S365) and return to S305 to start the process for the next decomposition level.

If "Y" at S360, the processor may go to S30 to determine the upper threshold and lower threshold for the Approximation component for decomposition level k.

The upper and lower threshold for the Approximation component may be independently determined in the same as described above S305-S355 and will not be described again. However, the determination may be made for only one decomposition level. In Equations 8-11 $\mu_k$ and $\sigma_k$ are the mean and standard deviation for the $k^{th}$ decomposition level for the Approximation component. Equations 12-17 would be determined using the coefficients in the $k^{th}$ decomposition level for the Approximation component. Additionally, for the Approximation component the upper and lower threshold need not be symmetric about zero as it contains a D.C. frequency. Therefore, its lower and upper thresholds can have any value and do not need to represent negative and positive wavelet coefficient values, respectively.

Once all of the thresholds (the lower threshold and the upper threshold for each decomposition level of the Detail components and the upper threshold and lower threshold for the Approximation component) are determined and stored, the processor may execute a thresholding of the components at S35. In an aspect of the disclosure, a hard thresholding may be used. Unlike certain conventional techniques that use soft thresholding, hard thresholding ensure that the signal wavelet coefficients are not distorted by the thresholds, especially when signal and noise coefficients are disjoint and not superimposed. Using the thresholds determined above, noise present at a signal location is separated in the initial decomposition levels and removed.

For the Detail components, the thresholding is done at each of the decomposition levels used to denoise, e.g., 1–k and for the Approximation component, the thresholding is done at the decomposition level k only (unlike conventional techniques which do not threshold the Approximation components). However, certain signals may contain substantial low frequency noise (especially at low SNR) that impedes analysis. Thus, the Approximation component(s) may also contain low frequency noise and may also be denoised.

Depending on the signal properties and the choice of wavelets, the $k^{th}$ Approximation component may represent low frequency noise and signal coefficients in a relatively sparse manner allowing for the noise to be removed. The signal coefficients would have larger values than the noise coefficients. The processor may use the following equation for thresholding Detail coefficients:

$$D'_j[n] = \begin{cases} 0, & \text{for } \lambda_{j,L} \leq D_j[n] \leq \lambda_{j,H} \\ D_j[n] & \text{otherwise} \end{cases} \quad (18)$$

where D'j[n] is the denoised (or noise thresholded) Detail component.

The processor may use the following equation for thresholding Approximation coefficients:

$$A'_k[n] = \begin{cases} a, & \text{for } \lambda_{j,L} \leq A_k[n] \leq \lambda_{j,H} \\ A_k[n] & \text{otherwise} \end{cases} \quad (19)$$

where $A_k[n]$ and $A'_k[n]$ are the noisy and denoised Approximation coefficients, respectively, at the kth decomposition level and a is the constant with which noisy values are replaced. In some aspects, for signals with a baseline centered around zero, a=0. For non-zero baseline signal(s), a is assigned to the baseline value.

At S37, the location(s) or position(s) for respective signal location windows are determined. Signal location windows may be based on the coefficient locations. Coefficients may have both signal and noise. Signal coefficients, for small SNR signals, may have a magnitude smaller than noise coefficients. Although noise coefficients may be larger in magnitude than signal coefficients, signal location windows may be used to recover signal coefficients using location information. This is because the signal occurs at the same location in each decomposition level and therefore, cross-component information may be used to localize where signal coefficients are occurring.

Signal location windows take advantage of the fact that using UDWT achieves a one-to-one correlation between coefficients in the decomposition levels and input.

In an aspect of the disclosure, the location(s) or position(s) for the signal location windows(s) may be subjectively determined.

In an aspect of the disclosure, the location determination is after the thresholding, which removes noise coefficients and signal coefficients whose magnitude is less than a maximum magnitude of noise coefficients. The processor may display the coefficients for the kth decomposition level for the Detail component (maximum decomposition level for thresholding). The coefficients may include both changed and unchanged coefficients. Typically, noise coefficients dominate the signal coefficients are primarily in the initial decomposition levels as this is where noise is heavily present and signal is weak, however, moving towards the maximum decomposition level k, the signal coefficients will become dominant Therefore, the noise thresholding at the kth decomposition level likely will only remove the noise coefficients. if any coefficients. The relative values of the coefficients for the kth decomposition level may be inspected to determine the locations of the signal coefficients. Signal coefficients for the kth decomposition level may be determined by magnitude.

The signal location window(s) are placed or superposed over the signal coefficients identified. The signal location windows may also be placed on the same coefficient locations in other decomposition levels. However, in some aspects of the disclosure, decomposition levels for the Detail components only containing noise coefficients may not have signal location windows positioned or superposed on any of its coefficients. This is because the Detail components at these decomposition levels do not contain signal coefficients in the first place and therefore there is no need to recover signal coefficients for the decomposition levels. In an aspect of the disclosure, if a decomposition level has an $S_j$ value of less than 0.01, the signal location window may not be positioned for the decomposition level. In other aspects, the value (0.01) may be adjusted depending on the type/class of the input signal and the number of data points in the input signal.

In other aspects, the location(s) or position(s) of the signal location window(s) may be objectively placed. Similar to the subjective determination, the objective determination may use the coefficients for the kth decomposition level for the Detail component. In an aspect of the disclosure, the processor may examine the first coefficient for the decomposition level, and if the coefficient is zero, continue examining the coefficients until a non-zero value for a coefficient is discovered. The first non-zero value may form the start of a signal location window. The processor may continue examining coefficients until another zero-value coefficient is discovered. Once another zero value coefficient is discovered, the signal location window is ended. The process may be repeated until all coefficients in the decomposition level for the component are examined. In this manner, signal coefficients will be within a signal location window. More than one signal location window may be positioned on the kth level of the component. Effectively, the processor places one or more signal location windows over all non-zero value coefficients for the kth decomposition level for the Detail component.

The non-zero coefficient values may be defined as:

$$V_{loc} = \{n : \forall D_k[n] \neq 0\} \quad (20)$$

where $V_{loc}$ is the index of all non-zero Detail coefficients of the kth decomposition level.

Like with the subjective determination, location window (s) may also be placed on the same coefficient locations in other decomposition levels. However, in some aspects of the disclosure, decomposition levels for the Detail components only containing noise coefficients may not have signal location windows positioned or superposed on any of its coefficients. This is because the Detail components at these decomposition levels do not contain signal coefficients in the first place and therefore there is no need to recover signal coefficients for the decomposition level. In an aspect of the disclosure, if a decomposition level has an $S_j$ value of less than 0.01, a signal location window may not be positioned for the decomposition level.

In some aspects of the disclosure, the signal location window(s) may be positioned on the coefficients in the Approximation component for the kth decomposition level. Since UDWT is used, the signal locations may be in the same coefficient locations in the Detail component and Approximation component. Therefore, the location(s) of the signal location window(s) for the Approximation component may be the same as the location(s) of the signal location window(s) for the Detail component.

In some aspects, depending on the input signal and the noise thresholding, signal location windows may not be needed for the Approximation component. Also in some aspects, the noise thresholding may be sufficient to denoise the signal without the need for the signal location windows for the Detail components as well.

In some aspects, instead of applying signal location windows to the Detail component first, the location(s) or position(s) for the signal location window(s) may be first determined for the Approximation component at the kth decomposition level and then applied to the Detail component for the kth decomposition level (and subsequently applied to other decomposition levels at the same locations or positions). However, where low frequency noise is substantial, the signal location window(s) should be selected first for the kth decomposition level for the Detail component and then applied to the kth decomposition level for the Approximation component.

In some aspects of the disclosure, the Approximation component may have a wider or narrower signal coefficient location window compared to the Detail component due to baseline or any other low frequency feature. In this aspect of the disclosure, the location(s) or position(s) of the signal location window(s) may be subjectively determined for the kth decomposition level of the Approximation component.

After the signal location windows are applied to the Detail components (for certain decomposition levels), coefficients within the windows are restored to their original values at S39. That is, wavelet coefficients lying within the signal location window are restored as follows:

$$D'_j[n] = \begin{cases} D_j[n], & : \text{if } n \in V_{loc} \\ D'_j[n] & : \text{otherwise} \end{cases} \quad (21)$$

Similarly, in some aspects, where signal location windows are also applied to the kth decomposition level for the Approximation component, coefficients within the windows (in the Approximation component) are also restored to their original values at S39 as follows:

$$A'_k[n] = \begin{cases} A_k[n], & : \text{if } n \in V_{loc} \\ A'_k[n] & : \text{otherwise} \end{cases} \quad (22)$$

By applying the signal location windowing (S37 and S39), low magnitude signal coefficients may be recovered where both signal and noise are present.

FIG. 2b shows the output of S39 being the denoised Detailed components $D'_1$-$D'_k$ and denoised Approximation component $A'_k$.

At S41, the processor may perform an inverse undecimated discrete transformation to recover a denoised signal. The Inverse Undecimated Wavelet Transform (IUDWT) is defined as:

$$A_j[n] = \Sigma_{i=0}^{L-1} \tilde{l}[i] A'_{j+1}[i+n] \Sigma_{i=0}^{L-1} \tilde{h}[i] D'_{j+1}[i+n] \quad (23)$$

In another aspect of the disclosure, prior to S41, the denoised Detail components $D'_1$-$D'_k$ and denoised Approximation component $A'_k$ may be displayed on a display side-by-side. A user may visually compare the denoised components with the corresponding noised components and adjust $\kappa_{j,L}$ and $\kappa_{j,H}$ based on the comparison.

In other aspects of the disclosure, the determination of the location(s) or position(s) of the signal location windows may be performed prior to thresholding (S35). This may be done where the location of the signal (verse noise) is a priori known. For example, a compound or material may be the subject of a previous experiment or study. Another example of this would be occurrence of molecular spectra in nuclear magnetic resonant (NMR) experiments where the magnetic field (x-axis) at which the peak of a particular molecular spectra will occur is sometimes known. Where S37B is executed prior to thresholding, any coefficient within the signal location window is not changed by equation 18 and/or 19 at S35A. In an aspect of the disclosure, the processor may "lock" coefficients within the signal location window(s) from being changed in S39A. For example, in an aspect of the disclosure, the processor may only specify coefficients outside the signal location windows(s) for application of equations 18 and 19 at S39A. In other words, at S35A, the processor may only apply the equations 18 and 19 to coefficients outside the signal location window(s) for the Detail components and the Approximation component, respectively, However, coefficients within the signal location window(s) are still used to determine the lower and upper thresholds at S25 and S30.

Figure 6A:
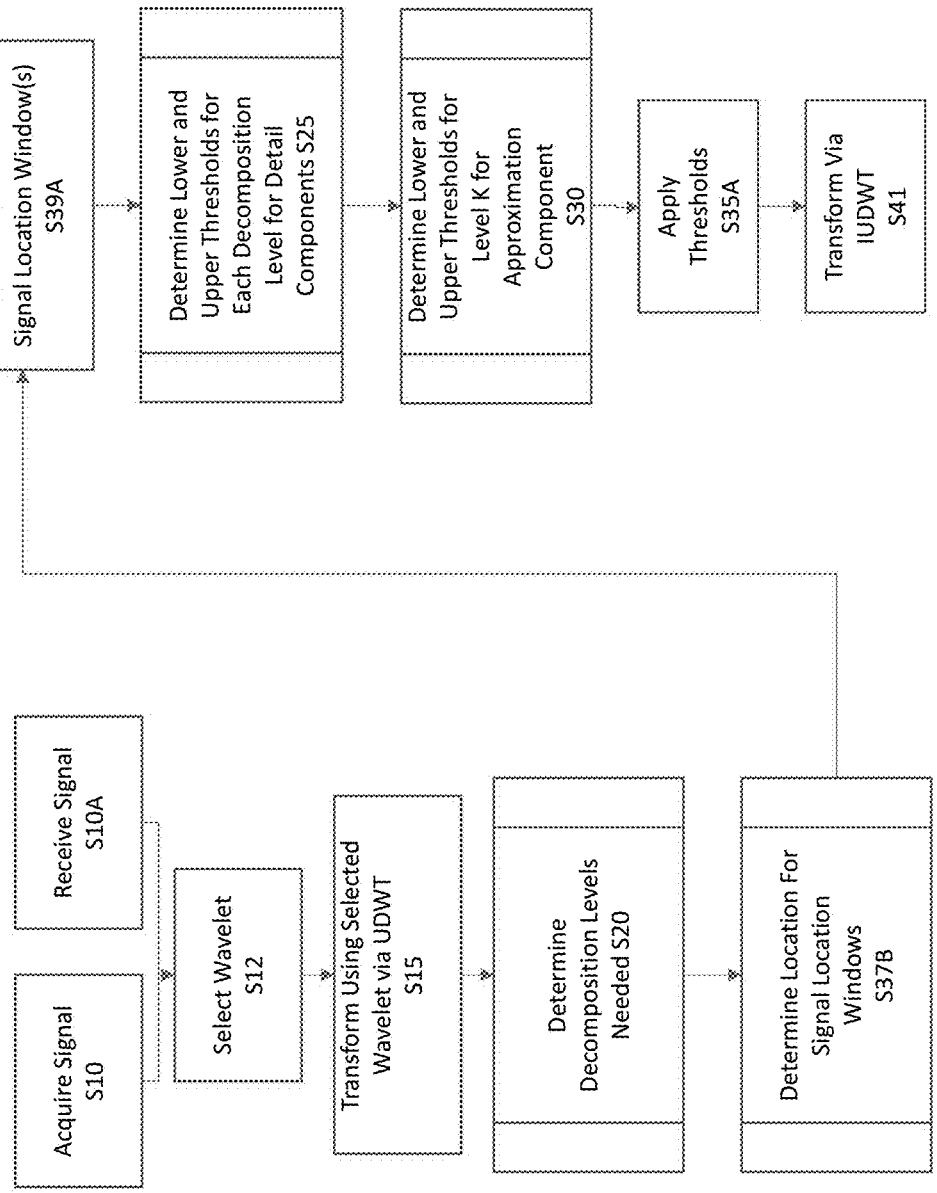
FIG. 6a depicts a flow chart for a method of denoising a signal in accordance with other aspects of the disclosure.
Figure 6B:
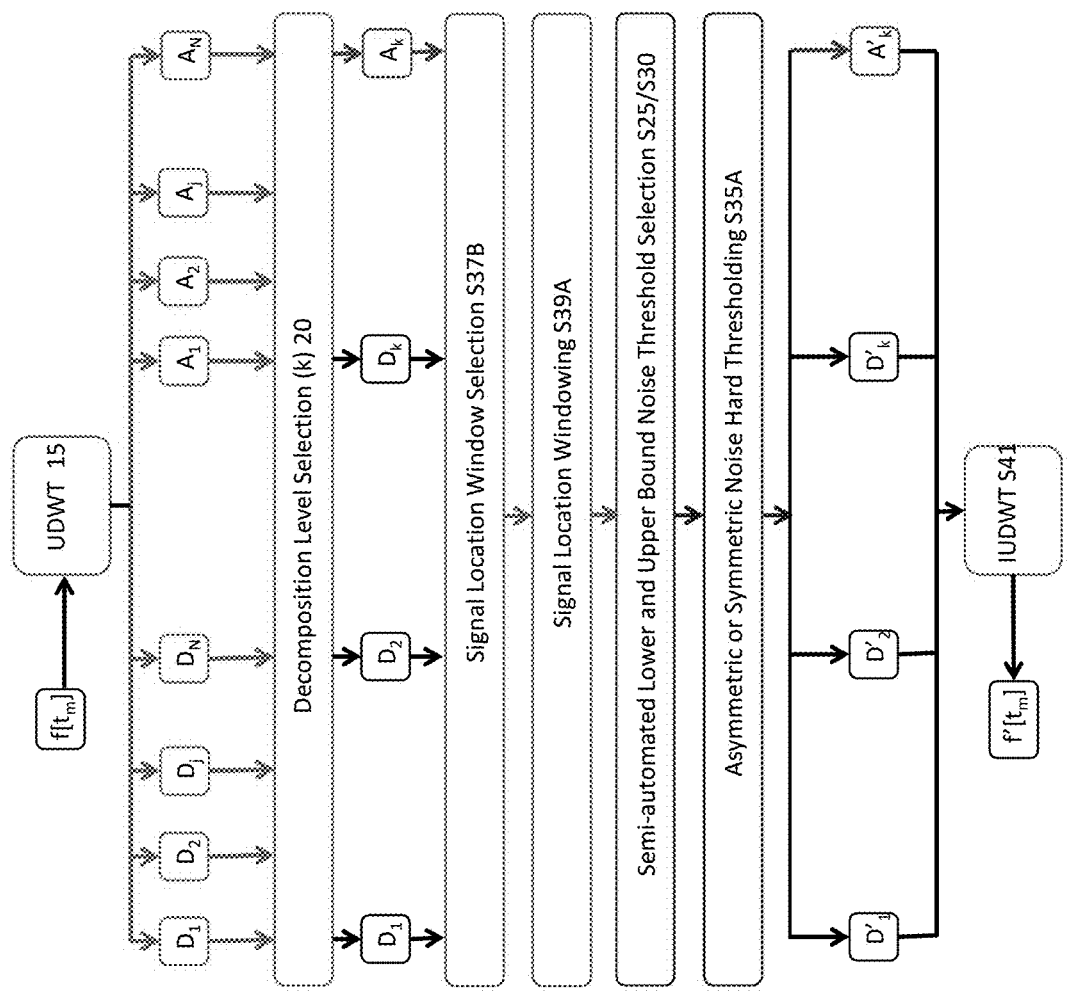

FIGS. 6a and 6b show a method where the determination of the location(s) of the signal location window(s) are performed before thresholding.

In other aspects of the disclosure, S39A may be omitted, and equations 18 and 19 may be modified to reflect the signal location windows as follows:

$$D'_j[n] = \begin{cases} 0, \text{ for } \lambda_{j,L} \leq D_j[n] \leq \lambda_{j,H} \text{ and where } n \text{ is} \\ \text{outside the signal location window}(s) \\ D_j[n] \text{ otherwise} \end{cases} \quad (18A)$$

-continued
$$A'_k[n] = \begin{cases} a, \text{ for } \lambda_{j,L} \leq A_k[n] \leq \lambda_{j,H} \text{ and where } n \text{ is} \\ \text{outside the signal location window}(s) \\ A_k[n] \text{ otherwise} \end{cases} \quad (19A)$$

where D'j[n] is the denoised (or noise thresholded) Detail component.

Therefore, in S35A, the processor only changes the coefficient when both conditions are satisfies, e.g., threshold condition and outside the signal location window(s).

Figure 7A:
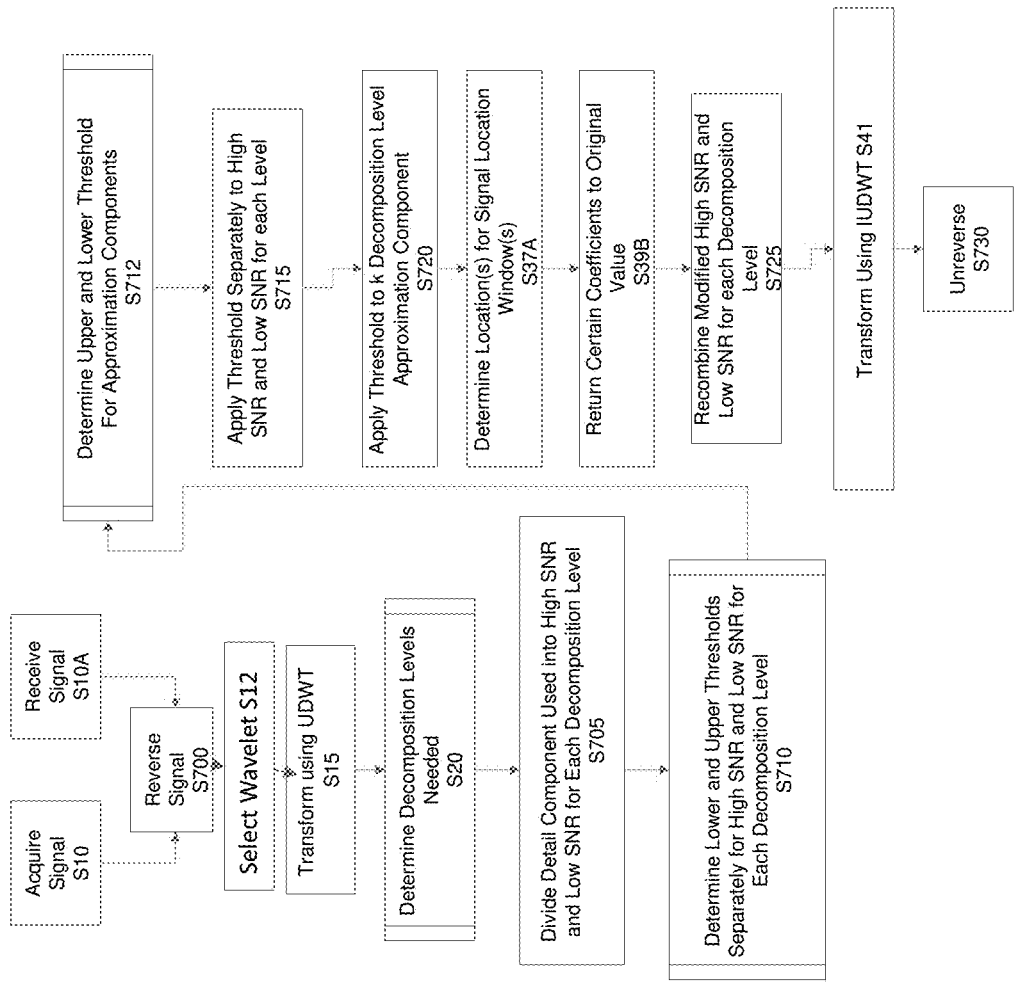
FIG. 7a depicts a flow chart for a method of denoising a signal in accordance with other aspects of the disclosure.
Figure 7B:
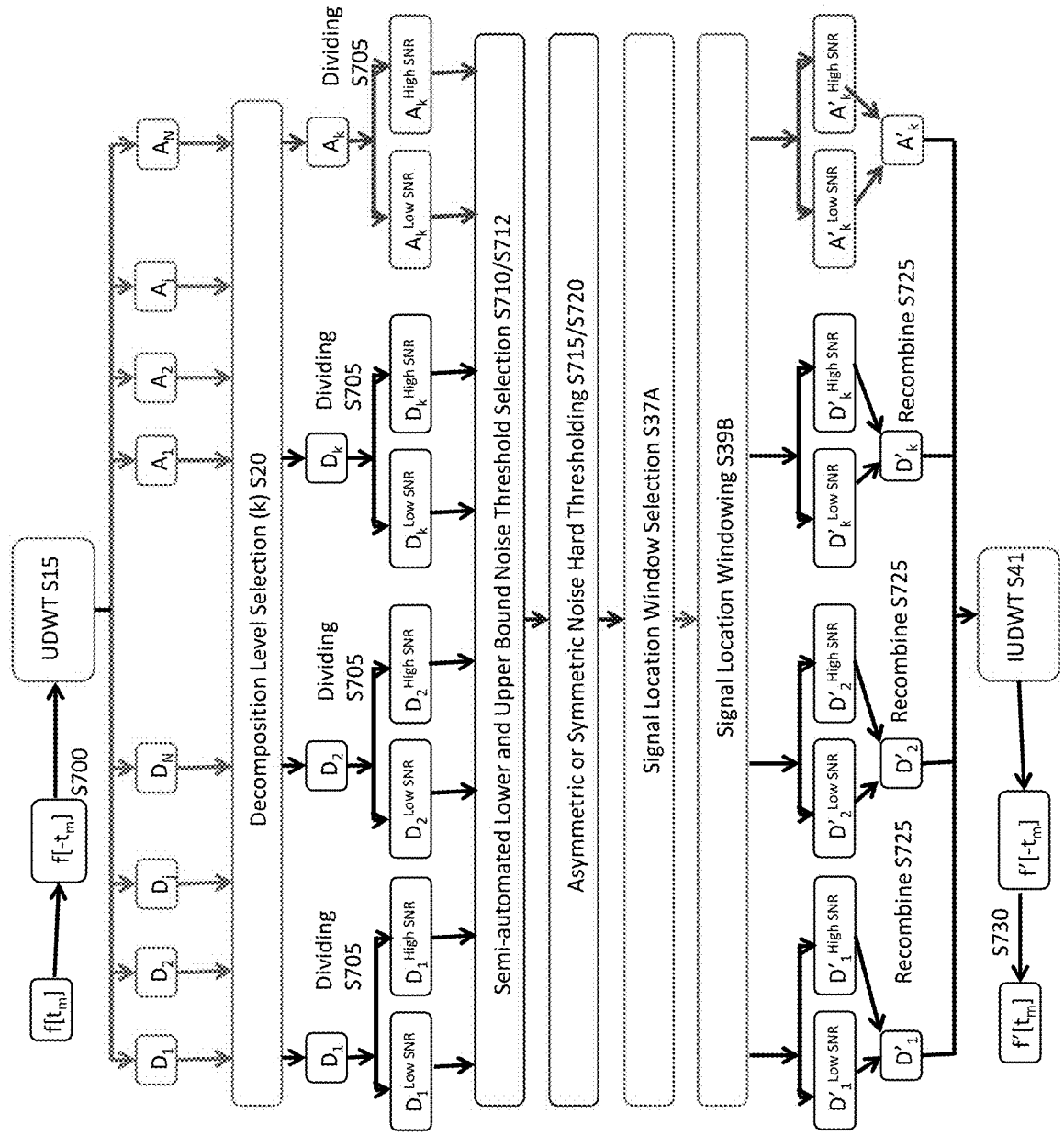

FIG. 7a depicts another method for denoising systems in accordance with other aspects of the disclosure. FIG. 7b depicts a diagram of the method depicted in FIG. 7a. The method depicted in FIG. 7a may be used when an input signal decays over time. A difference between the method depicted in FIG. 2a and the method depicted in FIG. 7a is that the input signal is reversed in time prior to transformation via UDWT. The method depicted in FIG. 7a may be used for input signals from a pulse-dipolar electron-spin resonance spectroscopy. In other aspects of the disclosure, this method may be used when different signal peaks have different SNRs such as some having a low SNR and others having high SNR. In some aspects, a difference threshold may be used to determine whether the signal peaks are "different" enough.

As described above, at S10, the signal may be acquired either via a sensor or retrieved from memory or the signal may be received via a network interface over a communication network S10A. The signal is identified in FIG. 11b as $F(t_m)$. Once the signal is either acquired either via a sensor or retrieved from memory (S10) or received via the network (S10A), the processor may reverse the signal at S700. The reversed signal is identified in FIG. 7b as $F(-t_m)$. For example, the signal may be flipped from left to right in an x-axis. If the signal is a time-based signal, the reversal of the signal, reverses the signal-in-time before taking the UDWT. Thus, the last sample point become the first sample point and vice versa. This is done to avoid distorting the initial (e.g., t=0) signal that may occur when a signal starts at a high value and decreases over the x-axis, e.g., time.

For example, reversing the signal may result instead in having small, near-zero, magnitudes at the start, allowing more accurate UDWT of the stronger part of the signal, e.g., initial response. The UDWT of the flipped signal contains the same information as that of the non-flipped signal.

The processor may then transform the reversed signal using selected wavelet(s) into both Detail (first set of components or first wavelet component) and Approximation (second set of components or second wavelet component) (S15). The Detail components ($D_1$-$D_N$) and Approximation components ($A_1$-$A_N$) are shown as the output of the UDWT in FIG. 7b. In an aspect of the disclosure, the processor may select Daubechises wavelet family for transformation in S12. This wavelet correlates very well with the signal properties of decaying oscillatory time-domain signals. This results in effective separation of signal and noise by increasing the difference between their wavelet coefficient patterns.

At S20, the processor may determine the number of decomposition levels as described in FIG. 3. The Detail components in the set decomposition level k, i.e., $D_1$-$D_k$, are shown in FIG. 7b as being output of S20. $A_k$ is also output. In some aspects of the disclosure, different decomposition levels may be used for high SNR and low SNR coefficients. For example, the number of decomposition levels for processing may be higher for low SNR coefficients than high SNR coefficients.

Another difference between the method depicted in FIGS. 7a and 2a, is that in the method depicted in FIG. 7a, the Detail components used for denoising are divided into two parts: high SNR and low SNR. Additionally, the Approximation component for the kth decomposition level may be divided into high SNR and low SNR. In an aspect of the disclosure, the division of the coefficients may be done prior to determining the decomposition levels for further processing. In an aspect of the disclosure, the kth composition level for the Approximation component may be different for the high SNR and low SNR.

For each of the determined decomposition levels used for denoising, at S705 the processor divides the Detail component into High SNR and low SNR.

In an aspect of the disclosure, the division may be based on a SNR threshold. The processor may determine an SNR for each sample point in the signal (in the signal domain). Based on the determined SNR at each sample point, the processor determines the SNR threshold. The processor may then compare the determined SNR at each sample point with the SNR threshold. If higher, the processor determines the sample point to be "high SNR", whereas if lower (or equal), the processor determines the sample point to be "low SNR". The correlation between a sample point and the coefficient in the detail component is known in view of the UDWT. Therefore, the processor, based on the decision of high SNR or low SNR for each sample point in the signal, determines the corresponding coefficient in the Detail component and divides the coefficients into high SNR or low SNR. Coefficients that correspond to sample points determined to be high SNR, may be deemed high SNR and coefficients that correspond to sample points determined to be low SNR, may be deemed low SNR. In an aspect of the disclosure, coefficients deemed high SNR and coefficients deemed low SNR may be separately processed for thresholding.

In another aspect of the disclosure, the SNR threshold may be based on a location within the signal. For example, the location in the middle of the signal may be used as the dividing point such that sample points left of the middle is deemed high SNR and sample points right of middle is low SNR (or vice versa). For example, if the signal is a time-based signal of 6 μsec, the SNR threshold may be 3 μsec. Sample points between 0-3 μsec may be deemed high SNR and sample points between 3 μsec-6 μsec may be deemed low SNR (including exactly 3 μsec). Once again, since the correlation between a sample point and the coefficients in the Detail component are known, high SNR coefficients and low SNR coefficients may be determined from the high SNR sample points and low SNR sample points. In another aspect of the disclosure, the division may be based on the reversed signal.

Depending on the signal type and data, sample points near each other or grouped together may have a similar SNR. However, in certain types of signals and certain data collections, similar SNR sample points may be scattered throughout the signal.

For a time-based signal, although the noise content is the same, the higher SNR part in earlier times may contain a signal that is less affected by noise, while noise tends to be dominant in the low SNR part. Therefore, the number of Detail coefficients to denoise may be different for both.

Advantageously, by separating the Detail components into lower and higher SNR parts avoids an overlap between the signal wavelet coefficients of the higher SNR part and the noise wavelet coefficients of the lower SNR part, preventing under-denoising or signal distortion.

The division is repeated for each decomposition levels determined for processing. In FIG. 7b, the divided coefficients are identified as $D_1^{Low\ SNR}$ and $D_1^{High\ SNR}$-$D_k^{Low\ SNR}$ and $D_k^{High\ SNR}$.

In an aspect of the disclosure, the Approximation component for the kth decomposition level may also be divided into high SNR and low SNR in a similar manner. The SNR threshold may be the same as determined for the Detail component. In other aspects of the disclosure, the Approximation component for the kth decomposition level may not be divided.

At S710, the processor may determine the thresholds for thresholding for each decomposition level determined for processing (thresholding). As noted above, coefficients grouped in the low SNR may be separately thresholded from the coefficients grouped in the high SNR. Therefore, the processor may separately determine the lower and upper thresholds for coefficients grouped in the low SNR and coefficients grouped in the high SNR. For example, the processor may determine a lower threshold ($\lambda_{1,LLowSNR}$) and an upper threshold ($\lambda_{1,HLowSNR}$) for $D_1^{Low\ SNR}$ and the processor may separately determine a lower threshold ($\lambda_{1,LHighSNR}$) and an upper threshold ($\lambda_{1,HHighSNR}$) for $D_1^{High\ SNR}$. As noted above, the lower threshold and the upper threshold may also separately be determined.

The processor may determine thresholds in a similar manner as described in FIG. 5. However, the equations used in the determination may be modified to account for the division such as to account for the different number of coefficients in each group (Low SNR and High SNR). For example, certain equations refer to Nj, which is the number of coefficients in a component in the decomposition level (see, e.g., equations 12 and 13). But since the number of coefficients are less due to the division, the equations are with respect to the actual number of coefficients in the divided groups. In an aspect of the disclosure, the same number of coefficients may be in the low SNR group in each decomposition level. Similarly, the same number of coefficients may be in the high SNR group in each decomposition level.

Similarly, $\mu_j$ and $\sigma_j$ which are the mean and standard deviation of the coefficients for the Detail component, would be modified to be the mean and standard deviation of the coefficients in the group (see, e.g., equations 8-11).

Equations 12-17 may also be modified to reflect the division of components into the low SNR and high SNR. For example, equation 12 is used to determine the peak-to-sum ratio for the negative coefficients. However, since the components are divided, two peak-to-sum ratios for the negative coefficients are determined, one for the low SNR and one for the high SNR, e.g., $S_{j,LLowSNR}$, $S_{j,LHighSNR}$. The peak-to-sum ratio for the negative coefficients with low SNR may be determined from only the negative coefficients with the low SNR and the peak-to-sum ratio for the negative coefficients with the high SNR may be determined from only negative coefficients with the high SNR.

Equation 13 is used to determine the peak-to-sum ratio for the positive coefficients. However, since the components are divided, two peak-to-sum ratios for the positive coefficients are determined, one for the low SNR and one for the high SNR, e.g., $S_{j,HLowSNR}$, $S_{J,HHighSNR}$. The peak-to-sum ratio for the positive coefficients with low SNR may be determined from only the positive coefficients with the low SNR and the peak-to-sum ratio for the positive coefficients with the high SNR may be determined from only positive coefficients with the high SNR.

Similarly, there are two upper and lower reference peak-to-sum ratios, $S_{r,HLowSNR}$, $S_{j,LHighSNR}$ and $S_{r,HLowSNR}$, $S_{j,HHighSNR}$, which are determined my modifying equations 14-15 to account for the division. Since equations 14 and 15 use the peak-to-sum ratio for the k+1 decomposition level, in an aspect of the disclosure, the processor also divides the components for the k+1 decomposition level into a low SNR and High SNR coefficients in the same manner as described above (where k may be different for the low SNR and high SNR).

For example, equation 14 is modified as follows:

$$S_{r,HLowSNR}=(S_{k,HLowSNR}+S_{k+1,HLowSNR})/2 \quad (14a)$$

$$S_{r,HHighSNR}=(S_{k,HHighSNR}+S_{k+1,HHighSNR})/2 \quad (14b)$$

For example, equation 15 is modified as follows:

$$S_{r,LLowSNR}=(S_{k,LLowSNR}+S_{k+1,LLowSNR})/2 \quad (15a)$$

$$S_{r,LHighSNR}=(S_{k,LHighSNR}+S_{k+1,LHighSNR})/2 \quad (15b)$$

Also, two kappa lower and uppers are also determined: $\kappa_{j,L_{LowSNR}}$ $\kappa_{j,L_{HighSNR}}$ and $\kappa_{j,H_{LowSNR}}$ $\kappa_{j,H_{HighSNR}}$.

The kappas are determined using the following modified equations 16 and 17:

$$\kappa_{j,L_{LowSNR}} = \left(\frac{S_{r,LLowSNR} - S_{j,LLowSNR}}{S_{r,LLowSNR}}\right)\kappa_{j,L_{minLowSNR}} \quad (16a)$$

$$\kappa_{j,L_{HighSNR}} = \left(\frac{S_{r,LHighSNR} - S_{j,LHighSNR}}{S_{r,LHighSNR}}\right)\kappa_{j,L_{minLowSNR}} \quad (16b)$$

$$\kappa_{j,H_{LowSNR}} = \left(\frac{S_{r,HLowSNR} - S_{j,HLowSNR}}{S_{r,HLowSNR}}\right)\kappa_{j,H_{minLowSNR}} \quad (17a)$$

$$\kappa_{j,H_{HighSNR}} = \left(\frac{S_{r,HHighSNR} - S_{j,HHighSNR}}{S_{r,HHighSNR}}\right)\kappa_{j,H_{minHighSNR}} \quad (17b)$$

As noted above, the process of determining the threshold is repeated for each decomposition level.

The processor may also determine the lower threshold and the upper threshold for the low SNR and the high SNR for the Approximation component for the kth decomposition level at S712 (where k may be different for low SNR and high SNR. However, in other aspects, when the coefficients for the Approximation component for the kth decomposition level is not divided based on SNR, the processor may determine only one lower threshold and one upper threshold for the Approximation component.

At S715, the processor may perform thresholding of the Detail components in each of the low SNR and high SNR (for each determined decomposition level) using equation 18 but substituting the different thresholds for the grouping. The processor may separately process coefficients in the low SNR and the coefficients in the high SNR using the corresponding set of $\lambda_{j,L},\lambda_{j,H}$. For example, the processor may compare the value of each negative coefficient (in the Low SNR group) with $\lambda_{j,L\ LOWSNR}$ and each positive coefficient (in the Low SNR group) with $\lambda_{j,HLOWSNR}$. Similarly, the processor may compare the value of each negative coefficient (in the High SNR group) with ALL HIGHSNR and each positive coefficient (in the High SNR group) with $\lambda_{j,HHIGHSNR}$. Thus, for each decomposition level instead of two thresholds there are four. $\lambda_{j,LLOWSNR}$, $\lambda_{j,HLOWSNR}$, $\lambda_{j,L\ HIGHSNR}$ and $\lambda_{j,HHIGHSNR}$. For example, positive coefficients (in the Low SNR) having a value less than or equal to $\lambda_{j,HLOWSNR}$ may be modified by the processor to zero. For example, negative coefficients (in the Low SNR) having a value greater or equal to $\lambda_{j,L\ LOWSNR}$ may be modified by the processor to zero.

At S1120, the processor may similarly apply the lower thresholds and the upper thresholds Approximation component for the kth composition level (where k may be different for the low SNR and high SNR).

At S37A, the processor may determine the position(s) or location(s) of the signal location window(s). Signal location window(s) may be positioned on coefficients in both the low SNR group and the high SNR group for the Detail component(s). Similar to above, the position(s) or location(s) of the signal location window(s) may be determined by evaluating coefficients from the kth decomposition level for the Detail component (where k may be different for the low SNR and high SNR).

In the aspect of the disclosure, since the coefficients are divided into low SNR and high SNR groups, the determination of the position(s) or location(s) of the signal location window(s) may also be separately determined for the low SNR group and the high SNR group (independently determined).

The position(s) or location(s) may be subjectively determined by looked at the value of the coefficients on a display. For example, the thresholded coefficients for the low SNR group may be displayed (for the kth decomposition level). The thresholded coefficients may include both changed and unchanged coefficients. As noted above, typically, noise coefficients dominate the signal coefficients are primarily in the initial decomposition levels as this is where noise is heavily present and signal is weak, however, moving towards the maximum decomposition level k, the signal coefficients will become dominant Therefore, the noise thresholding at the kth decomposition level likely will only remove the noise coefficients if any noise is present. The relative values of the coefficients for the kth decomposition level may be inspected to determine the location of the signal coefficients by magnitude. The signal location window(s) may be placed or superposed over the signal coefficients identified for the Low SNR group. The signal location windows may also be placed on the same coefficient locations in other decomposition levels for the Low SNR group.

This process may be repeated for the high SNR group (coefficients). In an aspect of the disclosure, if a decomposition level has an $S_j$ value of less than 0.01, the signal location window may not be positioned for the decomposition level for the low SNR group or the high SNR group.

In an aspect of the disclosure, the signal location window(s) determined for the low SNR group for Detail component (based on the kth decomposition level) may be positioned on the low SNR group (coefficients) for the Approximation component for the kth composition level in the same position without a need for a separate or independent determination (where k may be different for the low SNR and high SNR). Similarly, the position(s) of the signal location window(s) determined for the high SNR group for Detail component (based on the kth decomposition level) may be positioned on the high SNR group (coefficients) for the Approximation component for the kth composition level in the same position without a need for a separate or independent determination (where k may be different for the low SNR and high SNR).

In other aspects, the location(s) of the signal location window(s) may be objectively placed for the low SNR group and the high SNR group. Similar objective determination may be used as described above. The objection determination for the low SNR group for the Detail component may use the low SNR coefficients for the kth decomposition level for the Detail component and the determination for the high SNR group for the Detail component may use the high SNR coefficients for the kth decomposition level for the Detail component (where k may be different for the low SNR and high SNR).

The following description will be made for the low SNR coefficients, but the same process may be used for the high SNR coefficients.

In an aspect of the disclosure, the processor may examine the first coefficient in low SNR group, and if the coefficient is zero, continue examining the coefficients in the group until a non-zero value for a coefficient is discovered. The first non-zero value in the low SNR group may form the start of a signal location window for the low SNR group. The processor may continue examining coefficients in the group until another zero value coefficient in the low SNR group is discovered. Once another zero value coefficient in the low SNR group is discovered, the signal location window is ended. The process is repeated until all coefficients in the low SNR group are examined. In this manner, signal coefficients will be within the signal location window. More than one signal location window may be positioned for the low SNR group for the kth level. Effectively, the processor places one or more signal location windows over all non-zero value coefficients for the low SNR group for the kth decomposition level for the Detail component.

The non-zero coefficient values (for the low SNR) may be defined as:

$$V_{loc}^{LowSNR} = \{n : \forall D_k^{LowSNR}[n] \neq 0\} \quad (20A)$$

where $V_{loc}^{LowSNR}$ is the index of all non-zero low SNR group coefficients of the kth decomposition level for the Detail component. $D_k^{LowSNR}$ is the group of low SNR coefficients in the kth decomposition level.

The above process is repeated for the high SNR coefficient where the non-zero coefficient values (for the high SNR) may be defined as:

$$V_{loc}^{HighSNR} = \{n : \forall D_k^{HighSNR}[n] \neq 0\} \quad (20B)$$

where $V_{loc}^{HighSNR}$ is the index of all non-zero high SNR group coefficients of the kth decomposition level for the Detail component. $D_k^{HIGHSNR}$ is the group of high SNR coefficients in the kth decomposition level.

Like with the subjective determination, signal location windows for the low SNR may also be placed on the same coefficient locations for the low SNR group in other decomposition levels and signal location windows for the high SNR may also be placed on the same coefficient locations for the high SNR group in other decomposition levels other than decomposition levels only having noise.

In some aspects, depending on the input signal and the noise thresholding, signal location windows may not be needed for the Approximation component. Also in some aspects, the noise thresholding may be sufficient to denoise the signal without the need for the signal location windows for the Detail component as well. In some aspects of the disclosure, the location(s) or position(s) of the signal location window(s) may be first determined for the Approximation component and subsequently determine for the Detail component.

After the signal location windows are applied to the low SNR coefficients and the high SNR coefficients (for certain decomposition levels), coefficients within the windows are restored to their original values at S39B. That is, wavelet coefficients (low and high) lying within the respective signal location windows are restored as follows:

$$D_j'^{LowSNR}[n] = \begin{cases} D_j^{LowSNR}[n], & : \text{if } n \in V_{loc}^{LowSNR} \\ D_j'^{LowSNR}[n] & : \text{otherwise} \end{cases} \quad (21A)$$

$$D_j'^{HighSNR}[n] = \begin{cases} D_j^{HighSNR}[n], & : \text{if } n \in V_{loc}^{HighSNR} \\ D_j'^{HighSNR}[n] & : \text{otherwise} \end{cases} \quad (21B)$$

Similarly, in some aspects, where signal location windows are also applied to the kth decomposition level for the Approximation component, low/high SNR coefficients within the signal location windows (in the Approximation component) are also restored to their original values at S39B follows:

$$A_k'^{LowSNR}[n] = \begin{cases} A_k^{LowSNR}[n], & : \text{if } n \in V_{loc}^{LowSNR} \\ A_k'^{LowSNR}[n] & : \text{otherwise} \end{cases} \quad (22A)$$

$$A_k'^{HighSNR}[n] = \begin{cases} A_k^{HighSNR}[n], & : \text{if } n \in V_{loc}^{HighSNR} \\ A_k'^{HighSNR}[n] & : \text{otherwise} \end{cases} \quad (22B)$$

By applying the signal location windowing (S37A and S39B), low magnitude signal coefficients may be recovered where both signal and noise are present.

FIG. 7b shows the output of S39B being the denoised Detailed components of low SNR and high SNR $D'_1{}^{Low\ SNR} \cdot D'_1{}^{High\ SNR} \cdot D'_k{}^{Low\ SNR} \cdot D'_k{}^{High\ SNR}$ and denoised Approximation component $A'_k{}^{Low\ SNR} \cdot A'_k{}^{High\ SNR}$.

At S725, the processor may recombine the denoised coefficients from both the low SNR and high SNR from the Detail components, to result in denoised Detail components. For example, the processor may merge the two groups together to create the denoised Detail components. When the number of decomposition levels for the low SNR is higher than the number of decomposition levels for the high SNR, the unmodified coefficients for the high SNR may be combined with modified coefficients for the low SNR. For example, if there are 6 decomposition levels processed for the high SNR and 8 decomposition levels for the low SNR, then decomposition levels 7 and 8 for the high SNR are not thresholded, but are still combined with the thresholded low SNR decomposition levels 7 and 8. The denoised Detail components are identified in FIG. 7b as "recombine" $D'_1$-$D'_k$.

The processor may also recombine the denoised coefficients from both the low SNR and high SNR from the Approximation component of the kth decomposition level, to result in a denoised Approximation component (A'k).

At S41, the processor may perform an inverse undecimated discrete transformation to recover a denoised reversed signal using the recombined coefficients from the Detail components and the Approximation component. FIG. 7b shows the denoised reversed signal as $f'[-t_m]$.

At S730, the processor may unreverse the denoised reversed signal to recover a denoised signal. For example, the processor may flip the denoised reversed signal from right to left. For example, if the original signal was a time-based signal, the "unreversing" put the signal back to its original timing.

Figure 8A:
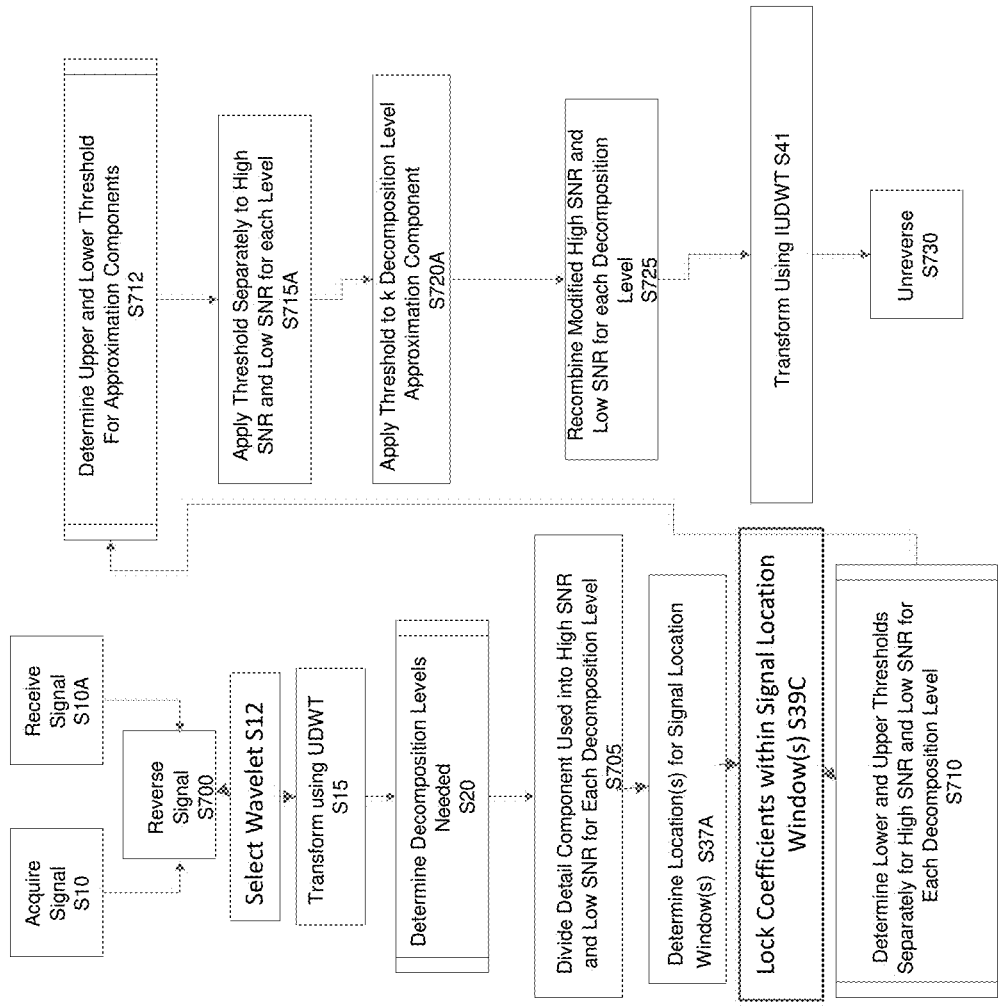
FIG. 8a depicts a flow chart for a method of denoising a signal in accordance with other aspects of the disclosure.
Figure 8B:
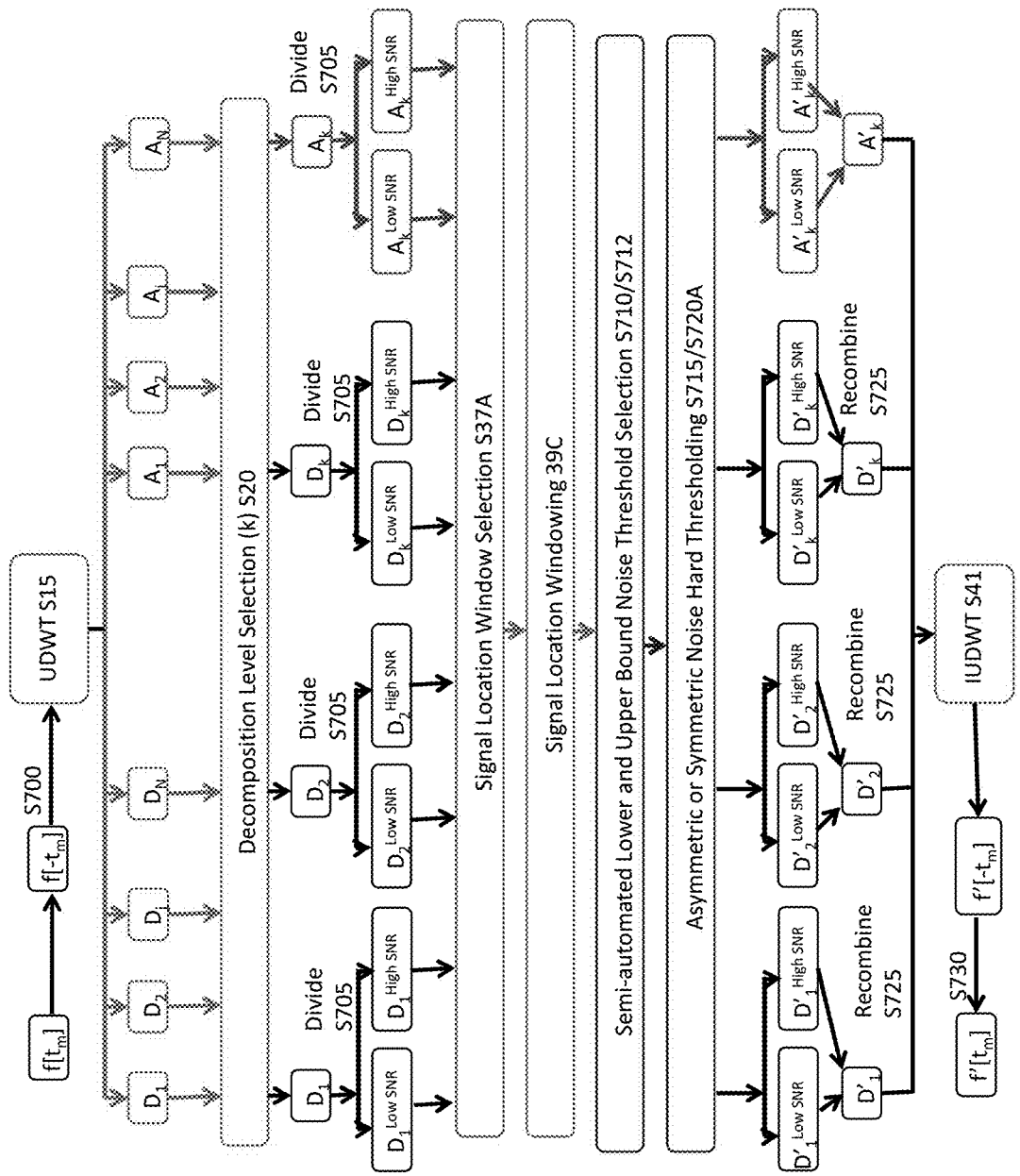

FIGS. 8a and 8b show a method where the determination of the location(s) or positions of the signal location window(s) are performed before thresholding when the input signal is reversed and the coefficients are divided into low SNR and high SNR. In this aspect of the disclosure, the determination of the location(s) or position(s) of the signal location window(s) for both the low SNR (coefficients) and the high SNR (coefficients) may be performed prior to thresholding (S715 and S720). This may be done where the location of the signal (verse noise) is a priori known as discussed above. Where the determination of location(s) or position(s) of the signal location window(s) is executed prior to thresholding, any coefficient within the signal location window is not changed by equation 21A/B and 22A/B at S715A and S720A. In an aspect of the disclosure, the processor may "lock" coefficients low SNR and high SNR within the signal location window(s) from being changed in S39C. For example, in an aspect of the disclosure, the processor may only specify low SNR and high SNR coefficients outside the signal location windows(s) for application of equations 21A/B and 22A/B. In other words, at S715A and S720A, the processor may only apply the equations 21A/B and 22A/B_ to low SNR coefficients and high SNR coefficients outside the signal location window(s) for the Detail components and the Approximation component, respectively, However, coefficients within the signal location window(s) are still used to determine the lower and upper thresholds at S710 and S712.

In other aspects of the disclosure, S39C may be omitted, and equations 21A/B and 22A/B may be modified to reflect the signal location windows for both the low SNR and high SNR as follows:

$$D'^{LowSNR}_j[n] = \begin{cases} 0, \text{ for } \lambda^{LowSNR}_{j,L} \leq D^{LowSNR}_j[n] \leq \lambda^{LowSNR}_{j,H} & \text{and where } n \text{ is outside the signal location window}(s) \\ D^{LowSNR}_j[n] \text{ otherwise} \end{cases} \quad (21C)$$

$$D'^{HighSNR}_j[n] = \begin{cases} 0, \text{ for } \lambda^{HighSNR}_{j,L} \leq D^{HighSNR}_j[n] \leq \lambda^{HighSNR}_{j,H} & \text{and where } n \text{ is outside the signal location window}(s) \\ D^{HighSNR}_j[n] \text{ otherwise} \end{cases} \quad (21D)$$

where $D'^{LowSNR}_j[n]$ is the denoised (or noise thresholded) Detail components for the low SNR and $D'^{HighSNR}_j$ is the denoised (or noise thresholded) Detail components for the high SNR.

$$A'^{LowSNR}_k[n] = \begin{cases} 0, \text{ for } \lambda^{LowSNR}_{j,L} \leq A^{LowSNR}_k[n] \leq \lambda^{LowSNR}_{j,H} & \text{and where } n \text{ is outside the signal location window}(s) \\ A^{LowSNR}_k[n] \text{ otherwise} \end{cases} \quad (22C)$$

$$A'^{HighSNR}_k[n] = \begin{cases} 0, \text{ for } \lambda^{HighSNR}_{j,L} \leq A^{HighSNR}_k[n] \leq \lambda^{HighSNR}_{j,H} & \text{and where } n \text{ is outside the signal location window}(s) \\ A^{HighSNR}_k[n] \text{ otherwise} \end{cases} \quad (22D)$$

where $A'^{LowSNR}_k[n]$ is the denoised (or noise thresholded) Approximation component for the low SNR for the kth decomposition level and $A'^{HighSNR}_k[n]$ is the denoised (or noise thresholded) Approximation component for the high SNR for the kth decomposition level (where k may be difference for the low SNR and the high SNR).

System

FIG. 9 depicts a block diagram of one example of a system 990 for denoising signals in accordance with aspects of the disclosure. The system 990 may include a source server 900, a plurality of relays 925 and a user terminal 950. The signals may be video or audio and may be streamed over a communication network, for example, using an Internet connection. The Source Server 900 may comprise a processor 905, memory 910 and a network interface 915. The memory 910 may be, but not limited to, RAM, ROM and persistent storage. The memory is any piece of hardware that is capable of storing information, such as, for example without limitation, data, programs, instructions, program code, and/or other suitable information, either on a temporary basis and/or a permanent basis.

The processor 905 may be a CPU. The CPU may be configured to execute one or more programs stored in a computer readable storage device such as the memory 910. For example, the CPU may be configured to execute a program causing the CPU to perform one or more of the above described denoising methods. The memory 910 further stores video and audio files or data. The video file may include a movie for streaming. The audio file may include a song for streaming. The memory 910 may store the decomposition levels used for denoising, upper and lower thresholds, the denoised signal, the Detailed components and Approximation components (coefficients), denoised Detailed components and Denoising approximation components (coefficients). In an aspect of the disclosure, the memory 910 may also include target SNR.

The processor 905 may perform one or more of the above-described denoising methods before compression or encoding the video for transmission. In another aspect of the disclosure, the processor 905 may perform the one or more of the above-described denoising methods during compression or encoding the video for transmission.

In another aspect of the disclosure, the processor 905 may calculate a signal to noise ratio for the denoised signal (video or audio) prior to transmission. Based on the calculated SNR for the denoising signal, the processor 905 may control the bit rate for the transmitted signal. Advantageously, by denoising the signal in accordance with one or more of the above-described methods, prior to the transmission of the signal, a higher bit rate may be achieved which will result in a reduction of bandwidth needed to transmit the signal (video or audio).

The network interface 915 may be a wired or wireless interface capable of transmitting and receiving.

The relays 925 may be electronic communications equipment placed between the source server 900 and a user terminal 950 such that the signals may be transmitted between the source server 900 and the user terminal 950. The relay 925 may be a cell tower (base station), a mobile terminal such as a smartphone, a tablet, a laptop, and etc., a router, a switch, and a repeater. Although not shown in FIG. 9, each relay may include a network interface for transmitting and receiving signals.

The user terminal 950 may include a network interface 915 (which may be the same as the network interface in the source server 900), a display 955, speaker(s) 960, memory 965 and a processor 970. The processor 970 also may be a CPU. The CPU may be configured to decode and decompress a video and cause the display 955 to display the same. The CPU may also be configured to cause the speakers to play the audio associate with the video as well as audio from a separate audio signal.

Each time a signal is relayed by the relay 925 (multiple hops) noise may be added to the signal. For example, if the network has a portion thereof that is wired, noise may be caused by the connection cables or electrical components of the relay itself.

Therefore, in an aspect of the disclosure, the relay 925 further includes a processor configured to execute one or more of the above described denoising methods on the signal prior to relaying to either a subsequent relay or the user terminal 950.

In another aspect of the disclosure, processor 970 in the user terminal may execute one or more of the denoising methods on the signal received before or during the decoding and decompression.

FIG. 10 depicts a block diagram of another system 1000 for denoising signals in accordance with aspects of the disclosure.

System 1000 may include a sensor 1005 (acquisition sensor), a processor 1010, memory 1015, a display 1020 and an input 1035. As described above, the sensor 1005 may be any component or components capable of have a response to a condition, such as, but not limited to, acceleration sensors, gyroscopes, seismometers, electrodes, light detectors and receivers.

In an aspect of the disclosure, the sensor 1005 may be connected to the processor 1010. For example, the sensor 1005 may be indirectly connected to the processor 1010 via an optical cable running between the sensor 1005 and a communication port. In another aspect of the disclosure, the sensor 1005 may be connected to the processor 1010 via a circuit board trace. The processor 1010 may be a CPU.

In an aspect of the disclosure, the processor 1010 may control the acquisition of an input signal and execute any of the above described denosing methods. The processor 1010 may cause the display 1020 to display a noisy signal, the denoised signal, the Detailed components and Approximation components (coefficients), denoised Detailed components and denoising Approximation components (coefficients).

The input 1035 may be a keyboard, a mouse, or a touch panel.

The memory 1015 may be, but not limited to, RAM, ROM and persistent storage. The memory is any piece of hardware that is capable of storing information, such as, for example without limitation, data, programs, instructions, program code, and/or other suitable information, either on a temporary basis and/or a permanent basis. The memory 1015 may store the raw data acquired by the sensor 1005, e.g., noisy signal. The memory 1015 may include programs for execution by the processor 1010 such as the CPU including a program for causing the CPU to execute any of the above described denoising method(s). The memory 1015 may store the decomposition levels used for denoising, upper and lower thresholds, the denoised signal, the Detailed components and Approximation components (coefficients), denoised Detailed components and denoised Approximation components (coefficients). In an aspect of the disclosure, the memory 1015 may also include target SNR.

In an aspect of the disclosure, the processor 1010 may execute any of the denoising methods for each acquisition (or detection) by the sensor 1005. In another aspect of the disclosure, the processor 1010 may average a preset number acquisition (or detections) by the sensor 1005 and wait until the preset number of acquisitions has been reached prior to execution any of the denoising methods.

In another aspect of the disclosure, the processor 1010, after denoising the signal, may calculate a signal to noise ratio (SNR) for the denoised signal. The processor 1010 may compare the calculated SNR to a target SNR stored in memory 1015. If the calculated SNR has reached or exceeded the target SNR, the processor 1010 may cause the sensor 1005 to stop acquiring a signal or cause the sensor 1005 to acquire a signal representing a different data point. Advantageously, since the system 900 provides a high SNR denoised signal, the number of acquisitions needed to provide the target SNR signal is minimized Typically, averaging of multiple acquisition increases the SNR of the averaged signal. Therefore, since the system can achieve the high SNR using fewer acquisitions, time for acquiring the data (for each data point) is reduced (as well as a cost savings).

In an aspect of the disclosure, the system 1000 may be a part of an imaging system such as a MRI system or a CT system. The sensor 1005 may be located in a separate room from the processor 1010 (and the other components in FIG. 10). The image signal (noisy) may represent one or more scans of data. The memory 1015 may also store a program for controlling the imaging system such as a MRI system or CT system. For example, the processor 1010 may cause the MRI or CT to execute a scan and the results of which are detected by the sensor 1005. Between each scan, the processor 1010 may execute any of the denoising methods described above on a single scan signal or an average of multiple scan signals. The result is a denoised signal either for a single scan or the average of multiple scans.

Prior to causing the MRI or CT to execute another scan in the same position, the processor 1010 may calculate an SNR for the denoised signal and compare the same with the target SNR. When the target SNR is reached, there is no need for executing another scan at the same position. Therefore, the processor 1010 may control the MRI or CT to move the scan to a different position (or end).

In another aspect of the disclosure, as part of the denoising, the processor 1010 may cause the display 1020 to display the denoised Detail components and the noised Detail components side-by-side for comparison (coefficients). A user, using the input 1035, may input a change in the scaling parameters $\kappa_{j,L}$ and $\kappa_{j,H}$ for the upper and lower thresholds, for one or more decomposition levels. Subsequently, the processor 1010 may re-execute the thresholding of the detail components and/or the kth approximation component using the new thresholds (e.g., S35, S35/S715/715A/720/720A) and subsequently re-executing the inverse transformation (S41).

In another aspect of the disclosure, as part of the denoising, the processor 1010 may cause the display 1020 to display the full scale Detail and Approximation components for a selection of the decomposition levels to denoise. The user, using the input 1035 may input a decomposition level and the processor 1010 may execute the thresholding for only the selected decomposition levels.

In other aspects of the disclosure, the system may include a standalone processor executing a program or application for denoising the input signal. The processor may be installed in a portable device such as a mobile phone or a tablet. The processor may also be installed in a personal computer. The input signal may be transmitted to the application in the processor using an API from another application running on the device. In other aspects, the input signal may be transmitted to the application from another device.

Aspects of the disclosure are able to recover spectral details even from noisy signals where they appear to be buried within the noise. This can allow studies to be conducted at low sample concentration and/or studies that were not feasible due to the long acquisition times, given that aspects of the disclosure reduce required signal averaging times, in some cases, by more than an order-of-magnitude. Many aspects of the disclosure do not require prior information regarding the signal. Additionally, aspects of the disclosure are not tailored to any particular type of signal and there the aspects described herein may be generally used to recover weak signals obtained in many fields of study.

Testing and Comparison to Other Methods

Certain aspects of the disclosure were tested from experimental data. Input signals are obtained from a cw-ESR system. Cw-ESR is used extensively to study the dynamics and structure of biomolecules. The cw-ESR spectrum is acquired in the magnetic field ($B_0$) domain, which is swept, i.e., $B_0=B_0(t)$ in a linear fashion.

Three types of experimental signals are acquired as examples to test aspects of the disclosure. The method depicted in FIG. 2a (and FIG. 2b) was used. The results of the method depicted in FIG. 2a (and FIG. 2b) were compared with results from a method depicted in FIGS. 1a and 1b of U.S. Pat. No. 10,891,719 issued on Jan. 12, 2021. The subject matter of U.S. Pat. No. 10,891,719 is incorporated by reference.

Example 1

The ESR was performed at 20° C. using a spectrometer (BRUKER ELEXYS-II E500) at a microwave frequency of 9.4 GHz (X-band), which is standard (corresponding to a DC magnetic field of 0.34 Telsa).

The sample used was a 50 µM aqueous solution of spin-probe molecule Tempol (4-Hydroxy-2,2,6,6-Tetramethylpiperidine 1-oxly). The sample was placed in a glass capillary of 0.8 mm ID, which was subsequently introduced into the microwave cavity situated between the pole caps of the dc magnet. The magnetic field was then swept over a range of 60 G corresponding to the resonant spectral range for a period of 2 minutes and a 82 ms time constant was used.

In addition, small coils place at the sides of the resonator provided a small magnetic field modulation of +−0.02G at a frequency of 100 kHz. The 100 kHz modulated ESR signal was detected with a lock-in detector at this frequency, providing a first derivative of the absorption signal. A low power 0.2 mW microwave radiation was used to avoid saturation the ESR.

The spectral data consisted of 4096 points along the magnetic-field sweep.

Multiple scans were performed with a delay of 4 s between scans. The results of the scans were averaged. By averaging different number of scans, different SNRs were obtained, two separately averaged signals were generated by averaging 4 and 16 scans, resulting in an SNR of 15 and 57, respectively, for the main components and an SNR of 1.5 and 0.5, respectively, for the weak components. A reference signal was generated by averaging signals from 500 scans. The reference signal was used for a comparison with the denoised signals.

As the wavelet, the coiflet 3 was used because it best resembles the spectra. An ESR spectrum is frequently composed of Lorentzian and Gaussian functions, or mixtures of both. A $T_r=0.20$ was used.

Figure 1:
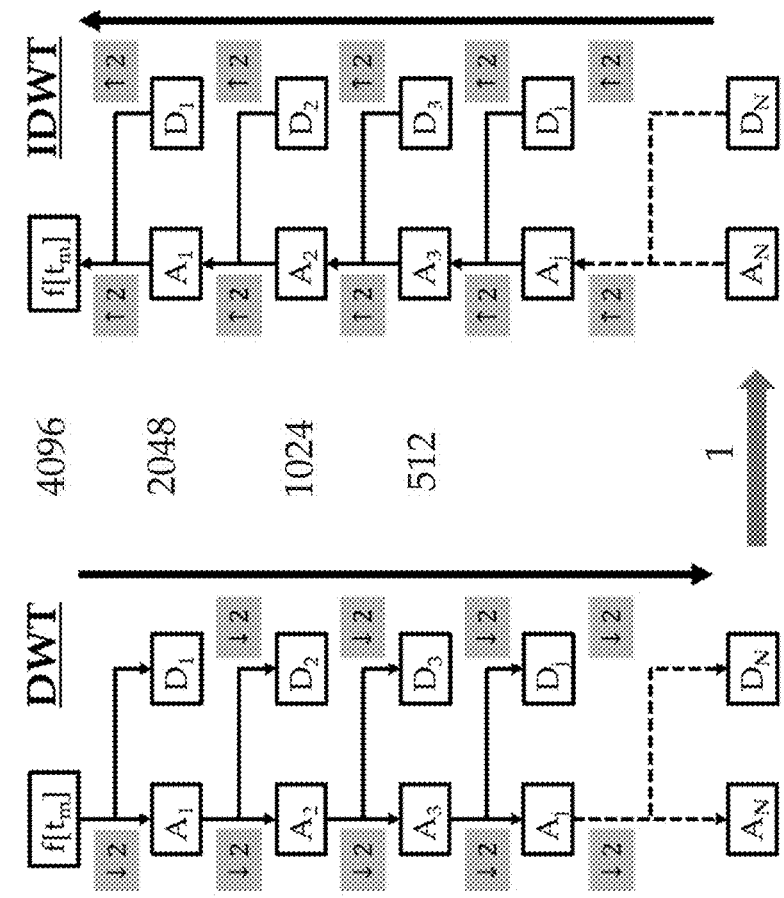
FIG. 1 shows a block diagram of an example of a DWT and an inverse discrete wavelet transformation (IDWT)
Figure 11:
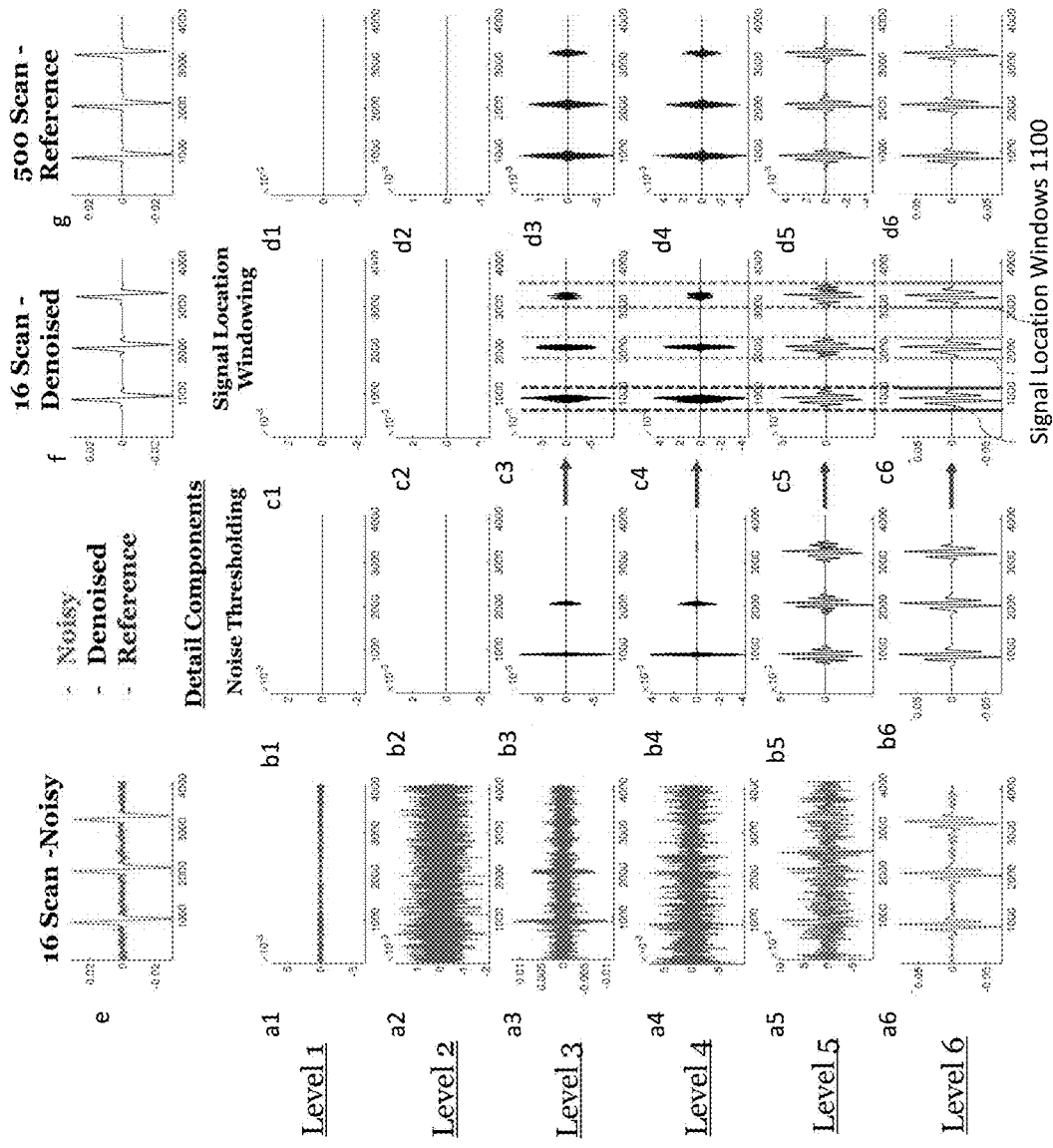
FIGS. 11a-11g are diagrams showing the results for the denoising method depicted in FIGS. 2a and 2b for Example 1, where

FIG. 11e depicts the input signal used in the method. The signal was averaged for 16 scans. FIG. 11e shows the signal in the wavelet domain. Six decomposition levels were used for thresholding. As shown in FIGS. 11a1, 11a2, 11b1 and 11b2, the first two decomposition levels contain almost all noise (FIG. 11a1) and (FIG. 11a2) are the coefficients prior to noise thresholding and (FIG. 11b1) and (FIG. 11b2) are coefficients after thresholding. The post thresholded coefficients from level 6 were used to determine the locations of the signal location windows 1100. As can be seen from FIG. 11b6, there are three signal coefficient regions and therefore, three signal location windows were positioned. The three signal location windows 1100 are represented in FIG. 11c6 by three vertical solid line pairs. The three signal location windows were also positioned in the same positions for decomposition levels 3-5. The three signal location windows 1100 are represented by three dashed line pairs in levels 3-5. Signal location windows 1100 were not positioned in decomposition levels 1-2 because these levels only contained noise. This is also shown in FIGS. 11d1-11d2. FIGS. 11c3-11c6 depict the coefficients after the values were restored to the original values within the signal location windows 1100. This is best shown by comparing FIG. 11a6 with FIG. 11c6 for coefficients within the signal location windows 1100. One can see that at decomposition levels 3 and 4, noise thresholding has removed signal coefficients representing the shfs (cf. FIGS. 11b3 and 11b4)). Signal location windowing recovers those coefficients (cf. FIGS. 6c3 and 6c4) and preserves the shfs on the spectrum.

After windowing, as shown in FIGS. 11c3 and 11d3 and 11c4 and 11d4, the coefficients for decomposition levels 3 and 4 for the Detail components are rendered in good agreement with the reference signal. The coefficients for the Detail component for the decomposition level 5 had a slight improvement (cf FIGS. 11b5, 11c5 and lids).

Figure 12:
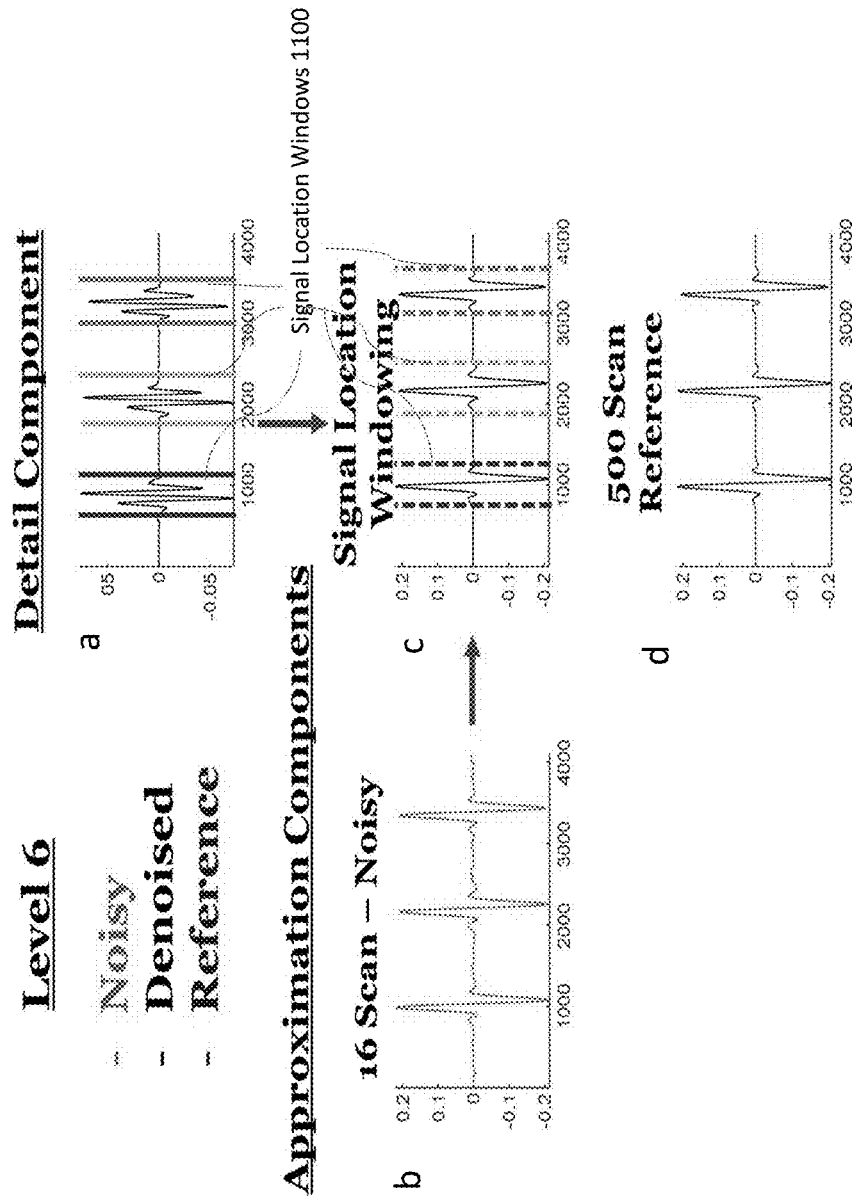
FIG. 12a-12d are diagrams showing results of the denoising method depicted in FIGS. 2a and 2b for Example 1, where

Additionally, for the Approximation component, decomposition level 6 was also windowed using the three signal location windows 1100 determined from decomposition level 6 of the Detail component. The positions of the signal location windows 1100 for the Approximation component for component level 6 are the same as the positions for the signal location windows for the Detail components. This is shown in FIGS. 12a and 12c. FIG. 12c depicts the coefficients within the signal location windows 1100 restored to the original value. See FIGS. 12b and 12c for coefficients within the signal location windows 1100. The three signal location windows 1100 are shown in FIG. 12c with dashed line pairs. As can be seen in FIGS. 12c and 12d the denoised Approximation Component (FIG. 12c) has good agreement with the coefficients for the reference signal (for the Approximation component for decomposition level 6) (FIG. 12d). The coefficients in FIG. 12c show less noise than the original coefficients as shown in FIG. 12b.

Figure 13:
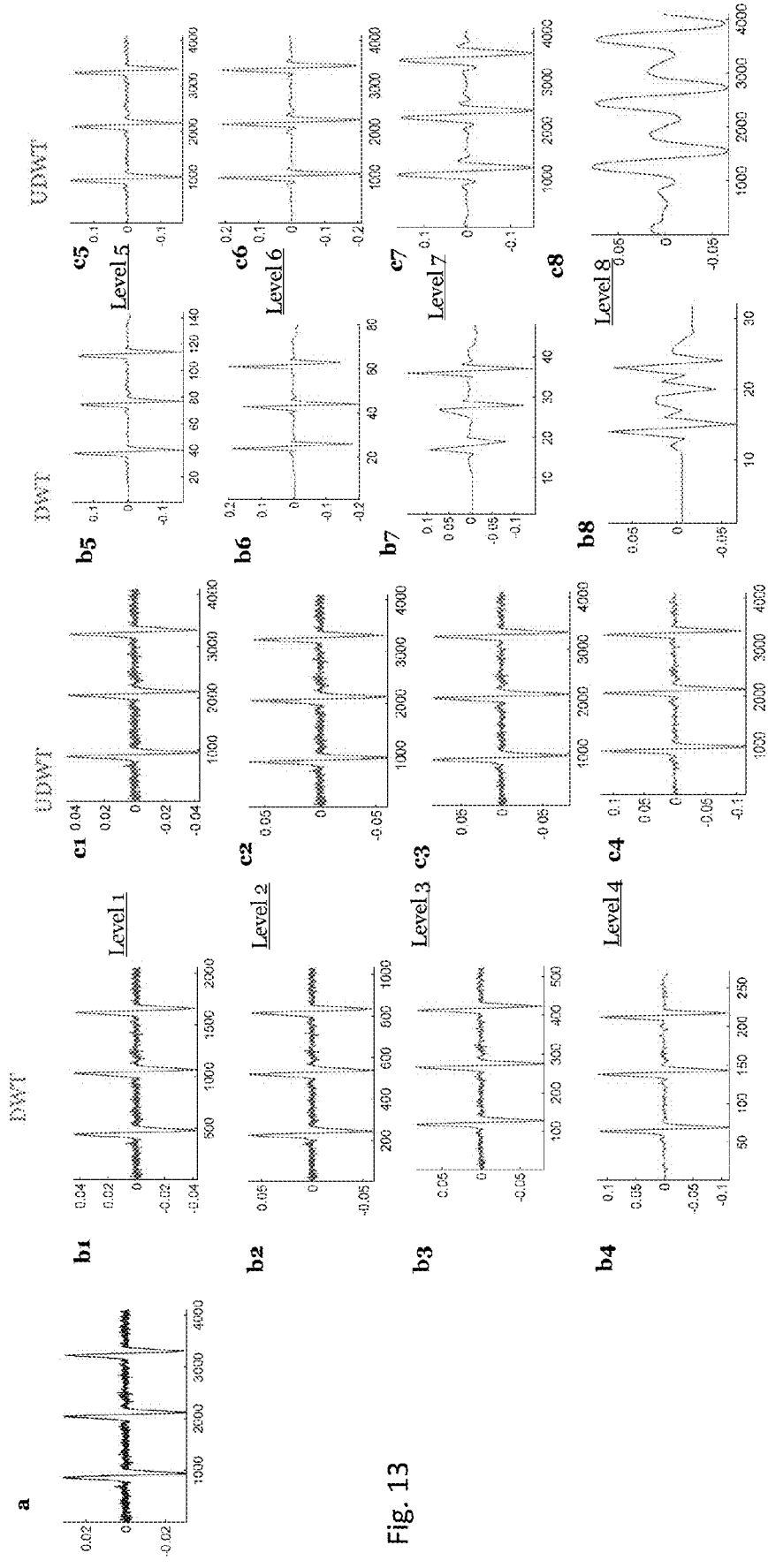
FIG. 13 shows the Approximation components and FIG. 14 shows the Detail components, and, FIG. 13b1-c8 compares coefficients for the Approximation components subject to DWT verses UDWT for eight decomposition levels
Figure 14:
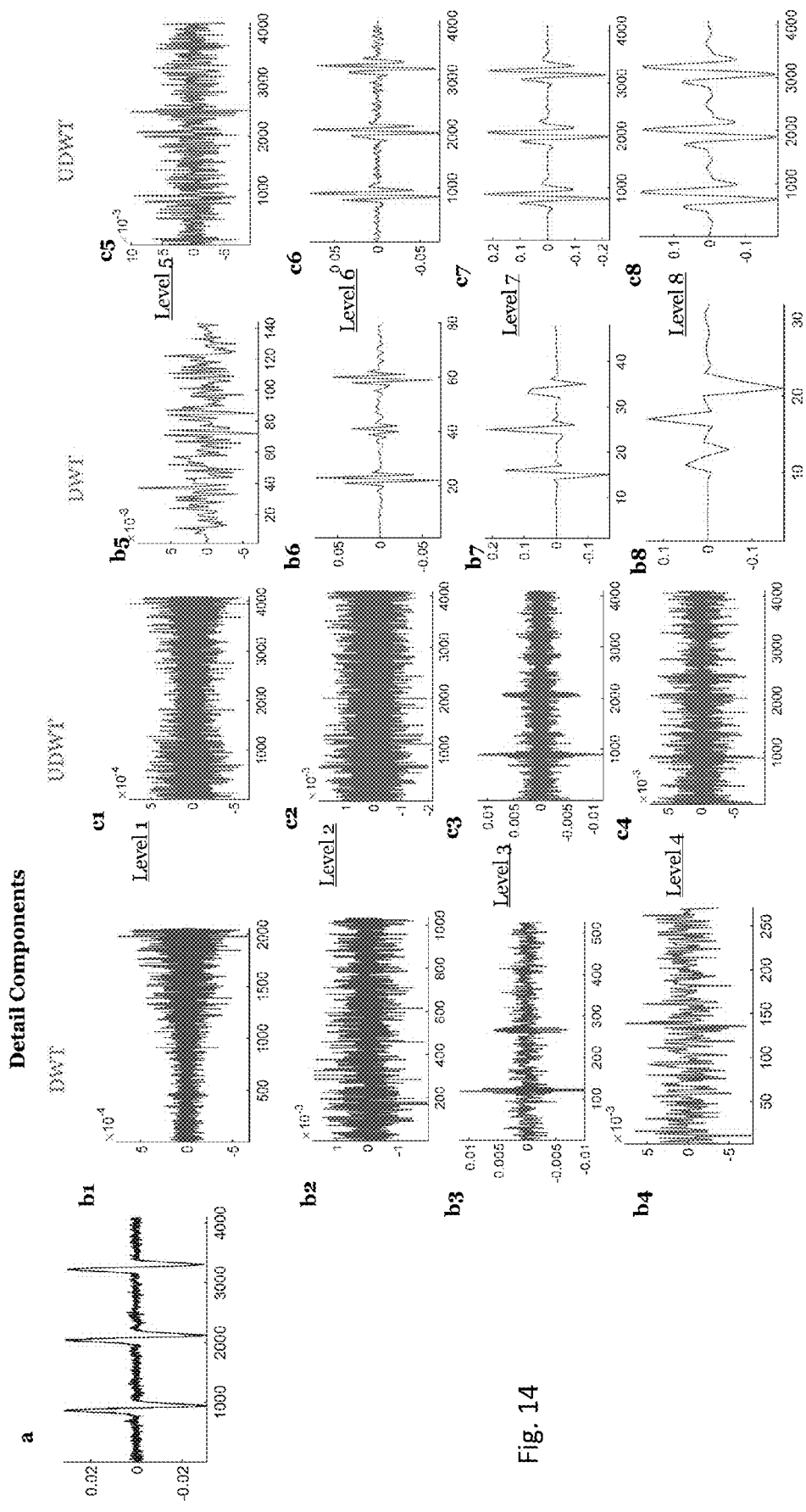

The same input signal was processed using a decimated DWT in accordance with the method described in U.S. Pat. No. 10,891,719 (FIGS. 1a and 1b). FIGS. 13 and 14 show a comparison between the coefficients for the same signal using an UDWT in accordance with aspects of this disclosure verses a DWT as disclosed in U.S. Pat. No. 10,891,719. As can be seen, with UDWT, there is a one-to-one correspondence with the coefficients of the input signal and coefficients in each decomposition level. UDWT already yields significantly improved results compared to DWT. This is because, with UDWT, the enhanced resolution strengthens signal coefficients (FIGS. 14c6 and 14c7) compared to the DWT procedure (FIGS. 14b6 and 14b7), allowing more signal coefficients, in particular belonging to weak peaks, to have magnitude greater than noise coefficients and leading to recovery of some of the weak peaks previously submerged in noise. Furthermore, the UDWT yields redundant coefficients that provide resilience against noise thresholding procedure. If noise thresholding eliminates a weak signal coefficient while retaining another signal coefficient nearby, the signal can be still effectively recovered with the retained coefficient that contains the necessary (and overlapping) information. In DWT, coefficients contain non overlapping information, and hence, a signal coefficient removal impacts the denoising results.

Figure 15:
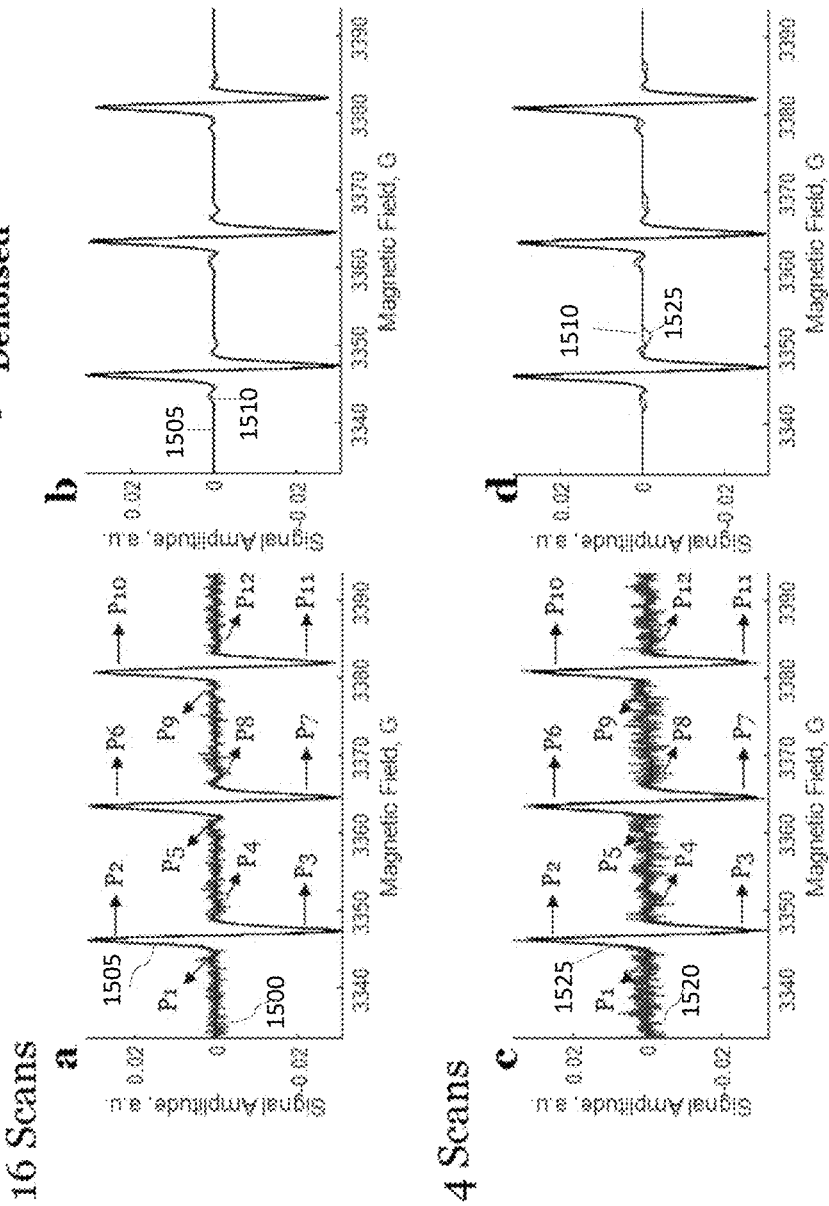
FIGS. 15a-15d depict results for the denoising method depicted in FIGS. 2a and 2b for Example 1, where
Figure 19:
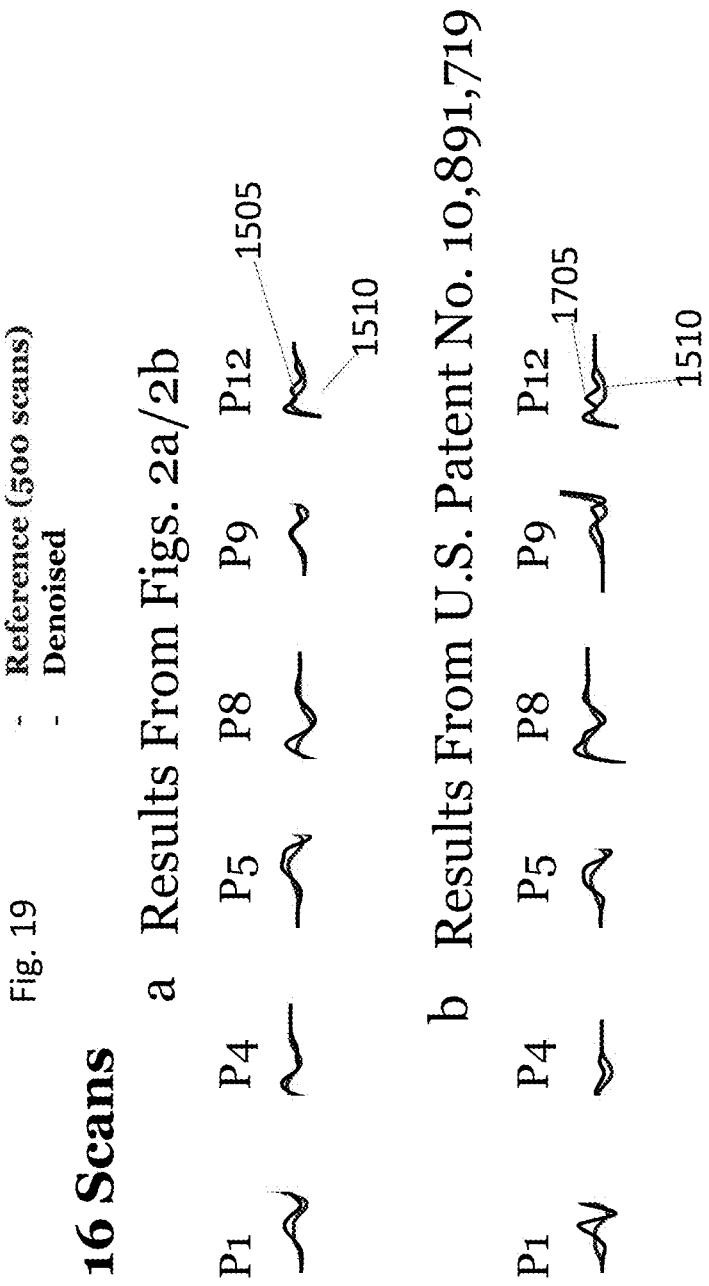

FIGS. 15a and 15b show results of a noisy signal generated by averaging 16 scans (noisy signal 1500. The corresponding denoised signal 1505. 12 peaks were identified P1-P12. The peaks are labeled on FIG. 15a. The denoised signal 1505 is superposed on the reference signal 1510. FIGS. 15c and 15d show results of a noisy signal generated by averaging 4 scans (noisy signal 1520) and the corresponding denoised signal 1525. The denoised signal 1525 is superposed on the reference signal. As seen in FIG. 15a and FIG. 15c, the noisy signal 1520 has more noise than noisy signal 1500, which is expected. Denoised signal 1505 more closely aligned with the reference signal 1510 than denoised signal 1525. As shown in FIGS. 15a and 15b, the peaks do not overlap each other and return to zero prior to the next peak.

The SNR was calculated using the following equation:

$$SNR = \frac{Signal_{Peak}}{Noise_{RMS}} \quad (24)$$

where $Signal_{Peak}$ is the maximum peak height of the signal and $Noise_{rms}$ is the root-mean-square of the noise presented. SNR measures both distorting (i.e., structural) and non-distorting (i.e., nonstructural) noise in the signal, but it cannot differentiate between them.

The noise present is measured from spectral positions where there is no signal present in the experimental data. The SNR is thus the inverse of the amount of noise present with respect to the maximum peak height of the signal.

$SNR_{Peak-to-Peak}$ was also calculated to determine the SNR of an overall signal as follows:

$$SNR = \frac{Signal_{Peak-to-Peak}}{Noise_{RMS}} \quad (25)$$

where $SNR_{Peak-to-Peak}$ is the magnitude between maximum and minimum peak height.

Equations 24 and 25 were used to calculate the local and global SNR, respectively. As shown in FIGS. 15a and 15c, the signals in Example 1 contain multiple peaks with different magnitudes, equation 24 was used to find the SNR for each peak. Equation 25 provides a stand measure of overall SNR for a complete signal, which is typically composed of derivative of the absorption.

Thus, a structure similarity index measure (SSIM) was used as another objective measure. The SSIM enables the estimation of the structural similarity or fidelity of the noisy and of the denoised signals at 4 and 16 scans (shown herein) with respect to the reference 500 scan signal. The SSIM is calculated as:

$$SSIM = \frac{(2\mu_X\mu_Y + c_1)(2\sigma_{XY} + c_2)}{(\mu_X^2 + \mu_Y^2 + c_1)(\sigma_X^2 + \sigma_Y^2 + c_2)} \quad (26)$$

where X is either the noisy or denoised signal; Y is the reference signal, $\mu_X$ and $\mu_Y$ are the mean values of X and Y, respectively, $\sigma_X$ and $\sigma_Y$ are the standard deviation values of X and Y, respectively, $\sigma_{XY}$ is the covariance of X and Y and $c_1$ and $c_2$ are small positive constants used for stabilizing each term.

The SSIM value ranges between −1 and 1 and is 1 when X is identified to Y. The more that X is structurally reassembly Y, the SSIM will be closed to 1.

SSIM was used for the complete signal and localized SSIM for individual peak regions. Because the strong peaks can overwhelm or dominate the overall SSIM value, the local SSIM provides better information about the fidelity of each peak for noisy and denoised data. To ensure the appropriate measure, $c_1$ and $c_2$ were selected to be 10% of the peak magnitude of the peak under consideration. FIG. 16 shows a table (TABLE 1), which shows the SNR and SSIM for the identified peaks and the overall signal. Table 1 shows the SNR and SSIM for both the noisy signals 1500/1520 and SSIM for the denoised signals 1505/1525. Table 1 also shows the SSIM for a denoised signal using the method disclosed in U.S. Pat. No. 10,891,719.

FIGS. 17a-22b depict a comparison of the results from denoising in accordance with aspects of the disclosure such as depicted in FIGS. 2a/2b and denoising in accordance with the method depicted in FIGS. 1a/1b in U.S. Pat. No. 10,891,719. As can be seen, Peaks 2, 3, 6, 7, 10 and 11 are strong peaks from $^{14}$N hyperfine splitting (hfs) and Peaks 1, 4, 5, 8, 9, and 12 are weak (hfs) peaks from $^{13}$C in natural abundance (1.1%). Table 1 shows that strongest peaks, with overall SNR of 57 for the 16 scan average and 15 for the 4 scan average, are well recovered before and after denoising in accordance with aspects of the disclosure and provide the greatest fidelity (SSIM 0.9975 for the 16 scan average and SSIM of 0.9992 for the 4 scan average). Denoising using the method depicted in FIGS. 1a/1b of U.S. Pat. No. 10,891,719 has a lower SSIM for the same (SSIM of 0.9936 for the 16 scan average and 0.9909 for the 4 scan average). This is also seen in FIGS. 17a and 18d. The weak peaks are not observable in the original "noisy" spectra in either case of signal averaging. However, as shown in FIGS. 17b and 19a, the weak peaks are recovered using denoising in accordance with aspects of the disclosure of the 16 scan average signal and are partially recovered from the 4 scan average signal (see FIGS. 18b and 20a). There is an improved recovery of the weak peaks from the denoising in accordance with the method depicted in FIGS. 1a/1b of U.S. Pat. No. 10,891,719 (cf. FIGS. 17b and 17d, 18b and 18d, 19a and 19b and 20a and 20b). This is also shown in FIG. 16, Table 1.

With respect to the input signal generated from the 16 scan average, the original SNR for the weak peaks are around unity (greater than 0.5), but very good to excellent recovery is achieved for most of the weak peaks by denoising in accordance with aspects of the disclosure. See e.g., Table 1. This recovery has a better SSIM than the recovery using the denoising in accordance with the method depicted in FIGS. 1a/1b of U.S. Pat. No. 10,891,719 (with the exception of peak 8).

With respect to the input signal generated from the 4 scan average, the original SNR for the weak peaks is less than 0.5 (generally about half that for the 16 scan average case, implying that there is still a substantial noise presence in the designated signal coefficients (which denoising using the windowing retains)). Again, the recovery in accordance with aspects of the disclosure such as FIGS. 2a/2b has a better SSIM than the recovery using the denoising in accordance with the method depicted in FIGS. 1a/1b of U.S. Pat. No. 10,891,719 (with the exception of peak 1). The recovery can inform about accurate peak locations.

Thus, the results show that denoising in accordance with aspects of the disclosure can reliably recover the signal when the initial SNR is greater than 0.5.

Figure 21:
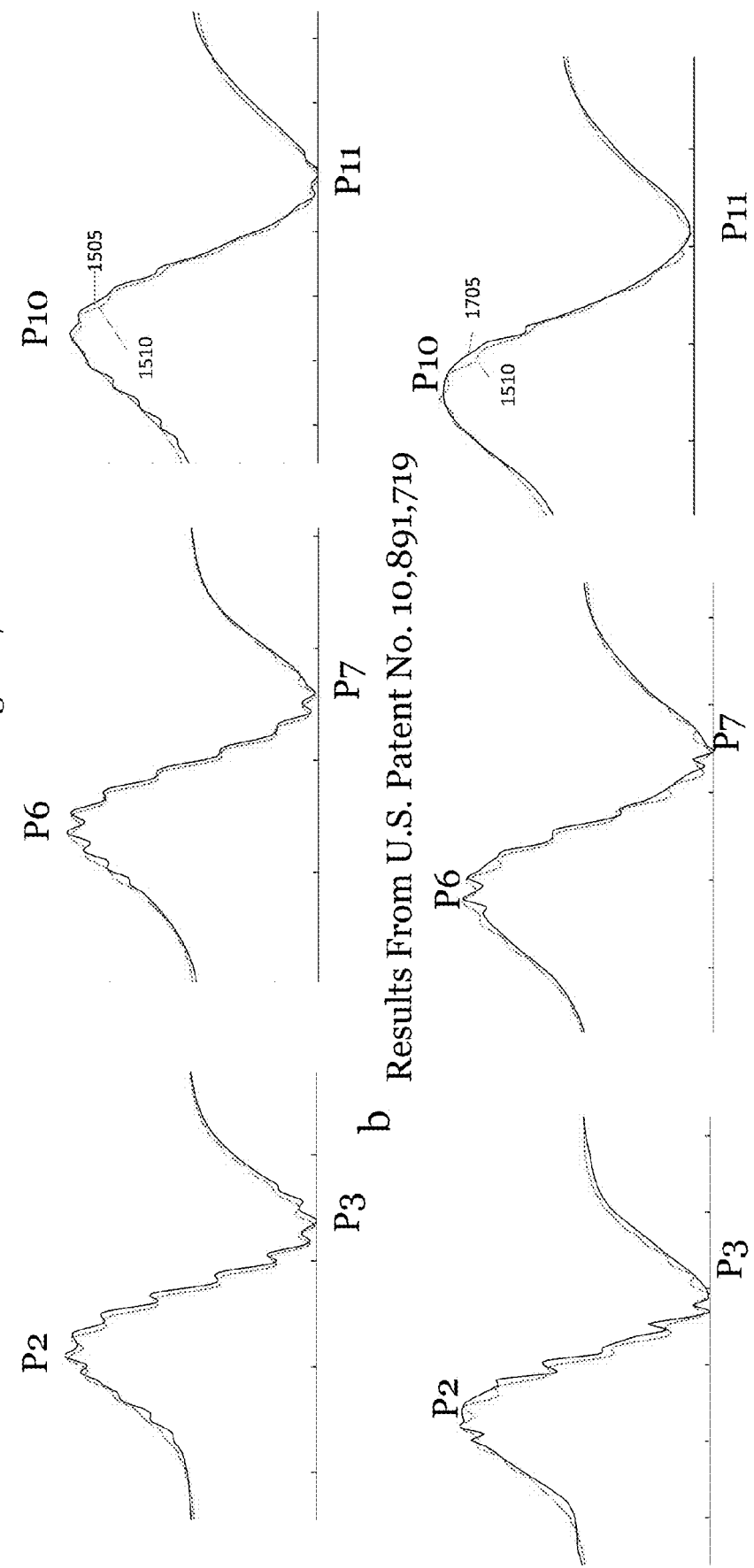

As shown in FIGS. 21a-22b, the main peaks (strong peaks) are spread out and one observers superhyperfine structures (shfs) on them due to $^1$H hf lines. This cannot be seen in the noisy spectra but may be recovered in the reference signal (500 scan average). As can be seen in FIG. 21a, denoising in accordance with aspects of the disclosure has excellent recovery of this structure. Denoising in accordance with the method depicted in FIGS. 1a/1b of U.S. Pat. No. 10,891,719 can also recover the shfs from the noisy signal generated from the 16 scan average.

For the 4 scan averages, denoising in accordance with aspects of the disclosure can recover the shfs whereas denoising using method depicted in FIGS. 1a/1b of U.S. Pat. No. 10,891,719 did not. cf FIG. 22a and FIG. 22b.

Figure 23:
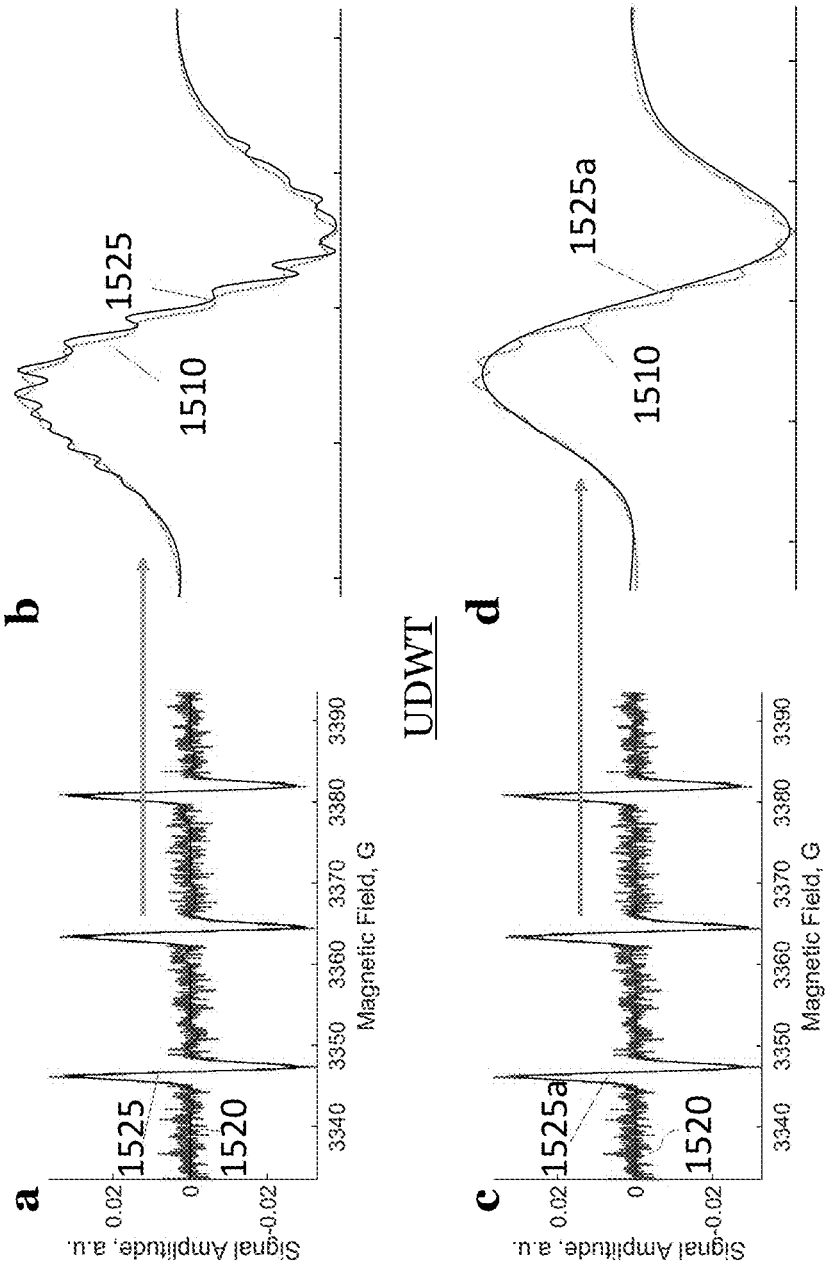
FIGS. 23a-23d depict a comparison of the results of denoising using UDWT and signal location windows (and windowing) verses UDWT without signal location windows (and windowing), where

FIGS. 23a-23d depicts a comparison of the results of denoising using UDWT and signal location windows (and windowing) verses UDWT without signal location windows (and windowing). Using WDWT alone can recover strong and weak peaks nearly comparable to denoising using UDWT and signal location windows (and windowing). However, as seen in FIGS. 23b and 23d, denoising using UDWT and signal location windows (and windowing) can resolve the $^1$H super hyperfine structures that overlap the strong peaks. FIG. 23b shows the central main component (P6 and P7) of the denoised signal 1525 and the reference signal 1510 showing the shfs. Similarly, FIG. 23d shows the central main component (P6 and P7) of the denoised signal 1525a and the reference signal 1510. As seen in FIG. 23b, the signal location windows and windowing recover the coefficients while preserving the shfs on the spectrum.

Example 2

An ESR spectrum was obtained under different conditions from above to provide a different and more complex spectrum for denoising. It was obtained on a home-built (ACERT) 95 GHz ESR spectrometer with a dc magnetic field of 3.3 Tesla. The spectra were recording in a liquid crystalline membrane (Lβ) phase at 37 degrees.

The sample consisted of a concentrated water suspension of multi-lamellar vesicles of DMPC (1,2-dimyristoyl-sn-glycero-3-phosphocholine) doped with 0.5% of a lipid spin label, 16-PC (1-acyl-2-[16-(4,4-dimethyloxazolidine-N-oxyl)stearoyl]-sn-glycero-3-phosphocholine).

The acquisition parameters were: sweep width of 250 G, sweep time of 2 min with a time constant of 100 ms. The millimeter-wave power was 16 mW and the spectrum consists of 512 points (spectral dataset). The field modulation parameters were: 6 G modulation amplitude and 100 kHz modulation frequency.

The signal used for denoising was an average of 18 scans.

Three noisy signals were generated by averaging 1, 4 and 18 scans. Their respective SNRs were 21, 33 and 73. Six peaks P1-P6 were identified. In example, 2, at least some of the peaks at least partially overlap where one peak does not return to zero prior to the start of another peak. SNR and SSIM for the local peaks and the complete spectrum were calculated and are shown in FIG. 25. "Signal" in Table 2 refers to the complete spectrum for which SNR and SSIM were obtained. For the SSIM, $c_1$ and $c_2$ were equal and had a value of 10-13 The denoised signal 2405 from the noisy signal 2400 (18 scan average) was used as the reference for the SSIM and in Table 2 (FIG. 25), the SSIM values are shown as NA.

The minimum peak SNR was for Peak 3 for the 1 scan noisy signal 2420 (SNR of 2). This peak had a SSIM value of 0.6554 for the noisy signal 2420. As shown in FIG. 25, the denoised results enhance the SNR for each peak and the overall signal SNR by more than several orders-of-magnitude for all three noisy signals 2400, 2410, and 2420. More importantly, the denoised signals 2405, 2415, 2425 (and 2405a, 2415a, 2425a) are able to successfully extract the lineshapes buried under noise.

Figure 24:
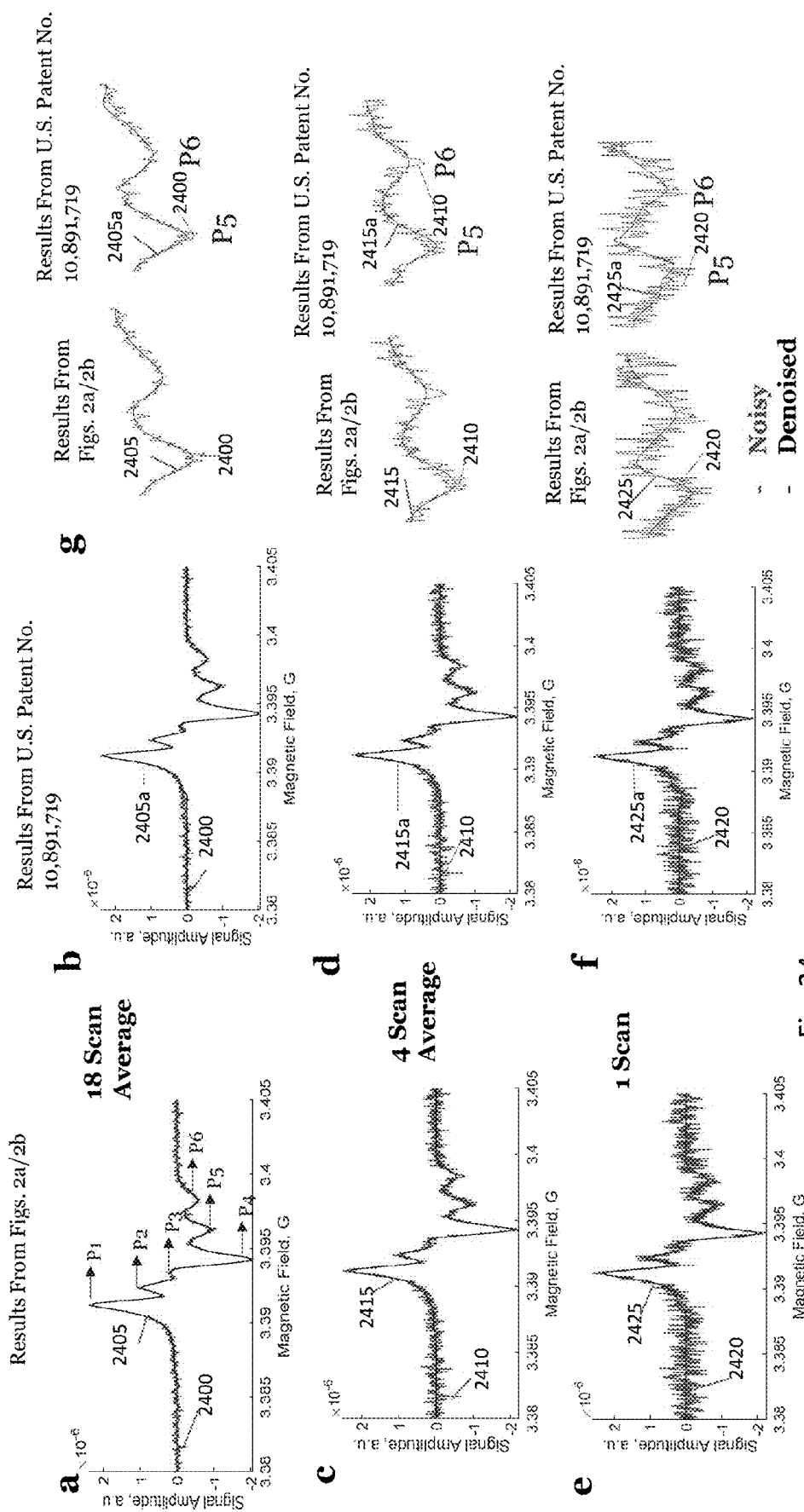
FIGS. 24a-24g depict a comparison of the results of denoising three noisy signals of Example 2 denoised in accordance with aspects of the disclosure and denoised in accordance with FIGS. 1a/1b of U.S. Pat. No. 10,891,719, where

For example, the third peak P3 in FIGS. 24c and 24e, is overwhelmed by noise with little evidence of its presence (see noisy signal 2410, 2420). However, as shown in FIGS. 24c and 24e, the third peak P3 is resolved in the denoised signals 2415, 2425. Also as shown in FIGS. 24a, comparing the noisy signal 2400 and denoised signal 2405, there is a clear peak (P3).

While denoising in accordance with the method depicted in FIGS. 1a/1b of U.S. Pat. No. 10,891,719 performs very well for the denoising the noisy signals 2400, 2410 (18 scan average and the 4 scan average), see FIG. 24b and FIG. 24d (2405a, 2415a), denoising in accordance with aspects of the disclosure performs even better as shown in FIG. 24a and FIG. 24c (2405, 2415). But for denoising a noisy signal generated from the single scan (noisy signal 2420), denoising in accordance with the method depicted in FIGS. 1a/1b of U.S. Pat. No. 10,891,719 does not yield a good SNR and denoising in accordance with aspects of the disclosure (see FIG. 25), is very successful. However, the SSIM for both methods are almost the same (with denoising in accordance with aspects of the disclosure a little better) (see FIG. 25 and FIG. 24g).

FIG. 24g shows peaks P5 and P6 where there is greater fidelity in the denoised signal in accordance with aspects of the disclosure (especially for the denoising of the single scan noisy signal) (see, 2425 verses 2425a, 2415 verses 2415a and 2405 verses 2405a).

Example 3

The radical di-(4-tert-butyl-phenyl) nitroxide was dissolved in toluene at a 100 μM concentration and thoroughly deoxygenated using the freeze-thaw technique. The spectra were recorded at the same conditions as for Example 1. Multiple narrow ESR lines due to the interaction of the unpaired electron with a 14N nucleus and several protons were exhibited. However, a small magnetic field modulation at 100 kHz of 20 mG was used to produce the weak signal obtained from a single scan, whereas the strong reference signal from an average of 500-scan was obtained with a 100 mG field modulation to enhance the signal and suppress noise (10 times higher strength). (Magnetic field modulation is used to provide the derivative of the absorption signal).

The SNR of the noisy signal 2600 was approximately unity (1.1). Table 3 (FIG. 27) and FIGS. 26*c* and 26*e* demonstrates the ability of the aspects of the disclosure such as shown in FIGS. 2*a*/2*b* to extract a periodic, repeating pattern in the processed data from a noisy signal 2600 with low SNR (1.1). As shown in the reference signal 2610 (see FIGS. 26*e* and 26*f*), the signal consists of many narrow hf lines. This hyperfine structure is from three main groups of lines due to the $^{14}N$ nucleus: each of these is further split into a larger number of lines resulting from the interaction of the unpaired electron within two groups of four equivalent protons in the ortho- and meta-positions relative to the nitroxide moiety. That is, four ortho protons split each $^{14}N$ hf line into a quinlet of hf lines by the four meta protons. These hf lines overlap, so the whole spectrum is difficult to analyze or even detect in the presence of substantial noise.

However, aspects of the disclosure enable the unique ability to elicit and recover the periodic patterns that are undetectable by the eye.

As shown in Table 3 (FIG. 27), there were 66 hf lines (pks) in the reference signal 2610 which was obtained from averaging of 500 scans and more favorable experimental conditions (the SNR for the reference signal 2610 is listed as NA because it was obtained under different experimental conditions to guarantee a very high SNR so it is not relevant for comparison). Advantageously, denoising the noisy signal 2600 in accordance with the method depicted in FIGS. 2*a*/2*b* to obtain denoised signal 2605 was able to recover all 66 peaks with high fidelity (SNR=$8.5 \times 10^3$ and an SSIM=0.9608) from the initial noisy SNR of 1.1 and SSIM of 0.08. The reference signal 2610 was used as a reference for calculating the SSIMs (and thus the SSIM was not calculated to the reference signal 2610 and is labeled NA in Table 3).

Figure 26:
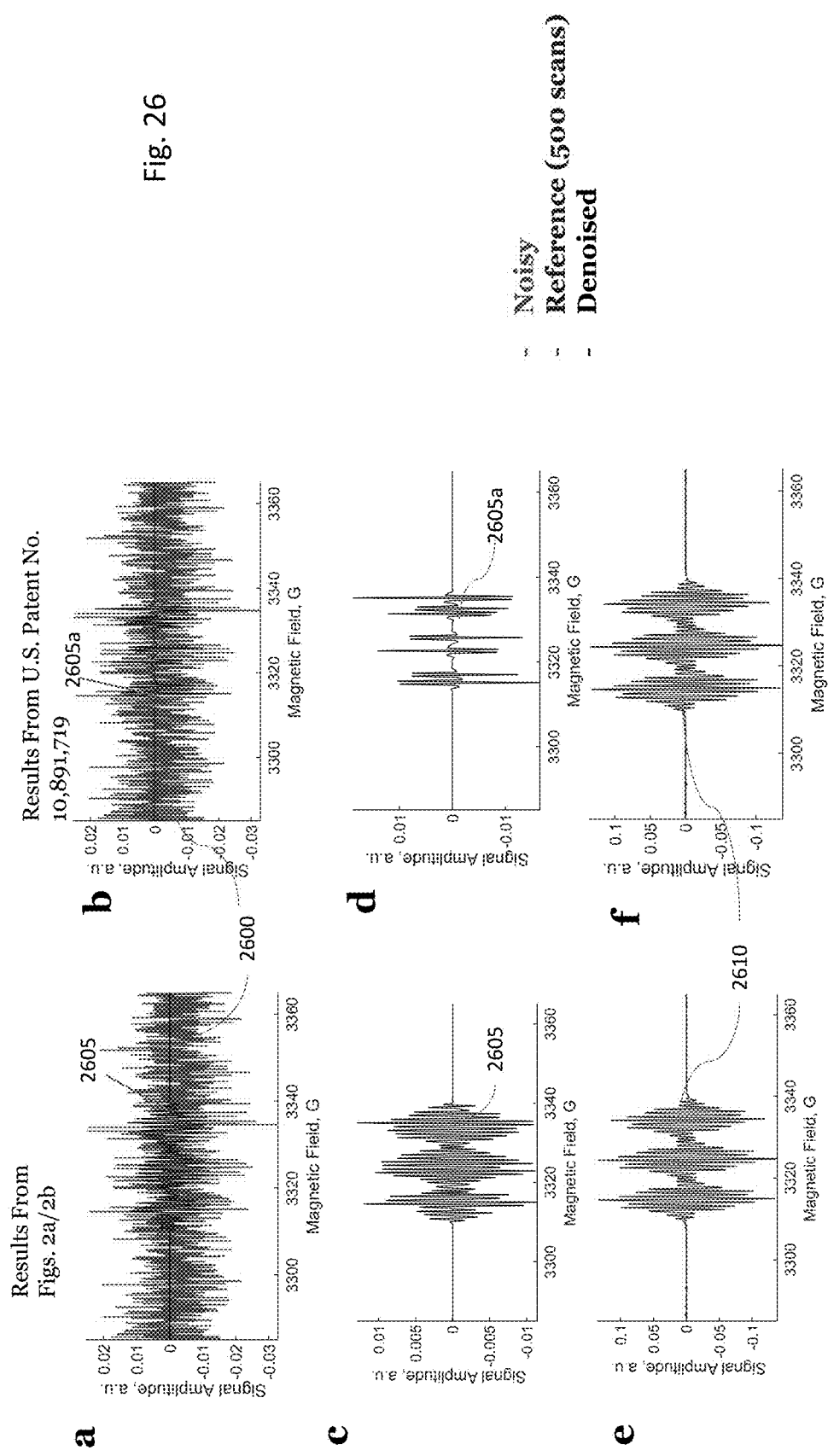
FIGS. 26a-26f depict a comparison of the results of denoising a noisy signal of Example 3 denoised in accordance with aspects of the disclosure and denoised in accordance with FIGS. 1a/1b of U.S. Pat. No. 10,891,719, where

The hf lines appear in distinct positions, represented by a few wavelet coefficients and was able to be readily separated from the random noise by the denoising method depicted in FIGS. 2*a*/2*b* (cf. FIGS. 26*a*, 26*c* and 26*e*). As can be seen from FIGS. 26*c* and 26*e*, the results of denoising in accordance with the method depicted in FIGS. 2*a*/2*b* (FIG. 26*c*) compare very favorably with the reference 2610 (FIG. 26*e*), providing nearly perfect recovery of all features.

However, denoising of the noisy signal 2600 in accordance with the method depicted in FIG. 1*a*/1*b* of U.S. Pat. No. 10,891,719 (denoised signal 2605*a*) was not successful at recovering most of the hf lines (cf. FIGS. 26*b*, 26*d* and 26*f*). As seen in Table 3 (FIG. 27), denoising of the noisy signal 2600 in accordance with the method depicted in FIG. 1*a*/1*b* of U.S. Pat. No. 10,891,719 (denoised signal 2605*a*) was only able to recover 26 hf lines. The SNR for denoised signal 2605*a* was not calculated (and labeled NA in Table 3) because it was unable to recover most of the hf lines, obviating the necessity of the measure. The number of the hf lines for the noisy signal 2600 cannot be counted because it suppressed all of the hf lines (and labeled NA in Table 3).

Various aspects of the present disclosure may be embodied as a program, software, or computer instructions embodied or stored in a computer or machine usable or readable medium, or a group of media which causes the computer or machine to perform the steps of the method when executed on the computer, processor, and/or machine. A program storage device readable by a machine, e.g., a computer readable medium, tangibly embodying a program of instructions executable by the machine to perform various functionalities and methods described in the present disclosure is also provided, e.g., a computer program product.

The computer readable medium could be a computer readable storage device or a computer readable signal medium. A computer readable storage device, may be, for example, a magnetic, optical, electronic, electromagnetic, infrared, or semiconductor system, apparatus, or device, or any suitable combination of the foregoing; however, the computer readable storage device is not limited to these examples except a computer readable storage device excludes computer readable signal medium. Additional examples of the computer readable storage device can include: a portable computer diskette, a hard disk, a magnetic storage device, a portable compact disc read-only memory (CD-ROM), a random access memory (RAM), a read-only memory (ROM), an erasable programmable read-only memory (EPROM or Flash memory), an optical storage device, or any appropriate combination of the foregoing; however, the computer readable storage device is also not limited to these examples. Any tangible medium that can contain, or store, a program for use by or in connection with an instruction execution system, apparatus, or device could be a computer readable storage device.

A computer readable signal medium may include a propagated data signal with computer readable program code embodied therein, such as, but not limited to, in baseband or as part of a carrier wave. A propagated signal may take any of a plurality of forms, including, but not limited to, electro-magnetic, optical, or any suitable combination thereof. A computer readable signal medium may be any computer readable medium (exclusive of computer readable storage device) that can communicate, propagate, or transport a program for use by or in connection with a system, apparatus, or device. Program code embodied on a computer readable signal medium may be transmitted using any appropriate medium, including but not limited to wireless, wired, optical fiber cable, RF, etc., or any suitable combination of the foregoing.

The terms "Processor", as may be used in the present disclosure may include a variety of combinations of fixed and/or portable computer hardware, software, peripherals, and storage devices. The "Processor" may include a plurality of individual components that are networked or otherwise linked to perform collaboratively, or may include one or more stand-alone components. The hardware and software components of the "Processor" of the present disclosure may include and may be included within fixed and portable devices such as desktop, laptop, and/or server, and network of servers (cloud).

The terminology used herein is for the purpose of describing particular embodiments only and is not intended to be limiting the scope of the disclosure and is not intended to be exhaustive. Many modifications and variations will be apparent to those of ordinary skill in the art without departing from the scope and spirit of the disclosure.

What is claimed is:

1. A method of denoising a signal comprising:
    transforming a signal using an undecimated discrete wavelet transformation into at least a first wavelet component, the first wavelet component having a plurality of coefficients, the first wavelet component having a plurality of decomposition level, where a number of the plurality of coefficients in each level are the same;
    for each decomposition level determined for thresholding, comparing each coefficient of the plurality of coefficients with a threshold, and selectively changing a value of the coefficient based on the comparison thereby generating a first modified first wavelet component having changed coefficients and unchanged coefficients for a decomposition level;

positioning one or more windows on the first modified first wavelet component for a highest decomposition level determined for thresholding, by evaluating the changed coefficients and unchanged coefficients in the first modified first wavelet component for the highest decomposition level;

changing coefficients in the first modified first wavelet component for the highest decomposition level determined for thresholding to its original value when the coefficients are within the one or more windows while keeping the coefficients outside the one or more windows the same as in the first modified first wavelet component to generate a second modified first wavelet component for the highest decomposition level determined for thresholding;

positioning the one or more windows on the first modified first wavelet component for a subset of other decomposition levels of the plurality of decomposition levels at the same positions;

changing coefficients in the first modified first wavelet component for each of the subset of other decomposition levels to its original value when the coefficients are within the one or more windows while keeping the coefficients outside the one or more windows the same as the first modified first wavelet component to generate a third modified first wavelet component, respectively, for each decomposition level of the subset of other decomposition levels; and transforming, using an inverse undecimated discrete wavelet transformation, the first modified first wavelet component for decomposition levels other than the subset of other decomposition levels and the highest decomposition level, respectively, the second modified first wavelet component for the highest decomposition level and the third modified first wavelet component for the subset of other decomposition levels, respectively, into a denoised signal.

2. The method of denoising a signal according to claim 1, wherein the subset of other decomposition levels does not include decomposition levels having coefficients only containing noise.

3. The method of denoising a signal according to claim 1, wherein the position of each of the one or more windows is such that the ends of the one or more windows are where a value of the coefficients change from non-zero to zero and zero to non-zero.

4. The method of denoising a signal according to claim 1, further comprising determining a number of the plurality of decomposition levels for thresholding by examining at least coefficients for the first wavelet component for at least two different decomposition levels.

5. The method of denoising a signal according to claim 1, wherein the threshold for each decomposition level determined for thresholding is variable.

6. The method of denoising a signal according to claim 5, wherein the threshold for each decomposition level determined for thresholding is different.

7. The method of denoising a signal according to claim 6, wherein the threshold for each decomposition level determined for thresholding comprises a lower threshold and an upper threshold and the lower variable threshold is a negative value and compared to negative coefficients and the upper variable threshold is a positive value and compared to positive coefficients.

8. The method of denoising a signal according to claim 7, wherein coefficients having values between the lower variable threshold and the upper variable threshold are reduced as the change.

9. The method of denoising a signal according to claim 1, further comprising:

transforming a signal using an undecimated discrete wavelet transformation into the first wavelet component and a second wavelet component, both the first wavelet component and the second wavelet component having a plurality of coefficients, the first wavelet component and the second wavelet component having a plurality of decomposition levels, where the number of the plurality of coefficients in each level are the same;

for the highest decomposition level determined for thresholding, comparing each coefficient in the second wavelet component with a second threshold, and selectively changing a value of the coefficient based on the comparison, thereby generating a first modified second wavelet component having changed coefficients and unchanged coefficients;

positioning one or more windows on the first modified second wavelet component for a highest decomposition level determined for thresholding, by evaluating the changed coefficients and unchanged coefficients in the first modified second wavelet component for the highest decomposition level determined for thresholding;

changing coefficients in the first modified second wavelet component for the highest decomposition level determined for thresholding to its original value when the coefficients are within the one or more windows while keeping the coefficients outside the one or more windows the same as the first modified second wavelet component to generate a second modified second wavelet component; and transforming, using an inverse undecimated discrete wavelet transformation, the first modified first wavelet component for decomposition levels other than the subset of other decomposition levels and the highest decomposition level, respectively, the second modified first wavelet component for the highest decomposition level, the third modified first wavelet component for the subset of other decomposition levels, respectively, and the second modified second wavelet component, into the denoised signal.

10. The method of denoising a signal according to claim 9, wherein the position of the one or more windows on the second wavelet component is different than the position of the one or windows on the first wavelet component.

11. The method of denoising a signal according to claim 2, further comprising determining whether a decomposition level contains all noise.

12. The method of denoising a signal according to claim 11, wherein the determining is based on whether a maximum coefficient value for the decomposition level divided by a sum of all coefficient values for the decomposition level is less than a sparsity threshold.

13. The method of denoising a signal according to claim 1, wherein the signal is a scan or an average of scans from an electron spin resonance (ESR)-based pulsed dipolar spectroscopy.

14. The method of denoising a signal according to claim 1, wherein the signal has a signal to noise ratio for a peak greater than 0.5.

15. The method of denoising a signal according to claim 1, wherein a signal to noise ratio for a peak is increased by at least three orders of magnitude in the denoised signal than in the signal.

16. The method of denoising a signal according to claim 1, further comprising:
displaying the first modified first wavelet component having changed coefficients and unchanged coefficients for each decomposition level; and
determining the position of the one or more windows by evaluating the displayed first modified wavelet component for at least the highest decomposition level determined for thresholding.

17. The method of denoising a signal according to claim 1, wherein the signal is selected from a group consisting of an audio signal and a video signal.

18. The method of denoising a signal according to claim 17, wherein the signal is streamed over a network, the network comprising at least one source server storing the signal, one or more relay nodes and a user terminal.

19. The method of denoising a signal according to claim 17, further comprising acquiring the signal using a sensor selected from a group consisting of acceleration sensors, gyroscopes, seismometers, electrodes, light detectors and receivers.

20. The method of denoising a signal according to claim 13, wherein prior to acquiring another scan or average of scans, a processor executing the method of denoising a signal according to claim 1.

21. The method of denoising a signal according to claim 1, further comprising transforming the signal using a decimated discrete wavelet transformation into at least a third wavelet component, the third wavelet component having a plurality of coefficients, the third wavelet component having a plurality of decomposition level, where a number of coefficient in each level are different and determining a number of the plurality of decomposition levels for thresholding by examining at least coefficients for the third wavelet component for at least two different decomposition levels.

22. A method of denoising a signal comprising:
transforming a signal using an undecimated discrete wavelet transformation into at least a first wavelet component, the first wavelet component having a plurality of coefficients, the first wavelet component having a plurality of decomposition level, where a number of the plurality of coefficients in each level are the same;
positioning one or more windows on the first wavelet component for a highest decomposition level determined for thresholding;
for the highest decomposition level determined for thresholding, comparing each coefficient outside the one or more windows with a threshold, and selectively changing a value of the coefficient based on the comparison thereby generating a first modified first wavelet component having changed coefficients and unchanged coefficients for the highest decomposition level determined for thresholding;
positioning the one or more windows on the first wavelet component for a subset of other decomposition levels of the plurality of decomposition levels at the same positions;
for the subset of other decomposition levels, comparing each coefficient of the plurality of coefficients outside the one or more windows with a threshold, and selectively changing a value of the coefficient based on the comparison thereby generating a second modified first wavelet component having changed coefficients and unchanged coefficients, respectively for each decomposition level of the subset of other decomposition levels;
for the remaining decomposition levels of the plurality of decomposition levels lower than the highest decomposition level determined for thresholding, comparing each coefficient of the plurality of coefficients with a threshold and selectively changing a value of the coefficient based on the comparison thereby generating a third modified first wavelet component having changed coefficients and unchanged coefficients, respectively for each decomposition level of the remaining decomposition levels; and
transforming, using an inverse undecimated discrete wavelet transformation, the first modified first wavelet component for the highest decomposition level, the second modified first wavelet component for each decomposition level of the subset of other decomposition levels, respectively and the third modified first wavelet component for the remaining decomposition levels lower than the highest decomposition level determined for thresholding, respectively, into a denoised signal.

23. The method of denoising a signal according to claim 22, wherein the subset of other decomposition levels does not include decomposition levels having coefficients only containing noise.

24. The method of denoising a signal according to claim 22, wherein the position of each of the one or more windows is such that the ends of the one or more windows are where a value of the coefficients change from non-zero to zero and zero to non-zero.

25. The method of denoising a signal according to claim 22, further comprising:
transforming a signal using an undecimated discrete wavelet transformation into the first wavelet component and a second wavelet component, both the first wavelet component and the second wavelet component having a plurality of coefficients, the first wavelet component and the second wavelet component having a plurality of decomposition levels, where the number of the plurality of coefficients in each level are the same;
positioning one or more windows on the second wavelet component for the highest decomposition level determined for thresholding;
for the highest decomposition level determined for thresholding, comparing each coefficient of the plurality of coefficients outside the one or more windows with a threshold, and selectively changing a value of the coefficient based on the comparison thereby generating a first modified second wavelet component having changed coefficients and unchanged coefficients for the highest decomposition level; and
transforming, using an inverse undecimated discrete wavelet transformation, the first modified first wavelet component for the highest decomposition level, the second modified first wavelet component for each decomposition level of the subset of other decomposition levels, respectively and the third modified first wavelet component for the remaining decomposition levels, respectively, and the first modified second wavelet component, into the denoised signal.

26. The method of denoising a signal according to claim 22, wherein the signal is a scan or an average of scans from an electron spin resonance (ESR)-based pulsed dipolar spectroscopy.

27. The method of denoising a signal according to claim 22, wherein the signal has a signal to noise ratio for a peak greater than 0.5.

28. The method of denoising a signal according to claim 22, wherein a signal to noise ratio for a peak is increased by at least three orders of magnitude in the denoised signal than in the signal.

29. A method of denoising a signal comprising:
reversing in time, a signal;
transforming the time reversed signal using an undecimated discrete wavelet transformation into at least a first wavelet component, the first wavelet component having a plurality of coefficients, the first wavelet component having a plurality of decomposition level, where a number of the plurality of coefficients in each level are the same;
for each decomposition level, dividing coefficients for the first wavelet component into a first-subset of coefficients and a second-subset of coefficients based on a determined signal to noise ratio of the signal;
for each decomposition level determined for thresholding for the first-subset of coefficients and the second-subset of coefficients,
comparing each coefficient in the first-subset of coefficients with a first threshold, and selectively changing a value of the coefficient in the first-subset of coefficients based on the comparison thereby generating a first modified first subset of coefficients having changed coefficients and unchanged coefficients; and
comparing each coefficient in the second-subset of coefficients with a second threshold, and selectively changing a value of the coefficient in the second-subset of coefficients based on the comparison thereby generating a first modified second subset of coefficients having changed coefficients and unchanged coefficients;
positioning one or more windows on the first modified first subset of coefficients and the first modified second subset of coefficients for a highest decomposition level determined for thresholding, by evaluating the changed coefficients and unchanged coefficients in the first modified first subset of coefficients and the first modified second subset of coefficients, respectively, for the highest decomposition level, respectively;
changing coefficients in the first modified first subset of coefficients and the first modified second subset of coefficients for the highest decomposition level, respectively, to its original value when the coefficients are within the one or more windows while keeping the coefficients outside the one or more windows the same as in the first modified first subset of coefficients and the first modified second subset of coefficients, respectively, to generate a second modified first subset of coefficients and a second modified second subset of coefficients, respectively, for the respective highest decomposition level;
positioning the one or more windows on the first modified first subset of coefficients and the first modified second subset of coefficients for a subset of other decomposition levels of the plurality of decomposition levels at the same positions;
changing coefficients in the first modified first subset of coefficients and the first modified second subset of coefficients for each of the subset of other decomposition levels to its original value when the coefficients are within the one or more windows while keeping the coefficients outside the one or more windows the same as the first modified first subset of coefficients and the first modified second subset of coefficients, respectively, to generate a third modified first subset of coefficients and a third modified second subset of coefficients, respectively, for a decomposition level of the subset of other decomposition levels;
transforming, using an inverse undecimated discrete wavelet transformation, the first modified first subset of coefficients and the first modified second subset of coefficients for decomposition levels other than the subset of other decomposition levels and the highest decomposition level, respectively, the second modified first subset of coefficients and the second modified second subset of coefficients for the highest decomposition level and the third modified first subset of coefficients and the third modified second subset of coefficients for the subset of other decomposition levels, respectively, into a reversed in time denoised signal; and
reversing in time the reversed in time denoised signal to generate a denoised signal.

30. The method of claim 29, wherein a number of decomposition level determined for thresholding for the first-subset of coefficients and the second-subset of coefficients are different.

31. The method of claim 29, wherein the position of the one or more windows on the first modified first subset of coefficients and the first modified second subset of coefficients is independently determined.

32. A method of denoising a signal comprising:
reversing in time, a signal;
transforming the time reversed signal using an undecimated discrete wavelet transformation into at least a first wavelet component, the first wavelet component having a plurality of coefficients, the first wavelet component having a plurality of decomposition level, where a number of the plurality of coefficients in each level are the same;
for each decomposition level, dividing coefficients for the first wavelet component into a first-subset of coefficients and a second-subset of coefficients based on a determined signal to noise ratio of the signal;
positioning one or more windows on the first-subset of coefficients and the second-subset of coefficients for a highest decomposition level determined for thresholding for the first-subset of coefficients and the second-subset of coefficients;
for the highest decomposition level determined for thresholding for the first-subset of coefficients and the second-subset of coefficients, comparing each coefficient outside the one or more windows in the first-subset of coefficients with a threshold, and selectively changing a value of the coefficient based on the comparison thereby generating a first modified first wavelet coefficients having changed coefficients and unchanged coefficients for the highest decomposition level and comparing each coefficient outside the one or more windows in the second-subset of coefficients with a second threshold and selectively changing a value of the coefficient based on the comparison thereby generating a first modified second wavelet component having changed coefficients and unchanged coefficients for the highest decomposition level determined for thresholding, respectively;

positioning the one or more windows on the first subset of coefficients for a subset of other decomposition levels of the plurality of decomposition levels at the same positions;

changing coefficients in the first-subset of coefficients for each of the subset of other decomposition levels when the coefficients are outside the windows and based on a comparison with a threshold, respectively, to generate a second modified first subset of coefficients having changed coefficients and unchanged coefficients, respectively, for a decomposition level of the subset of other decomposition levels;

for the remaining decomposition levels of the plurality of decomposition levels lower than the highest decomposition level determined for thresholding, comparing each coefficient in the first-subset of coefficients with a threshold and selectively changing a value of the coefficient based on the comparison thereby generating a third modified first wavelet coefficients having changed coefficients and unchanged coefficients, respectively for each decomposition level of the remaining decomposition levels; and transforming, using an inverse undecimated discrete wavelet transformation, a first modified first wavelet coefficients and first modified second wavelet coefficients for the highest decomposition level, a second modified first subset of coefficients, respectively, and the third modified first wavelet coefficients, respectively, into a reversed in time denoised signal; and reversing in time the reversed in time denoised signal to generate a denoised signal.

\* \* \* \* \*